(12) United States Patent
Flavell et al.

(10) Patent No.: US 10,260,042 B2
(45) Date of Patent: Apr. 16, 2019

(54) COMPOSITIONS AND METHODS FOR DIMINISHING AN IMMUNE RESPONSE

(71) Applicants: Yale University, New Haven, CT (US); Ospedale San Raffaele Srl, Milan (MI) (IT); Fondazione Telethon, Rome (IT)

(72) Inventors: Richard A. Flavell, Guilford, CT (US); Nicola Gagliani, New Haven, CT (US); Silvia Gregori, Buccinasco (IT); Samuel Huber, Hamburg (DE); Chiara Francesca Magnani, Milan (IT); Maria Grazia Roncarolo, Segrate (IT)

(73) Assignees: Yale University, New Haven, CT (US); Ospedale San Raffaele S.r.l., Milan (MI) (IT); Fondazione Telethon, Rome (RM) (IT)

( * ) Notice: Subject to any disclaimer, the term of this patent is extended or adjusted under 35 U.S.C. 154(b) by 0 days.

(21) Appl. No.: 15/711,194

(22) Filed: Sep. 21, 2017

(65) Prior Publication Data

US 2018/0119099 A1 May 3, 2018

Related U.S. Application Data

(62) Division of application No. 14/407,627, filed as application No. PCT/US2013/046378 on Jun. 18, 2013.

(60) Provisional application No. 61/661,172, filed on Jun. 18, 2012, provisional application No. 61/816,497, filed on Apr. 26, 2013.

(51) Int. Cl.
| | |
|---|---|
| *C12N 5/00* | (2006.01) |
| *C12N 5/02* | (2006.01) |
| *C12N 5/0783* | (2010.01) |
| *A61K 35/17* | (2015.01) |

(52) U.S. Cl.
CPC ............ *C12N 5/0637* (2013.01); *A61K 35/17* (2013.01); *C12N 2501/231* (2013.01); *C12N 2501/2302* (2013.01); *C12N 2501/2315* (2013.01); *C12N 2501/24* (2013.01); *C12N 2501/515* (2013.01)

(58) Field of Classification Search
None
See application file for complete search history.

(56) References Cited

U.S. PATENT DOCUMENTS

| | | | |
|---|---|---|---|
| 6,010,905 A | 1/2000 | Cohen et al. | |
| 6,277,635 B1 | 8/2001 | Roncarolo et al. | |
| 7,771,932 B1 | 8/2010 | Groux et al. | |
| 9,234,174 B2 | 1/2016 | Gregori | |
| 2003/0211100 A1 | 11/2003 | Bedian et al. | |
| 2004/0241167 A1 | 12/2004 | Suciu-Foca et al. | |
| 2007/0269436 A1 | 11/2007 | Chen | |
| 2012/0141564 A1 | 6/2012 | Dennis et al. | |
| 2015/0132272 A1 | 5/2015 | Flavell et al. | |
| 2016/0046910 A1 | 2/2016 | Gregori et al. | |

FOREIGN PATENT DOCUMENTS

| | | |
|---|---|---|
| WO | 2003/102162 A2 | 12/2003 |
| WO | 2003/102162 A3 | 12/2003 |
| WO | 2004/087899 A1 | 10/2004 |
| WO | 2010/095043 A1 | 8/2010 |

OTHER PUBLICATIONS

Huang et al., 2004, Immunity. vol. 21: 503-513.*
Hathcock et al., 1993, Immunol. Res. vol. 12: 21-36.*
Okamura, T. et al., "CD4+CD25–LAG3+ Regulatory T Cells Controlled by the Transcription Factor Egr-2.", Proc Natl Acad Sci USA, Aug. 4, 2009, vol. 106, pp. 13974-13979.
Lozano, E. et al., "The TIGIT/CD226 Axis Regulates Human T Cell Function.", Journal of Immunology, Mar. 16, 2012, vol. 188, pp. 3869-3875.
Magnani, C. et al., "Killing of Myeloid APCs Via HLA Class I, CD2 and CD226 Defines a Novel Mechanisin of Suppression by Human Tr1 Cells.", European Journal of Immunology, May 13, 2011, vol. 41, pp. 1652-1662.
Gagliani, N., et al., "Coexpression of CD49b and LAG-3 Identifies Human and Mouse T Regulatory Type 1 Cells.", Nature Medicine, Apr. 28, 2013, vol. 19, pp. 739-748.
Huber, S. et al., Th17 cells express interleukin-10 receptor and are controlled by Foxp3– and Foxp3+ regulatory CD4+ T cells in an interleukin-10 dependent manner, Immunity, Apr. 22, 2011, vol. 34, No. 4, pp. 554-565.
Steinbrink, et al., "Induction of tolerance by IL-10-treated dendritic cells", Journal of Immunology, US. vol. 159, No. 10, Nov. 15, 1997 (Nov. 15, 1997), pp. 4772-4780, XP002265198.
Steinbrink, et al., "CD4+ and CD8+ anergic T cells induced by interleukin-10-treated human dendritic cells display antigen-specific suppressor activity," Blood. vol. 99, No. 7, Apr. 1, 2002 (Apr. 1, 2002), pp. 2468-2476, XP002445320.
Hauben, et al., "IL-10-dependent Induction of a new subset of Tolerogenic Antigen Presenting Cells", FASEB Journal, vol. 18, No. 4-5, 2004, pp. Abst. 91.4, XP002445321, FASEB Meeting on Experimental Biology: Translating the Genome; Washington, DC, USA; Apr. 17-21, 2004.
Gregori, et al., "Induction of CD4+regulatory T cells by IL-10-modulated dendritic cells", Journal of Immunology, US, vol. 176, No. suppl, May 1, 2006 (May 1, 2006), pp. 216, XP009087661.

(Continued)

*Primary Examiner* — Amy E Juedes
(74) *Attorney, Agent, or Firm* — Lucas & Mercanti, LLP

(57) ABSTRACT

The invention is based upon the discovery that T regulatory type 1 (Tr1) cells express particular cell surface markers that allow for their selection, enrichment, isolation, purification and administration. The ability to use the particular markers described herein to select, enrich, isolate, purify and administer Tr1 cells allows for improved methods of Tr1 therapies for treating a wide variety of diseases and disorders.

13 Claims, 52 Drawing Sheets

(56) References Cited

OTHER PUBLICATIONS

Gregori, et al., "Differentiation of type 1 T regulatory cells (Tr1) by tolerogenic DC-10 requires the IL-10-dependent ILT4/HLA-G pathway", Blood, 12(116):935-944, 2010.

Ramadan, et al., "In vitro generation of human CD86+ dendritic cells from CD34+ haematopoietic progenitors by PMA and in serum-free medium", Clinical and Experimental Immunology, vol. 125, 2001, pp. 237-244.

Wakkach, et al., "Characterization of Dendritic Cells that Induce Tolerance and T Regulatory 1 Cell Differentiation In Vivo", Immunity, vol. 18, 2003, pp. 605-617.

Amodio, et al., "HLA-G expressing DC-10 and CD4+ T cells accumulated in human decidua during pregnancy", Human Immunology, vol. 74, 2013, pp. 406-411.

Mitra, et al., "Psoriatic Skin-Derived Dendritic Cell Function is Inhibited by Exogenous IL-10", The Journal of Immunology, vol. 154(6), 1995, pp. 2668-2677.

Groux, et al., "Role of dendritic cells in the generation of regulatory T cells" (Seminars in Immunology vol. 16, available online 2004, pp. 99-106).

Hauben, et al., "IL-10-dependent induction of a new subset of Telerogenic Antigen Presenting Cells," (FASEB Journal Meeting Abstract, abstract only,published Apr. 2004).

Behi, et al., "New insights into cell responses involved in experimental autoimmune encephalomyelitis and multiple sclerosis," Immunology Letters 2005, vol. 96, Sep. 1, 2004, pp. 11-26.

Min, et al., "Antigen-Induced, Tolerogenic CD11c+,DC11b+ Dendritic Cells Are Abundant in Peyer's Patches During the Induction of Oral Tolerance to Type II Collagen and Suppress Experimental Collagen-Induced Arthritis," Arthritis & Rheumatism, vol. 54, No. 3, Mar. 2006, pp. 887-898.

Levings et al., "Differentiation of Tr1 cells by immature dendritic cells requires IL-10 but not CD25+CD4+Tr cells", Blood, 2005, vol. 105, No. 3, pp. 1162-1169.

* cited by examiner

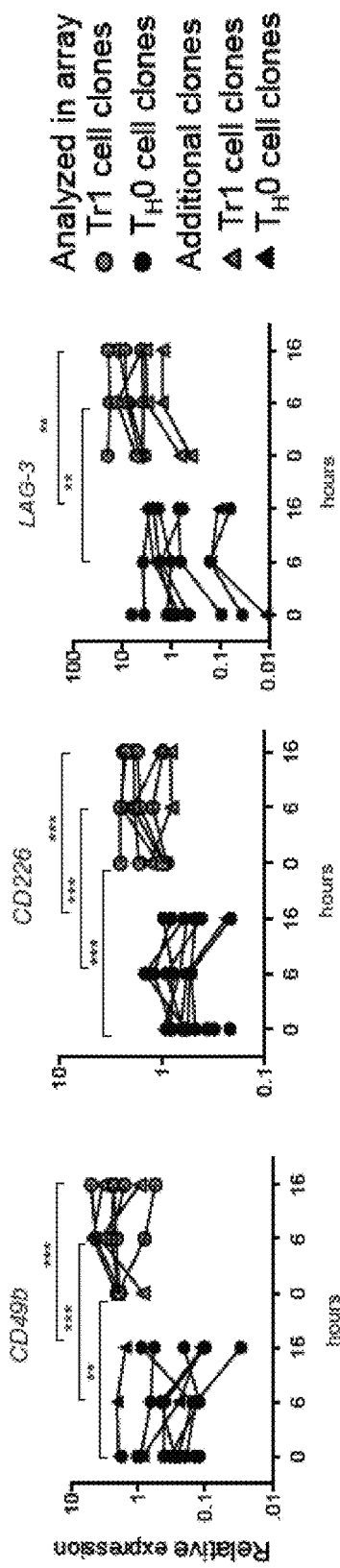
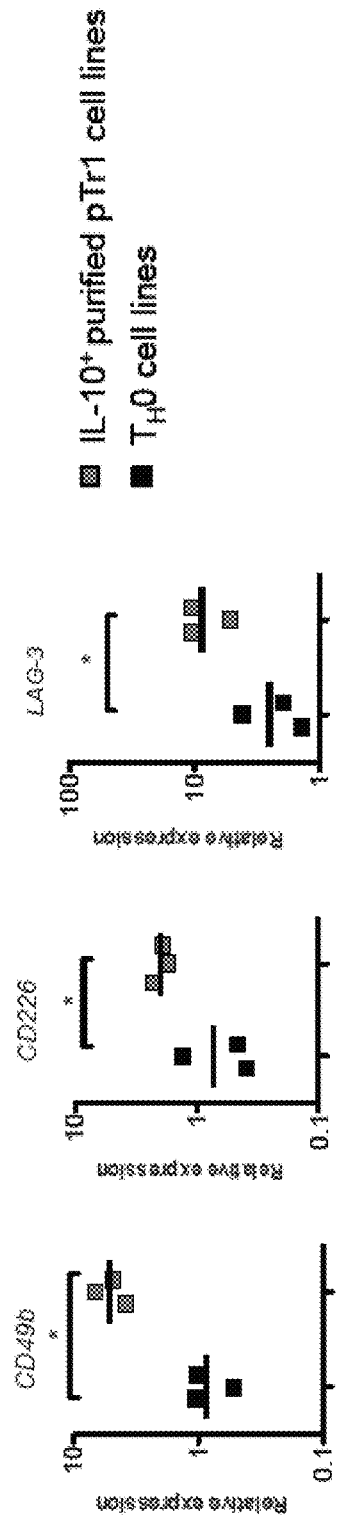
Fig. 7C
Fig. 7D

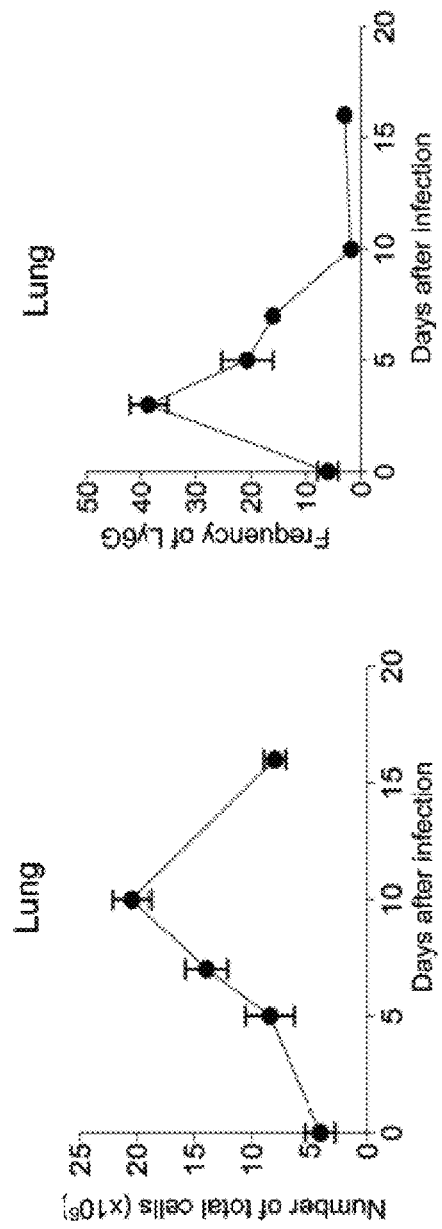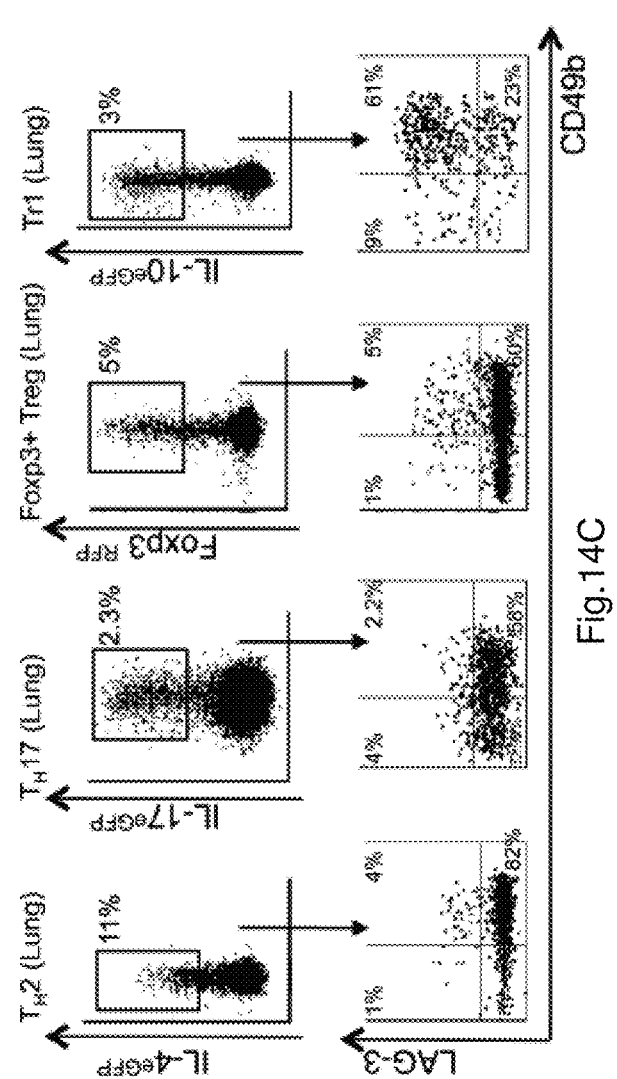

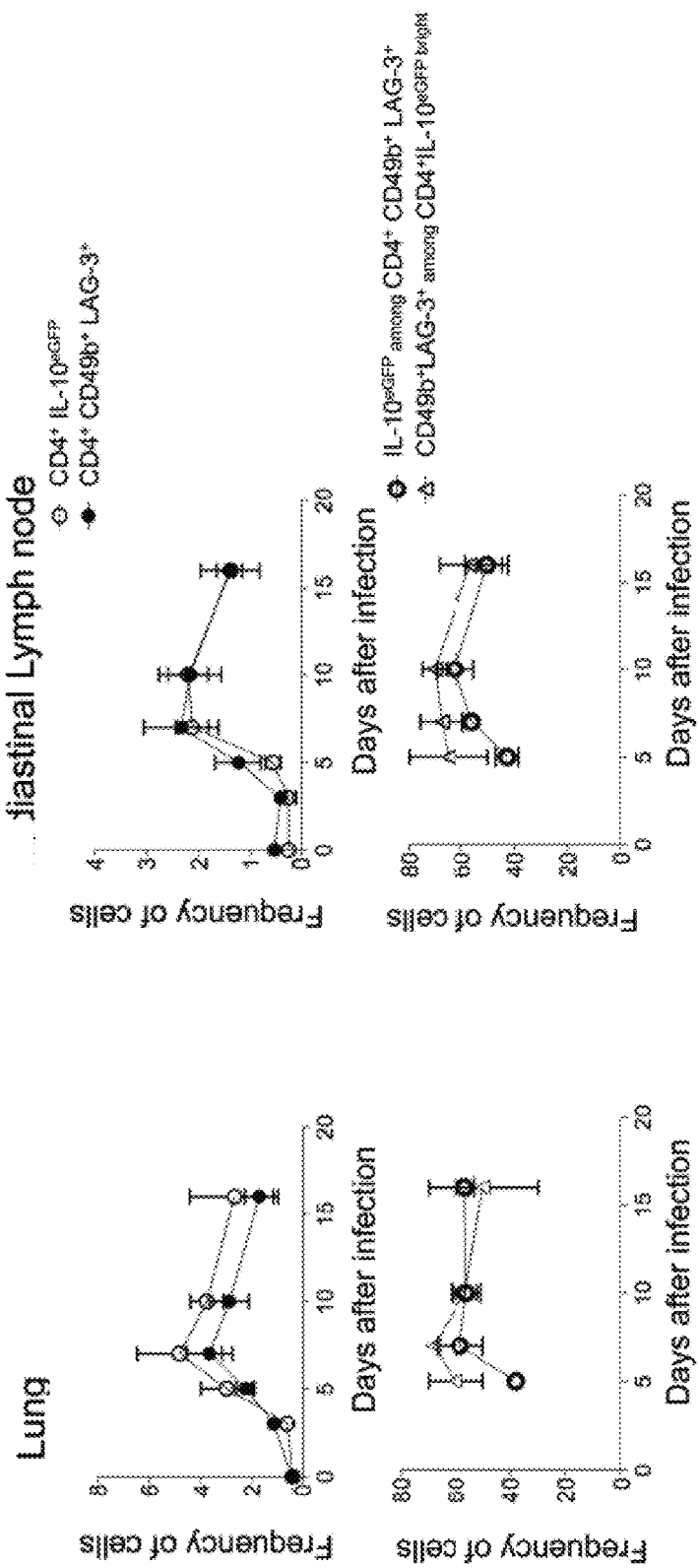

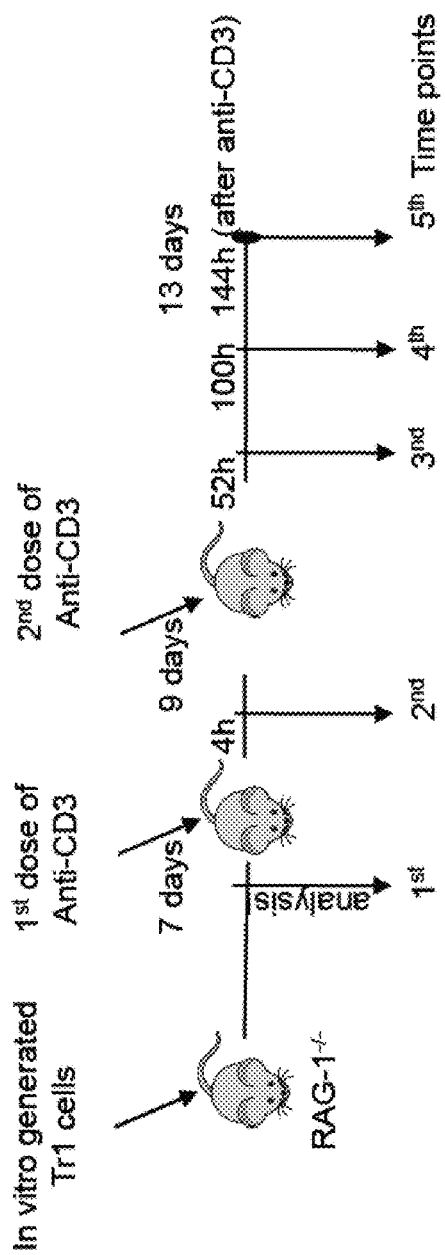
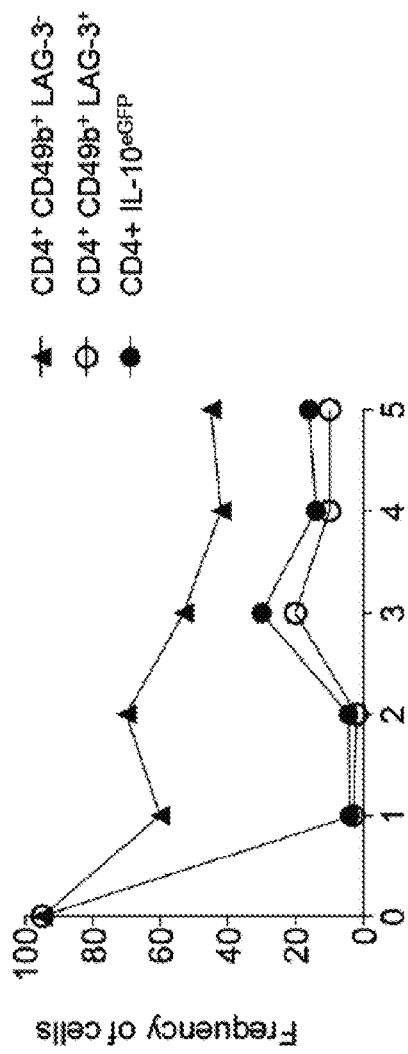
Fig.18A
Fig.18B

COMPOSITIONS AND METHODS FOR DIMINISHING AN IMMUNE RESPONSE

CROSS-REFERENCE TO RELATED APPLICATIONS

This application is a Divisional of U.S. patent application Ser. No. 14/407,627, filed Dec. 12, 2014, which in turn is a 371 of PCT International Application No. PCT/US2013/046378, filed Jun. 18, 2013, which claims the benefit of U.S. Provisional Application Ser. No. 61/661,172, filed Jun. 18, 2012, and U.S. Provisional Application Ser. No. 61/816,497 filed Apr. 26, 2013, the contents of each of which are incorporated herein by reference.

BACKGROUND OF THE INVENTION

T regulatory type 1 (Tr1) cells were discovered in peripheral blood of severe combined immunodeficiency patients with long-term mixed chimerism after HLA-mismatched fetal liver hematopoietic stem cell transplant (HSCT) (Roncarolo et al., 1988, J Exp Med 167, 1523-1534; Bacchetta et al., 1994, J Exp Med 179, 493-502). Tr1 cells have strong immunosuppressive capacity in several immune-mediated diseases (Roncarolo and Battaglia, 2007, Nat Rev Immunol 7, 585-598; Roncarolo et al., 2011, Immunol Rev 241, 145-163; Pot et al., 2011, Semin Immunol 23, 202-208). The secretion of high levels of IL-10, and the killing of myeloid antigen-presenting cells (APCs) via Granzyme B are the main mechanisms of Tr1-mediated suppression (Groux et al., 1997, Nature 389, 737-742; Magnani et al., 2011 Eur J Immunol 41, 1652-1662). To date specific biomarkers for Tr1 cells have not been identified, limiting their study and clinical application. Tr1 cells are distinguished from T helper ($T_H$)1, $T_H$2, and $T_H$17 cells by their unique cytokine profile and the regulatory function. Tr1 cells secrete higher levels of IL-10 than IL-4 and IL-17, the hallmark cytokines of $T_H$2 and $T_H$17 cells, respectively. Tr1 cells also secrete low levels of IL-2 and, depending on the local cytokine milieu, can produce variable levels of IFN-γ, together, the key $T_H$1 cytokines (Roncarolo et al., 2011, Immunol Rev 241, 145-163). FOXP3 is not a biomarker for Tr1 cells since its expression is low and transient upon activation. IL-10-producing Tr1 cells express ICOS (Haringer et al., 2009, J Exp Med 206, 1009-1017) and PD-1 (Akdis et al., 2004, J Exp Med 199, 1567-1575), but these markers are not specific (Maynard et al., 2007, Nat Immunol 8, 931-941). CD49b, the α2 integrin subunit of the very-late-activation antigen (VLA)-2, has been proposed as a marker for IL-10-producing T cells (Charbonnier et al., 2006, J Immunol 177, 3806-3813); but it is also expressed by human $T_H$17 cells (Boisvert et al., 2010, Eur J Immunol 40, 2710-2719). Moreover, murine CD49b$^+$ T cells secrete IL-10 (Charbonnier et al., 2006, J Immunol 177, 3806-3813) but also pro-inflammatory cytokines (Kassiotis et al., 2006, J Immunol 177, 968-975). Lymphocyte activation gene-3 (LAG-3), a CD4 homolog that binds with high affinity to MHC class II molecules, is expressed by murine IL-10-producing CD4$^+$ T cells (Okamura et al., 2009, Proc Natl Acad Sci USA 106, 13974-13979), but also by activated effector T cells (Workman and Vignali, 2005, J Immunol 174, 688-695; Bettini et al., 2011, J Immunol 187, 3493-3498; Bruniquel et al., 1998, Immunogenetics 48, 116-124; Lee et al., 2012, Nat Immunol 13, 991-999) and by FOXP3$^+$ regulatory T cells (Tregs) (Camisaschi et al., 2010, J Immunol 184, 6545-6551). It was recently shown that human Tr1 cells express CD226 (DNAM-1), which is involved in the specific killing of myeloid APCs (Magnani et al., 2011 Eur J Immunol 41, 1652-1662). Overall, none of the abovementioned markers has been confirmed to be selective for Tr1 cells.

Tr1 cell-based clinical approaches are still largely limited by the inability to transfer a pure population of these cells. Moreover, a high frequency of Tr1 cells has been correlated with a positive outcome after HSCT (Bacchetta et al., 1994, J Exp Med 179, 493-502; Serafini et al., 2009, Haematologica 94, 1415-1426), but the absence of suitable markers has made the clinical screening of this type of Tr1 cells impossible. Hence, the availability of specific biomarkers of Tr1 cells would facilitate the transition of therapies targeting Tr1 cells from bench to bedside.

Thus, there is a need in the art for compositions and methods to identify and purify Tr1 cells. The present invention satisfies this unmet need.

SUMMARY OF THE INVENTION

The invention described herein is based in part upon the discovery that T regulatory type 1 (Tr1) cells express particular cell surface markers that allow for their selection, enrichment, isolation, purification and administration. In one embodiment, the invention is a composition comprising an enriched population of T regulatory type 1 (Tr1) cells, wherein the Tr1 cells in the enriched population of Tr1 cells express the cell surface markers CD4, and CD49b, and LAG-3. In some embodiments, the Tr1 cells also express the cell surface marker CD226. In some embodiments, the Tr1 cells express the cell surface marker CD226 at a level greater than the level of CD226 expressed by a comparator cell population. In various embodiments, the comparator cell population is at least one selected from the group consisting of CD49b-LAG-3– T cells and TH0 cells. In some embodiments, the Tr1 cells do not constitutively express high levels of Foxp3, as compared with the level of Foxp3 on a comparator cell selected from the group consisting of a CD25bright T cell and a Foxp3+ Treg cell. In one embodiment, greater than 90% of the cells in the enriched population of Tr1 cells express the cell surface markers CD4, and CD49b, and LAG-3. In another embodiment, greater than 95% of the cells in the enriched population of Tr1 cells express the cell surface markers CD4, and CD49b, and LAG-3. In another embodiment, greater than 98% of the cells in the enriched population of Tr1 cells express the cell surface markers CD4, and CD49b, and LAG-3. In another embodiment, wherein greater than 99% of the cells in the enriched population of Tr1 cells express the cell surface markers CD4, and CD49b, and LAG-3.

In another embodiment, the invention is a method of isolating an enriched population of Tr1 cells from a biological sample of a subject including the steps of obtaining a T cell-containing biological sample of a subject, and isolating cells from the biological sample of the subject that express the cell surface markers CD4, CD49b, and LAG-3. In some embodiments, the method includes the additional step of removing cells that express high levels of Foxp3 from the enriched population of Tr1 cells. In some embodiments, the method includes the additional step of isolating cells from the biological sample of the subject that express the cell surface marker CD226. In some embodiments, the cells express the cell surface marker CD226 at a level greater than the level of CD226 expressed by a comparator cell population. In one embodiment, the comparator cell population is at least one selected from the group consisting of CD49b-LAG-3– T cells and TH0 cells. In some embodiments, greater than 90% of the cells in the enriched population of Tr1 cells express the cell surface markers CD4, and CD49b, and LAG-3. In some embodiments, greater than 95% of the cells in the enriched population of Tr1 cells express the cell surface markers CD4, and CD49b, and LAG-3. In some embodiments, greater than 98% of the cells in the enriched population of Tr1 cells express the cell surface markers CD4, and CD49b, and LAG-3. In some embodiments, greater than 99% of the cells in the enriched population of Tr1 cells express the cell surface markers CD4, and CD49b, and LAG-3. In one embodiment, the step of isolating cells from the biological sample of the subject employs the use of antibody that specifically binds to a cell surface marker. In various embodiments, the cell surface marker is at least one selected from the group consisting of CD4, CD49b, and LAG-3. In some embodiments, the step of cells from the biological sample of the subject employs the use of fluorescence-activated cell sorting (FACS). In various embodiments, the biological sample is at least one selected from the group consisting of blood, bone marrow, cord blood, lymph, thymus, and spleen.

In one embodiment, the invention is a method of treating or preventing a disease or disorder in a subject in need thereof, the method comprising administering to the subject an effective amount of Tr1 cells that express the cell surface markers CD4, and CD49b, and LAG-3. In some embodiments, the disease or disorder is at least one selected from the group consisting of an inflammatory disease and disorder, an autoimmune disease or disorder, and a disease or disorder associated with transplantation. In other embodiments, the disease or disorder is at least one selected from the group consisting of allergy, asthma, inflammatory bowel disease, autoimmune entheropathy, Addision's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, cell and organ transplant rejection and graft versus host disease. In one embodiment, the subject is human.

In another embodiment, the invention is a method of inhibiting alloreactive T cells in a subject in need thereof, the method including the step of contacting the alloreactive T cells with an effective amount of Tr1 cells that express the cell surface markers CD4, and CD49b, and LAG-3.

In another embodiment, the invention is a method of inhibiting a T cell mediated immune response in a subject in need thereof, the method including the step of contacting at least one T-lymphocyte with an effective amount of Tr1 cells that express the cell surface markers CD4, and CD49b, and LAG-3. In some embodiments, the inhibited T cell mediated immune response is an effector T cell activity and the at least one T-lymphocyte is a CD4+ T-lymphocyte. In some embodiments, the inhibited T cell mediated immune response is a cytotoxic T-lymphocyte (CTL) activity and the at least one T-lymphocyte is a cytotoxic T-lymphocyte.

In one embodiment, the invention is a method of generating an immunomodulatory effect in a subject having an alloreactive response, inflammatory response, or autoimmune response, including the step of administering to said subject an effective amount of CD4+CD49+LAG-3+ Tr1 cells.

In another embodiment, the invention is a method of preventing or treating an alloreactive response, inflammatory response, or autoimmune response in a subject, including the step of administering to said subject, prior to onset of the alloreactive response, inflammatory response, or autoimmune response, an effective amount of CD4+CD49+LAG-3+ Tr1 cells to prevent said response.

In one embodiment, the invention is a composition comprising CD4+CD49+LAG-3+ Tr1 cells for use in treating or preventing a disease or disorder in a subject in need thereof, wherein the disease or disorder is at least one selected from the group consisting of an inflammatory disease and disorder, an autoimmune disease or disorder, and a disease or disorder associated with transplantation.

In another embodiment, the invention is a composition comprising CD4+CD49+LAG-3+ Tr1 cells for use in treating or preventing a disease or disorder in a subject in need thereof, wherein the disease or disorder is at least one selected from the group consisting of allergy, asthma, inflammatory bowel disease, autoimmune entheropathy, Addision's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, cell and organ transplant rejection and graft versus host disease.

In one embodiment, the invention is a composition comprising CD4+CD49+LAG-3+ Tr1 cells for use in inhibiting alloreactive T cells in a subject in need thereof.

In another embodiment, the invention is a composition comprising CD4+CD49+LAG-3+ Tr1 cells for use in inhibiting a T cell mediated immune response in a subject in need thereof. In some embodiments, the inhibited T cell mediated immune response is an effector T cell activity. In other embodiments, the inhibited T cell mediated immune response is a cytotoxic T-lymphocyte (CTL) activity.

In one embodiment, the invention is a composition comprising CD4+CD49+LAG-3+ Tr1 cells for use in generating an immunomodulatory effect in a subject having an alloreactive response, inflammatory response, or autoimmune response, the method comprising administering to said subject an effective amount of CD4+CD49+LAG-3+ Tr1 cells.

In another embodiment, the invention is a composition comprising CD4+CD49+LAG-3+ Tr1 cells for use in preventing or treating an alloreactive response, inflammatory response, or autoimmune response in a subject, said method comprising administering to said subject, prior to onset of the alloreactive response, inflammatory response, or autoimmune response, an effective amount of CD4+CD49+LAG-3+ Tr1 cells to prevent said response.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A: Following data normalization by standard Robust Multichip Analysis (RMA) protocol and statistical analysis (t test welch without the False Discovery Rate, FDR, correction), Tr1 and $T_H0$ cell populations were compared at the three time points. Normalized expression values for profiles directly comparing Tr1 vs. $T_H0$ cell clones at t0, 6 h and 16 h are shown. FIG. 1B-1C: Two-dimensional heatmaps of genes differentially expressed (DEGs) encoding for membrane proteins in Tr1 as compared to $T_H0$ cell clones. Heatmap of DEGs in Tr1, as compared to $T_H0$ cell clones, at the three time points (t0, t6 h, and t16 h) (FIG. 1B) and at 6 h and 16 h (FIG. 1C) are shown. Red genes are expressed at higher levels compared to the mean signal intensities in all experiments, whereas down-regulated genes are in green, and in black are signal intensities close to the mean expression level. The rows are scaled to have mean zero and standard deviation one. Gene Name, and Gene Symbol are indicated. (FIG. 1D) Expression of CD49b, LAG-3, and CD226 measured by flow cytometry in Tr1 and $T_H0$ cell clones. Percentages of CD49b$^+$, and of LAG-3$^+$, and mean fluorescence intensity (MFI) of CD226 in Tr1 and $T_H0$ cell clones are presented. P=p≤0.005, **p<0.0001.

FIG. 2, comprising FIG. 2A: Expression of CD49b and LAG-3 (gated on CD4$^+$CD45RA$^-$ T cells) in blood of HDs. Dot plots of 1 representative donor out of 23 donors are presented (left and middle panels); percentages of cells in each quadrant are indicated. Percentages of CD49b$^+$LAG-3$^-$, CD49b$^-$LAG-3$^+$, and CD49b$^+$LAG-3$^+$ T cells in each donor analysed are shown (right panel). FIG. 2B: Concentration levels of IL-10, IL-4, IFN-γ and IL-17 in culture supernatants of the indicated FACS-sorted T cell populations stimulated with antibodies to CD3 and CD28. Mean±SEM; n=9 (IL-10, IL-4 and IFN-γ) and n=4 (IL-17). Ratios of IL-10 vs. IL-4, IFN-γ and IL-17 in 1 representative donor out of 9 tested for IL-10/IL-4 and IL-10/IFN-γ, and 4 tested for IL-10/IL-17 are shown. *P≤0.05, **P≤0.005. When not indicated differences were not statistically different. FIG. 2C: Suppression mediated by the indicated FACS-sorted T cell populations. One representative experiment out of 6 (left panel), and percentages of suppression in 6 independent experiments are shown (right panel). P=*p≤0.05, ** P≤0.005.

FIG. 3, comprising FIG. 3A: Expression of CD49b and LAG-3 measured on CD4$^+$ TCRβ$^+$Foxp3$^{RFP-}$IL-10$^{eGFPbright}$ or IL-10$^{eGFP-}$ T cells (left panel). Percentages of cells in each quadrant are indicated. Frequencies (mean±SEM) of cells co-expressing CD49b and LAG-3 among Tr1 cells (defined as CD4$^+$ TCRβ$^+$Foxp3$^{RFP-}$IL-10$^{eGFPbright}$) and CD4$^+$IL-10$^-$ T cells (defined as CD4$^+$ TCRβ$^+$IL-10$^{eGFP-}$) obtained in 5 independent experiments (right panel) are shown. P=p≤0.005. FIG. 3B: IL-10$^{eGFP}$ frequency and MFI in the indicated T cell populations (gated on CD4$^+$ TCRβ$^+$Foxp3$^{RFP-}$) isolated from the small intestine of anti-CD3 treated mice. Representative dot plots from 1 experiment out of 5 are shown (left panel). In each experiment 2 to 5 mice were pooled. Percentages of cells in each quadrant are indicated. MFI for IL-10$^{eGFP+}$ T cells in the indicated T cell populations are shown (right panel). FIG. 3C: Mean±SEM of IL-10$^{eGFP+}$ cell frequencies among the indicated T cell populations obtained in 5 independent experiments is shown.  P≤0.005. FIG. 3D: Concentration levels of IL-10, IL-4, IFN-γ and IL-17A in culture supernatants of the indicated FACS-sorted T cell populations (gated on CD4$^+$ TCRβ$^+$Foxp3$^{RFP-}$) from the small intestine of anti-CD3 treated mice (Mean±SEM) and the ratios of IL-10 vs. IL-4, IFN-γ and IL-17A in 1 representative experiment out of 3 are shown. In each experiment cells isolated from 5 mice were pooled before FACS-sorting. Each experiment contains at least 3 replicates of the same sample for each population. * P≤0.05,  P≤0.005, * P≤0.0005. When not indicated differences were not statistically different.

FIG. 4, comprising FIG. 4A: Suppression mediated by the indicated FACS-sorted T cell populations isolated from the small intestine of anti-CD3 treated mice. One representative experiment out of 3 (left panel), and mean±SEM of the percentages of suppression in 3 independent experiments (right panel) are shown. P=p≤0.005. When not indicated differences were not statistically different. FIG. 4B: eT$_H$17 (CD4$^+$ TCRβ$^+$Foxp3$^{RFP-}$IL-17A$^{eGFP+}$) cells were isolated from the colon and mesenteric lymph nodes of RAG1$^{-/-}$ mice injected with CD4$^+$CD45RB$^{High}$ T cells isolated from Foxp3$^{RFP}$IL-17A$^{eGFP}$ double reporter mice. The indicated T cell populations were isolated from the small intestine of anti-CD3-treated mice and injected i.p. in combination with eT$_H$17 (ratio 1:1) into RAG1$^{-/-}$ mice. FIG. 4C: Representative endoscopic (upper panels) and histological (lower panels) pictures. Endoscopic (FIG. 4D), mass loss (FIG. 4E) colitis score were measured. Each dot represents 1 mouse. Lines indicate mean±SEM.  P≤0.005, and *** P≤0.0005.

FIG. 5, comprising FIG. 5A: Expression of CD49b and LAG-3 measured on CD4$^+$ TCRβ$^+$IL-4$^{eGFP+}$ (T$_H$2), CD4$^+$ TCRβ$^+$Foxp3$^{RFP-}$ IL-17A$^{eGFP+}$ (T$_H$17) and CD4$^+$ TCRβ$^+$Foxp3$^{RFP+}$IL-17A$^{eGFP-}$ (Foxp3$^+$ Tregs) cells isolated from the draining lymph nodes of IL-4$^{eGFP}$ and Foxp3$^{RFP}$IL-17A$^{eGFP}$ mice 10 days after N. brasiliensis infection. Dot plots from 1 representative experiment out of 3 are shown. Percentages of cells in each quadrant are indicated. FIG. 5B: Expression of CD49b and LAG-3 on CD4$^+$ TCRβ$^+$Foxp3$^{RFP-}$IL-10$^{eGFPbright}$ T cells isolated from the draining lymph nodes of Foxp3$^{RFP}$IL-10$^{eGFP}$ mice infected with N. brasiliensis. Dot plots from 1 representative experiment out of 4 are shown. Percentages of cells in each quadrant are indicated. FIG. 5C: Mean±SEM of frequencies of cells co-expressing CD49b and LAG-3 among the indicated T cells isolated from the draining lymph nodes of infected mice (n=5 for each groups). ***P≤0.0005. FIG. 5D: Frequencies of CD4$^+$IL-10$^{eGFP+}$ T cells and IL-10$^{eGFP}$ MFI in the indicated T cell populations (gated on CD4$^+$ TCRβ$^+$Foxp3$^{RFP-}$) from the draining lymph nodes of Foxp3$^{RFP}$IL-10$^{eGFP}$ mice 10 days after *N. brasiliensis* infection. Dot plots from 1 representative experiment out of 4 are shown. Percentages of cells in each quadrant are indicated. FIG. 5E: Mean±SEM of IL-10$^{eGFP+}$ cell frequencies among the indicated T cell populations isolated from the draining lymph nodes of infected Foxp3$^{RFP}$IL-10$^{eGFP}$ mice (n=5 for each groups). *P≤0.05, ***P≤0.0005. FIG. 5F: Suppression mediated by the indicated FACS-sorted T cell populations from the draining lymph nodes of infected Foxp3$^{RFP}$IL-10$^{eGFP}$ mice. One representative experiment out of 3 (left panel) and mean±SEM of the percentages of suppression obtained in 3 independent experiments (the right panel) are shown. *P≤0.05 and **P≤0.005.

FIG. 6, comprising FIG. 6A: Percentages of CD49b$^+$LAG-3$^-$, CD49b$^-$LAG-3$^+$, and CD49b$^+$LAG-3$^+$ cells in Tr1 (pTr1) and T$_H$0 cell lines polarized with artificial APC. P≤0.005. When not indicated differences were not statistically different. FIG. 6B: Percentages of CD49b$^+$LAG-3$^-$, CD49b$^-$LAG-3$^+$, and CD49b$^+$LAG-3$^±$ cells in pTr1(DC-10) and T(mDC) cell lines polarized with DC. P≤0.005 and ***P≤0.0005. When not indicated differences were not statistically different. FIG. 6C: IL-10 levels in culture supernatants of pTr1 cell lines and of FACS-sorted CD49b$^+$LAG-3$^+$ T cells from pTr1 cells (CD49b$^+$LAG-3$^+$ pTr1). Mean±SEM (n=4). *P0.05. FIG. 6D: Suppression mediated by pTr1 cells and CD49b$^+$LAG-3$^+$ T cells sorted from pTr1 cells (CD49b$^+$LAG-3$^+$ pTr1). One representative experiment out of 5 (left panel), and percentages of suppression in 5 independent experiments (right panel) are shown. **P≤0.005. FIG. 6E: Expression of CD49b and LAG-3 (gated on CD4$^+$CD45RA$^-$ T cells) in subjects with complete chimerism (CC) and persistent mixed chimerism (PMC) after allogeneic HSCT. Representative dot plots from 1 out of 7 CC and 1 out 11 PMC are shown, percentages of cells in each quadrant are indicated. FIG. 6F: Percentages of CD49b$^+$LAG-3$^-$, CD49b$^-$LAG-3$^+$, and CD49b$^+$LAG-3$^+$ T cells in each healthy donor (HD) and transplanted subjects analysed. *P≤0.05, P≤0.005, * P≤0.0005. When not indicated differences were not statistically different.

FIG. 7, comprising FIG. 7A through FIG. 7D, depicts the results of experiments demonstrating the validation and selection of genes encoding for CD49b, CD226, and LAG-3. Tr1 and T$_H$0 cell clones, isolated from peripheral blood of 2 Healthy Donors (HDs). mRNA from cells unstimulated (t0, n=4 Tr1 cell clones and n=10 T$_H$0 cell clones) or stimulated with immobilized anti-CD3 and soluble anti-CD28 mAbs (6 h and 16 h, n=4 Tr1 cell clones and n=5 T$_H$0 cell clones) was isolated FIG. 7A: Expression of IL-10, GZB, and PD1 determined by the DNA microarray is shown. *P 0.05 and P 0.005. FIG. 7B: Expression of CD49b, CD226, and LAG-3 determined by the DNA microarray is shown. P 0.005. When not indicated differences were not statistically different. FIG. 7C: Expression of CD49b, CD226, and LAG3 in T$_H$0 and Tr1 cell clones. Following normalization to HPRT and B2M, relative mRNA amounts of T cell clones were adjusted to corresponding expression levels of a calibrator (pool of CD4$^+$ T cell lines from 4 HDs). Numbers represent arbitrary units. P 0.005 and *P 0.0005. When not indicated differences were not statistically different. FIG. 7D: IL-10-producing cells purified from pTr1 and T$_H$0 cell lines were stimulated for 6 h with immobilized anti-CD3 and soluble anti-CD28 mAbs. Expression of the indicated genes was investigated by RT-PCR. Following normalization to HPRT, relative mRNA amounts of T cells were adjusted to corresponding expression levels of a calibrator (pool of CD4$^+$ T cell lines from 4 HDs). Numbers represent arbitrary units. *P 0.05.

FIG. 8, comprising FIG. 8A: Expression of CD226 in the indicated T cell populations in peripheral blood of Healthy Donors (HDs). Mean fluorescent intensity (MFI) of CD226 expressed in the indicated T cell populations (gated on CD4$^+$CD45RA$^-$ T cells) (left panel) and mean±SEM of the CD226 MFI in the indicated T cell populations relative to the CD226 MFI of CD49b$^-$LAG-3$^-$ T cells obtained in 7 donors (right panel) are reported. P 0.005. FIG. 8B: Expression of CD25 in CD4$^+$CD45RA$^-$FOXP3$^+$ T cells and CD4$^+$CD45RA$^-$CD49b$^+$LAG-3$^+$ T cells and of FOXP3 in CD4$^+$CD45RA$^-$CD25$^{bright}$ and CD4$^+$CD45RA$^-$CD49b$^+$LAG-3$^+$ T cells. One representative donor out of 4 is shown; numbers in histograms indicate MFI (gated on CD4$^+$CD45RA$^-$FOXP3$^+$ or CD4$^+$CD25$^{bright}$ T cells in blue, and on CD4$^+$CD45RA$^-$CD49b$^+$LAG-3$^+$ T cells in red). Expression of FOXP3 (normalized to HPRT) measured by RT-PCR in the indicated FACS-sorted T cell populations from peripheral blood of HDs. One representative donor out of 3 to 5 and mean±SEM of 3-5 independent donors is shown. P 0.005. When not indicated differences were not statistically different. FIG. 8C: IL-10/IL-4 ratio in the indicated FACS-sorted T cell populations activated with immobilized anti-CD3 and soluble anti-CD28 mAbs for 72 h are shown. Three out of 9 donors tested.

FIG. 9, comprising FIG. 9A: Expression of CD226. MFI of CD226 expressed by the indicated T cell populations (gated on CD4$^+$TCRβ$^+$Foxp3$^{RFP-}$ T cells) analyzed 4 h after the second anti-CD3 mAb injection (upper panel) and MFI of CD226 expressed in the indicated T cell populations (gated on CD4+TCRβ$^+$Foxp3$^{RFP-}$ T cells) relative to the expression of CD4$^+$CD49b$^-$LAG-3$^-$ T cells (lower panel) is shown. *P 0.05. When not indicated differences were not statistically different. FIG. 9B: Frequency of the indicated T cell populations (gated on CD4$^+$TCRβ$^+$Foxp3$^{RFP-}$ T cells) at 4 h (52), 48 h (100) and 96 h (144) after the second anti-CD3 mAb injection. FIG. 9C: Expression of the Il10, Il4, Ifng, Il17a, Il2, Tnfa (normalized to Hprt) measured by RT-PCR in the indicated FACS-sorted T cell populations from the small intestine of anti-CD3 treated mice. As controls, T$_H$1 (CD4$^+$TCRβ$^+$IFN-γ$^{Katushka+}$), T$_H$17 (CD4$^+$TCRβ$^+$IL-17A$^{eGFP+}$) and Foxp3$^+$ Treg (CD4$^+$TCRβ$^+$Foxp3$^{RFP+}$) cells isolated from the small intestine of Foxp3$^{RFP}$IFN-γ$^{Katushka}$ and Foxp3$^{RFP}$IL-17A$^{eGFP}$ reporter mice injected with anti-CD3 mAb were used. Mean±SEM of 3 independent experiments. *P 0.05, P 0.005, and *P 0.0005 vs. CD4+CD49b+LAG-3+ T cells. When not indicated differences were not statistically different. FIG. 9D: The indicated FACS-sorted T cell populations from the small intestine of anti-CD3 treated mice re-stimulated in vitro with anti-CD3 and anti-CD28 mAbs for 72 h were tested for cytokine production. Mean±SEM of IL-2 and TNF-α and the ratios of IL-10 vs. IL-2 and TNF-α are presented. One representative experiment out of 3. In each experiment cells isolated from 5 mice were pooled before FACS-sorting. *p 0.05. When not indicated differences were not statistically different.

FIG. 12A through FIG. 12C, depicts the results of experiments demonstrating that the in vivo regulatory activity of murine CD4$^+$CD49b$^+$LAG-3$^+$ T cells is IL-10 dependent. FIG. 12A: eT$_H$17 (CD4+TCRβ+Foxp3$^{RFP}$-IL-17A$^{eGFP+}$) and Dominant Negative IL-10R-eT$_H$17 (DNR eTH17) cells were isolated from the colon and mesenteric lymph nodes of RAG1$^{-/-}$ mice injected with CD4$^+$CD45RB$^{High}$ T cells isolated from either Foxp3$^{RFP}$IL-17A$^{eGFP}$ or Dominant Negative IL-10R-Foxp3$^{RFP}$IL-17A$^{eGFP}$ double reporter mice. FACS-sorted CD4$^+$TCRβ$^+$Foxp3$^{RFP}$-CD49b$^+$LAG-3$^+$ T cells from the small intestine of anti-CD3 treated mice were transferred i.p. in combination with eT$_H$17 cells, or with DNR eT$_H$17 (ratio 1:1) into RAG1$^{-/-}$ mice. Endoscopic colitis score (FIG. 12B) and change in body weight (FIG. 12C) were measured. Each dot represents one mouse. Lines indicate mean±SEM. *P 0.05, **P 0.005.

FIG. 13, comprising FIG. 13A: Expression of LAG-3 and CD49b measured on CD4$^+$TCRβ$^+$Foxp3$^{RFP-}$ in cells isolated from the spleen of anti-CD3 treated mice (upper panel) and frequencies of CD4$^+$IL-10$^{eGFP+}$ T cells (gated on CD4+TCRβ+Foxp3$^{RFP-}$) in the indicated T cell populations (lower panel) are shown. Representative dot plots from 1 experiment out of 5 are shown. In each experiment cells isolated from 2 to 5 mice were pooled. Percentages of cells in each quadrant are indicated. MFI for IL-10$^{eGFP+}$ T cells in the indicated T cell populations (right panel) are shown. FIG. 13B: Mean±SEM of IL-10$^{eGFP+}$ cell frequencies among the indicated T cell populations obtained in 3 independent experiments is shown. In each experiment 2 to 5 mice were pooled. ***P 0.0005. FIG. 13C: The indicated FACS-sorted T cell populations (gated on CD4$^+$TCRβ$^+$Foxp3$^{RFP-}$) from the spleen of anti-CD3 treated mice were re-stimulated in vitro with anti-CD3 and anti-CD28 mAbs for cytokine production. Mean±SEM of IL-10, IFN-γ, IL-17A, IL-2, IL-4 is shown. One representative experiment out of 3 is shown. In each experiment cells isolated from 2 to 5 mice were pooled before the FACS-sorting. Each experiment contains at least 2 sample replicates for each population. *P 0.05 and **P 0.005. When not indicated differences were not statistically different. FIG. 13D: The indicate FACS-sorted T cell populations (gated on CD4$^+$TCRβ$^+$Foxp3$^{RFP-}$) from the spleen of anti-CD3 treated mice were tested in suppressive assay in the presence or absence of anti-IL-10R mAbs. Percentages of suppression mediated by the indicated T cell populations are reported. *P 0.05, **P 0.005.

FIG. 14, comprising FIG. 14A through FIG. 14E, depicts the results of experiments demonstrating that murine CD4$^+$CD49b$^+$LAG-3$^+$ T cells can be isolated from N. brasiliensis infected mice. FIG. 14A: Numbers of total cells infiltrating the lungs at different time points during the infection are shown (Mean±SEM). Mice per time points: day 0, n=7; day 5, n=4; day 7, n=5; day 10, n=7; day 16, n=5. FIG. 14B: Frequencies of Ly6G cells among CD45$^+$ cells infiltrating the lung at different time points during the infection are shown (Mean±SEM). Mice per time points: day 0, n=3; day 5, n=3; day 7, n=3; day 10, n=3; day 16, n=3. FIG. 14C: Expression of CD49b and LAG-3 measured on CD4$^+$TCRβ$^+$ IL-4$^{eGFP+}$ (T$_H$2); CD4$^+$TCRβ$^+$Foxp3$^{RFP}$-IL-17A$^{eGFP+}$ (T$_H$17), CD4$^+$TCRβ$^+$Foxp3$^{RFP+}$IL-17$^{eGFP}$-(Foxp3$^+$ Tregs), and CD4$^+$TCRβ$^+$Foxp3$^{RFP}$-IFN-10$^{eGFP+}$ (Tr1) cells isolated from the lungs of IL-4$^{eGFP}$, Foxp3$^{RFP}$ IL-17$^{eGFP}$, Foxp3$^{RFP}$ IL-10$^{eGFP}$ reporter mice infected with N. brasiliensis. For T$_H$2 and T$_H$17 cells, representative dot plots from 1 experiment out of 3 are shown. For Foxp3$^+$ Tregs cells representative dot plots from 1 experiment out of 4 are shown. For Tr1 cells representative dot plots from 1 experiment out of 4 are shown. Percentages of cells in each quadrant are indicated. FIG. 14D: Expression of CD49b and LAG-3 on CD4$^+$TCRβ$^+$Foxp3$^{RFP}$-IL-17A$^{eGFP+}$ (eT$_H$17) and on CD4$^+$TCRβ$^+$Foxp3$^{RFP}$-IFN-γ$^{Katushka+}$ (eT$_H$1) cells isolated from inflamed colon of RAG1–/– mice transferred with CD4$^+$CD45RB$^{High}$ T cells isolated either from Foxp3$^{RFP}$IL-17A$^{eGFP}$ cells or Foxp3$^{RFP}$IFN-γ$^{Katushka}$ double reporter mice. Percentages of cells in each quadrant are indicated. Representative dot plots from 1 experiment out of 3 are shown. FIG. 14E: Mean±SEM of frequencies of the indicated T cell populations obtained in 3-4 independent experiments is shown. In each experiment 2 to 5 mice were pooled. ***P 0.0005. When not indicated differences were not statistically different.

FIG. 15, comprising FIG. 15A through FIG. 15C, depicts the results of experiments demonstrating that murine CD4$^+$CD49b$^+$LAG-3$^+$ T cells isolated from N. brasiliensis infected mice expressed high levels of IL-10 and AhR. FIG. 15A: Expression of Il10, Il4, Il13, Gata3, Ahr (relative to Hrpt) measured by RT-PCR in the indicated T cell populations isolated from IL-4$^{eGFP}$ and Foxp3$^{RFP}$IL-10$^{eGFP}$ reporter mice infected with N. brasiliensis. As control CD4$^+$TCRβ+IL-4$^{eGFP+}$ (T$_H$2) and CD4$^+$TCRβ$^+$Foxp3$^{RFP+}$ (Tregs) isolated from the lung were used. Mean±SEM of 3 independent experiments is shown. *P 0.05, P 0.005 and *P 0.0005 vs. CD4+CD49b+LAG-3+ T cells. When not indicated differences were not statistically different. Frequencies of the indicated T cell populations (gated on CD4$^+$TCRβ$^+$Foxp3$^{RFP-}$ T cells) accumulated in the lungs (FIG. 15B) and in the mediastinal lymph nodes (FIG. 15C) at different time points after the N. brasiliensis infection of wild type mice. Mean±SEM is shown. In each time point 2 to 5 mice were tested.

FIG. 16, comprising FIG. 16A: Expression of the indicated genes (normalized to Hprt) in in vitro differentiated T$_H$0, iTregs, T$_H$2, T$_H$17, T$_H$1, and Tr1 cells measured by RT-PCR. T$_H$0 cells were used as internal control and the expression of each gene in each T cell is normalized to $T_H0$ cells. Mean±SEM of triplicates are shown. *P 0.0005. When not indicated differences were not statistically different. FIG. 16B: Expression of CD49b and LAG-3 in the indicated T cells differentiated in vitro after 4 days of culture is shown. Percentages of cells in each quadrant are indicated. Representative dot plots from 1 experiment out of 3 are shown. FIG. 16C: Mean±SEM of the frequencies of cells co-expressing CD49b and LAG-3 among the indicated T cell populations (n=3 for each group) is shown. * P 0.0005.

FIG. 17, comprising FIG. 17A: After 5 days CD4$^+$CD49b$^+$LAG-3$^+$ IL-10$^+$ Tr1 cells were FACS sorted and activated in the presence of anti-CD3 and anti-CD28 mAbs (upper panel) or anti-CD3, anti-CD28, TGF-β, IL-6 and IL-23 (lower panel). The expression of IL-10$^{eGFP}$ and CD49b/LAG-3 was analyzed at the indicated time points by FACS. FIG. 17B: Sorted Tr1 cells were cultured for 4 days in the presence of anti-CD3, anti-CD28, TGF-β, IL-6 and IL-23. The expression of IL-10 among CD49b$^+$LAG-3$^+$ and CD49b$^-$LAG-3$^{+/-}$is reported.

FIG. 18, comprising FIG. 18A through FIG. 18C, depicts the results of experiments demonstrating that upon transfer in vivo, CD49b and LAG-3 are expressed on in vitro generated Tr1 cells. CD4$^+$ T cells were isolated from the spleen of wild type mice and in vitro differentiated in Tr1 cells with IL-27 and TGF-β. After 5 days CD4$^+$CD49b$^+$LAG-3$^+$IL-10$^+$ Tr1 cells were FACS sorted transferred into RAG-1$^{-/-}$ mice. FIG. 18A: Each mouse was injected i.p. with 10$^5$ Tr1 cells and treated as depicted in the cartoon. FIG. 18B-C: The frequency of the indicated populations was analyzed at the indicated time points by FACS.

FIG. 19, comprising FIG. 19A: Expression of CD49b and LAG-3 in pTr1 and $T_H0$ cell lines. Dot plots from 1 representative donor out of 7 donors tested is presented. Percentages of cells in each quadrant are indicated. FIG. 19B: CD49b$^+$LAG-3$^+$ T cells were FACS-sorted from pTr1(DC-10) cells and were tested for their ability to suppress T cells activated with mDC (responder cells, filled histogram). pTr1(DC-10) cells and CD49b$^+$LAG-3$^+$ T cells sorted from pTr1(DC-10) cells (CD49b$^+$LAG-3$^+$ pTr1(DC-10)) were used to suppress the proliferation of autologous CD4+ T cells activated with mDC. As control, T(mDC) cells were used. Percentages of suppression are indicated. One representative experiment out of 3 is shown.

FIG. 20, comprising

DETAILED DESCRIPTION

Figure 1A:
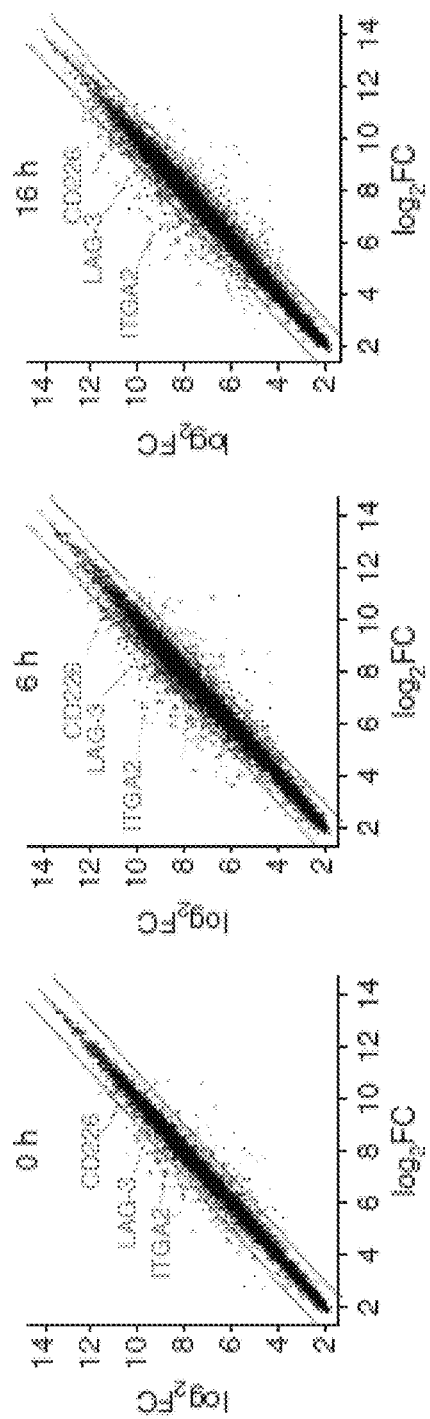
FIG. 1A through FIG. 1D, depicts the results of experiments demonstrating the identification of CD49b, LAG-3 and CD226 by gene expression profile of human Tr1 cell clones. Tr1 and $T_H0$ cell clones were isolated from peripheral blood of 2 Healthy Donors (HDs). mRNA from T cell clones unstimulated (t0, n=4 Tr1 cell clones and n=10 $T_H0$ cell clones) or stimulated with immobilized anti-CD3 and soluble anti-CD28 mAbs (6 h and 16 h, n=4 Tr1 cell clones and n=5 $T_H0$ cell clones) was isolated. Differential expression of 28869 genes was investigated by whole transcript Affymetric chips.

The present invention is based upon the discovery that T regulatory type 1 (Tr1) cells express particular cell surface markers that allow for their selection, enrichment, isolation, purification and administration. The ability to use the particular markers described herein to select, enrich, isolate, purify and administer Tr1 cells allows for improved methods of Tr1 therapies for treating a wide variety of diseases and disorders.

The invention includes methods of administering Tr1 cells to a subject in need thereof, to treat or prevent a disease or disorder involving an undesired immune response. Exemplary diseases and disorders that are treatable or preventable with the Tr1 cell compositions and methods of the invention include, but are not limited to, inflammatory diseases and disorders, autoimmune diseases or disorders, and disorders associated with transplantation, such as transplant rejection and graft versus host disease.

In certain embodiments, the methods of the invention comprise isolating T cells which express one or more Tr1 selective markers. In one embodiment, the method comprises selecting T cells which express one or more Tr1 marker selected from the group consisting of CD49b, LAG-3, and CD226 (DNAM-1). In some embodiments, the method comprises selecting T cells that co-express CD49b and LAG-3. In other embodiments, the method comprises selecting T cells that co-express CD49b, LAG-3, and CD226. In some embodiments, the Tr1 cells do not constitutively express high levels of Foxp3, as compared with the level of Foxp3 on a comparator cell selected from the group consisting of a CD25bright T cell and a Foxp3+ Treg cell. In some embodiments, the Tr1 cells exhibit IL-10 dependent regulatory activity.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, to "alleviate" a disease means reducing the severity of one or more symptoms of the disease.

"Allogeneic" refers to a graft derived from a different animal of the same species.

"Alloantigen" is an antigen that differs from an antigen expressed by the recipient.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab).sub.2, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" (APC) is a cell that is capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

As used herein, the term "autologous" is meant to refer to any material derived from the same individual to which it is later to be re-introduced into the mammal.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "DNA" as used herein is defined as deoxyribonucleic acid.

"Donor antigen" refers to an antigen expressed by the donor tissue to be transplanted into the recipient.

"Recipient antigen" refers to an antigen expressed by the recipient.

As used herein, an "effector cell" refers to a cell which mediates an immune response against an antigen. An example of an effector cell includes, but is not limited to a T cell and a B cell.

As used herein, the term "immune response" includes T cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Mixed lymphocyte reaction," "mixed lymphocyte culture," "MLR," and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes, including for example, Tr1 cells. A frequent objective of an MLC is to provide allogeneic stimulation, such as may initiate proliferation of the Tr1 cells; but unless indicated, proliferation during the culture is not required. In the proper context, these terms may alternatively refer to a mixture of cells derived from such a culture.

As used herein "endogenous" refers to any material from or produced inside an organism, cell, tissue or system.

By the term "effective amount," as used herein, is meant an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

As used herein, the term "exogenous" refers to any material introduced from or produced outside an organism, cell, tissue or system.

The term "epitope" as used herein is a portion of an antigen that can elicit an immune response, including B and/or T cell responses. An antigen can have one or more epitopes. Most antigens have many epitopes; i.e., they are multivalent. In some examples, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that in some circumstances, the three-dimensional structure, rather than the specific linear sequence of the molecule, is the main criterion of antigenic specificity and therefore distinguishes one epitope from another.

The term "expression" as used herein is defined as the transcription and/or translation of a nucleotide sequence.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "helper T cell" as used herein is defined as an effector T cell whose primary function is to promote the activation and functions of other B and T lymphocytes and or macrophages. Many helper T cells are CD4 T-cells.

The term "heterologous" as used herein is defined as DNA or RNA sequences or proteins that are derived from the different species.

As used herein, "homology" is used synonymously with "identity."

The term "immunoglobulin" or "Ig," as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immunostimulatory" is used herein to refer to increasing at least one parameter of an immune response.

The term "immunosuppressive" is used herein to refer to reducing at least one parameter of an immune response.

"Tr1 differentiation" as used herein refers to any event which results in a detectable increase in the phenotype and/or genotype characteristic of Tr1 cells. For example, a phenotype and/or genotype characteristic of Tr1 cells is the co-expression of CD49b and LAG-3. Another phenotype and/or genotype characteristic of Tr1 cells is immunosuppression.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

The term "polypeptide" as used herein is defined as a chain of amino acid residues, usually having a defined sequence. As used herein the term polypeptide is mutually inclusive of the terms "peptide" and "protein."

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, "specifically binds" refers to the fact that a first compound binds preferentially with a second compound and does not bind in a significant amount to other compounds present in the sample.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances. In some examples, the first substance is a particular type of cell identifiable by is expression of cell surface markers.

A "population" is used herein to refer to a group of cells having a substantially similar phenotypic characteristic.

"Transplant" refers to a donor tissue, organ or cell, to be transplanted. An example of a transplant may include but is not limited to skin cells or tissue, hematopoietic cells, bone marrow, and solid organs such as heart, pancreas, kidney, lung and liver.

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

As used herein, a "therapeutically effective amount" is the amount of a therapeutic composition sufficient to provide a beneficial effect to a mammal to which the composition is administered.

As used herein, "treating" refers to the reduction, alleviation or elimination, of at least one sign or symptom of a disease or disorder which is being treated, e.g. alleviation of immune dysfunction or avoidance of transplant rejection, relative to the symptoms prior to treatment. As used herein "treating" or "treatment" includes both therapeutic and prophylactic treatments.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based upon the finding that T regulatory type 1 (Tr1) cells express specific cell surface markers that allow for their selection, enrichment, isolation, and purification. While certain methods of generating Tr1 cells are known in the art, there has, until now, yet to be a method of producing an enriched population of Tr1 cells for use in research and clinical therapeutic methods. The ability to use the specific markers described herein to select, enrich, isolate, and purify Tr1 cells allows for improved methods of Tr1 therapies for treating a wide variety of diseases and disorders. For example, it is demonstrated herein that Tr1 cells selected, enriched, isolated, and purified by the methods of the invention exhibit immunosuppressive activities both in vitro and in vivo.

The invention includes methods of administering Tr1 cells to a subject in need thereof, to treat or prevent a disease or disorder involving an undesired immune response. Exemplary diseases and disorders that are treatable or preventable with the Tr1 cell compositions and methods of the invention include, but are not limited to, inflammatory diseases and disorders, autoimmune diseases or disorders, and disorders associated with transplantation, such as transplant rejection and graft versus host disease. Examples of autoimmune and inflammatory diseases and disorders treatable or preventable with the Tr1 cell compositions and methods of the invention include, but are not limited to, acute and chronic diseases and disorders such as allergy, asthma, inflammatory bowel disease, autoimmune entheropathy, Addison's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis. In certain embodiments, the Tr1 cell compositions and methods of the invention are used to treat subjects who have received a transplant, such as a hematopoietic cell transplant, a stem cell transplant, a bone marrow transplant, cord blood transplant, an organ and cell transplant, a blood transfusion, and the like.

In certain embodiments, the methods of the invention comprise selecting T cells which express one or more Tr1 selective markers. In one embodiment, the method comprises selecting T cells which express one or more Tr1 marker selected from the group consisting of CD49b, LAG-3, and CD226 (DNAM-1). In some embodiments, the method comprises selecting T cells that co-express CD49b and LAG-3. In other embodiments, the method comprises selecting T cells that co-express CD49b, LAG-3, and CD226. In some embodiments, the method comprises selected T cells that express CD49b, LAG-3, and an elevated level of CD226, as compared with the level of CD226 on a comparator cell population, such as CD49b-LAG-3⁻ T cells, or $T_H0$ cells. In some embodiments, the Tr1 cells do not constitutively express high levels of Foxp3, as compared with the level of Foxp3 on a comparator cell selected from the group consisting of a CD25bright T cell and a Foxp3+ Treg cell. In some embodiments, the Tr1 cells exhibit IL-10 dependent regulatory activity. In certain embodiments, the method comprises selecting T cells which express one or more Tr1 markers after the T cells are activated.

In one embodiment, the invention comprises detecting the level of Tr1 cells in a subject by detecting the absolute number, or the relative amount, of T cells which express Tr1 markers in a sample obtained from the subject. In one embodiment, the method comprises detecting T cells which express one or more Tr1 markers selected from the group consisting of CD49b, LAG-3, and CD226. In some embodiments, the Tr1 cells do not constitutively express high levels of Foxp3, as compared with the level of Foxp3 on a comparator cell selected from the group consisting of a CD25bright T cell and a Foxp3+ Treg cell. In some embodiments, the Tr1 cells exhibit IL-10 dependent regulatory activity. The method can be used to determine if the subject is tolerized or tolerant to a transplantation therapy, including, but not limited to a hematopoietic cell transplantation, such as a hematopoietic stem cell transplantation (HSCT). In one embodiment, the method can be used to monitor the absolute number or relative amount of Tr1 cells in a subject over time, thereby allowing for the prediction of the risk of an adverse immune response.

Tr1 Cell Differentiation

The invention includes methods of and compositions for converting or differentiating non-regulatory T cells into Tr1 cells. In one embodiment, the method comprises converting non-regulatory T cells into Tr1 cells that express at least one marker selected from the group consisting of CD49b, LAG-3, and CD226 (DNAM-1). In some embodiments, the method comprises converting non-regulatory T cells into Tr1 cells that co-express CD49b and LAG-3. In other embodiments, the method comprises converting non-regulatory T cells into Tr1 cells that co-express CD49b, LAG-3, and CD226. The method comprises converting non-regulatory T cells into Tr1 cells that do not constitutively express high levels of Foxp3, as compared with the level of Foxp3 on a comparator cell selected from the group consisting of a CD25bright T cell and a Foxp3+ Treg cell. In some embodiments, the method comprises converting non-regulatory T cells into Tr1 cells that exhibit IL-10 dependent regulatory activity.

In some embodiments, the method of differentiating cells into Tr1 cells includes the step of obtaining non-regulatory T cells of a subject. In some embodiment, the non-regulatory T cells of the subject are CD4$^+$ T cells. In some embodiments, the non-regulatory T cells the subject are CD4$^+$ CD25$^-$ T cells. In some embodiments, the subject is a mammal, such as a human or a mouse. In some embodiments, the method of differentiating cells into Tr1 cells includes the step of culturing the non-regulatory T cells of the subject in the presence of feeder cells. In some embodiments, the feeder cells are L cells. In some embodiments, the feeder cells are transfected with at least one of CD32, CD80, and CD58. In some embodiments, the feeder cells are transfected with at least one of hCD32, hCD80, and hCD58. In some embodiments, the method of differentiating cells into Tr1 cells includes the step of culturing the non-regulatory T cells of the subject in the presence of anti-CD3 mAb. In some embodiments, the method of differentiating cells into Tr1 cells includes the step of culturing the non-regulatory T cells of the subject in the presence of IL-2, such as rhIL-2. In some embodiments, the method of differentiating cells into Tr1 cells includes the step of culturing the non-regulatory T cells of the subject in the presence of IL-15, such as rhIL-15. In some embodiments, the differentiated Tr1 cells are polarized. In some embodiments, the differentiated Tr1 cells are polarized by culturing the differentiated Tr1 cells in the presence of at least one of IL-10, such as rhIL-10, and IFNα-2b, such as rhIFNα-2b.

The invention also provides methods and compositions for ex vivo conversion and expansion of Tr1 cells from non-Tr1 cells. The expansion methods for Tr1 cells can include the use of a bead- or cell-based artificial antigen-presenting cell. However, any method in the art can be used to expand the Tr1.

The present invention provides a method of large-scale conversion and expansion of Tr1 that addresses the low numbers of natural Tr1 cells that can be isolated and expanded. Thus, the methods and compositions of the invention are useful for therapeutic purposes, for example, in the prevention and treatment of immune-based disorders and in the prevention and treatment of allograft rejection.

Tr1 Cell Isolation and Expansion

Tr1 cells suppress immune responses and play an important role in immunotherapy against inflammation and autoimmune disease and contribute to transplantation tolerance. Some in vivo uses require expansion processes to generate sufficient numbers of Tr1 cells for in vivo therapeutic use.

The present invention provides a method of generating an enriched population of immunosuppressive Tr1 cells from the abundant CD4$^+$ T cell population. The various embodiments, the majority of the cells of the enriched population of Tr1 cells express the cell surface markers CD4, and CD49b, and LAG-3. In some embodiments, greater than 90% the cells of the enriched population of Tr1 cells express the cell surface markers CD4, and CD49b, and LAG-3. In some embodiments, greater than 95% the cells of the enriched population of Tr1 cells express the cell surface markers CD4, and CD49b, and LAG-3. In some embodiments, greater than 98% the cells of the enriched population of Tr1 cells express the cell surface markers CD4, and CD49b, and LAG-3. In some embodiments, greater than 99% the cells of the enriched population of Tr1 cells express the cell surface markers CD4, and CD49b, and LAG-3. In some embodiments, greater than 99.5% the cells of the enriched population of Tr1 cells express the cell surface markers CD4, and CD49b, and LAG-3.

This method allows for the generation of Tr1 cells in sufficient numbers for in vivo infusions. The method can be used both for generating Tr1 cells for research purposes as well as for clinical use by administration to a subject in need thereof.

The present invention provides a method of generating a population of immunosuppressive Tr1 cells from the abundant CD4$^+$ T cell population. This method allows for the generation of Tr1 cells in sufficient numbers for in vivo infusions. The method can be used both for generating Tr1 cells for research purposes as well as for clinical use by administration to a subject in need thereof.

In some embodiments, the invention provides methods of selecting or isolating the cells so identified. In some embodiments, CD4$^+$ T cells are obtained from blood (e.g., isolated from PBMC), bone marrow, cord blood, lymphoid tissue, thymus, spleen, or any tissues/organ sample of interest, including, but not limited the pancreas, eye, heart, liver, nerves, intestine, skin, muscle, and joints.

The cells bearing the desired markers (e.g., CD49b and LAG-3) can be isolated, for instance, by the use of labeled antibodies or ligands with FACS or magnetic particles/bead technologies as known to one of ordinary skill in the art. Accordingly, in some embodiments, the invention provides a method of generating an enriched population of immunosuppressive Tr1 cells which are substantially CD4$^+$CD49b$^+$LAG-3$^+$ by obtaining a biological sample that also comprises non-Tr1 cells, including, but not limited to, CD4$^+$, CD4$^+$CD25$^-$, CD4$^+$CD25$^-$CD45RA$^+$ cells, and converting or differentiating the non-Tr1 cells into Tr1 cells.

To enhance the enrichment of Tr1 cells, positive selection for CD49b and/or LAG-3 may be combined with negative selection against cell surface makers specific to non-Tr1 cell types, including, by way of non-limiting examples, CD8, CD11b, CD16, CD19, CD36 and CD56.

Sources of T cells and methods of isolating particular T cell populations (e.g., CD4$^+$ cells) which can be converted or differentiated by culturing according to the methods of the present invention are well known and described in the literature. Thus for example T cells may conveniently be isolated from the blood e.g. from a peripheral blood mononuclear cell (PBMC) population isolated from blood, or from other blood-derived preparations such as leukopheresis products or from bone marrow, lymph, thymus, spleen or umbilical cord. T cell populations may be derived from any appropriate source, including human or animal sources.

The invention includes converting or differentiating non-Tr1 cells, or mixed populations of Tr1 cells and non-Tr1 cells, in the presence of a bead- or cell-based artificial antigen-presenting cell system. Regardless of the system used for cellular expansion, the cells can be expanded prior to, simultaneously with, and/or subsequent to Tr1 conversion. For example, the cells can be expanded using a beador cell-based artificial antigen-presenting cell system before the initial Tr1 conversion stage. Alternatively, the cells can be expanded using a bead- or cell-based artificial antigen-presenting cell system after the initial Tr1 conversion stage but before the selective outgrowth stage that favors proliferation of Tr1s. Alternatively, the cells can be expanded using a bead- or cell-based artificial antigen-presenting cell system after the outgrowth stage but before the imprinting stage. Alternatively, the cells can be expanded using a bead- or cell-based artificial antigen-presenting cell system after the imprinting state.

Special cell-sized beads (e.g., magnetic iron-dextran beads) can be used that are coated with antibodies, such as anti-CD3 and/or anti-CD28. The use of anti-CD3 and/or anti-CD28 beads induced robust proliferation of cells. As a non-limiting example, a 3:1 bead:T cell ratio expands and preserves Tr1 function at a desirable level. The ratios of antibodies to CD3 and/or CD28 can be adjusted for optimal results. The beads can easily be removed by passing the cultured cells through a magnetic column. As an added advantage, the culture-expanded Tr1 retain potent functional suppressor activity.

The culture-expanded Tr1 of the present invention are capable of suppressing an MLR, with, by way of example, primary $CD4^+$ cells or cultured $CD4^+CD25^-$ cells as responding T cells. In one embodiment the converted and expanded Tr1 cells inhibit the autologous proliferation of peripheral blood cells. In another embodiment, the converted and expanded Tr1 cells block or prevent GVHD, or inhibit or reverse the disease if already in progress. In yet another embodiment, the converted and expanded Tr1 cells are introduced into a different host; whereas in yet another embodiment, the Tr1 cells are established as a cell line for continuous therapeutic use. Preferably, the host is a human host and the culture-expanded Tr1 cells are human, although animals, including animal models for human disease states, are also included in this invention and therapeutic treatments of such animals are contemplated herein.

Following Tr1 conversion or differentiation using the methods of the invention, Tr1 cells can be expanded under appropriate conditions for growth of the Tr1 cells. Growth is allowed to progress for a time period selected according to the final number of T cells required and the rate of expansion of the cells. Passaging of the cells may be undertaken during this period. Such a time period is normally between 3 and 10 days but can be as long as 14 to 20 days or even longer providing the viability and continued proliferation of the T cells is maintained.

Therapeutic Application

The invention includes methods of administering Tr1 cells to a subject in need thereof, for the treatment or prevention of a disease or disorder, such as an inflammatory disease or disorder, an autoimmune disease or disorder, or transplantation rejection. The ex vivo culture-converted and culture-expanded Tr1 cells, with or without naturally occurring Tr1 cells, can be introduced to the host subject or to another subject by any number of approaches. In some embodiments, they are injected intravenously. Optionally, the host subject may be treated with agents to promote the in vivo function and survival of the Tr1 cells. Of course, the culture-expanded Tr1 may also be introduced in a variety of pharmaceutical formulations. These may contain such normally employed additives as binders, fillers, carriers, preservatives, stabilizing agents, emulsifiers, and buffers. Suitable diluents and excipients are, for example, water, saline, and dextrose, as utilized in the methods described herein. The administration of Tr1 cells to a subject before, during or after onset of the disease or disorder, serves to diminish the frequency or severity of the signs or symptoms of the disease or disorder experienced by the subject.

In various embodiments, the cells can be converted directly after harvest or the cells can be stored (e.g., by freezing) prior to their expansion, or the cells can be stored (e.g., by freezing) after expansion and prior to their therapeutic administration. In various embodiments, the Tr1 cells of the invention can be administered alone, or the Tr1 cells of the invention can be administered in combination with a known immunosuppressive therapy.

The methods of the invention thus provide for achieving an immunosuppressive effect in a subject, i.e., a method of preventing or diminishing an immune response. The disease or disorder typified by an aberrant immune response may be an inflammatory or autoimmune disease or disorder, such as allergy, asthma, inflammatory bowel disease, autoimmune entheropathy, Addison's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis.

In certain embodiments, the Tr1 cell compositions and methods of the invention are used to prevent or treat with an inflammatory disease or disorder, or an autoimmune disease or disorder, in a subject in need thereof. Non-limiting examples of inflammatory and autoimmune diseases and disorders preventable or treatable with the compositions and methods of the invention, include but are not limited to, allergy, asthma, inflammatory bowel disease, autoimmune entheropathy, Addison's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis.

In other embodiments, the Tr1 cell compositions and methods of the invention are used to treat subjects who have received a transplant, such as a hematopoietic cell transplant, a stem cell transplant, a bone marrow transplant, an organ or cell transplant, a blood transfusion, and the like. Conditions in which immune suppression would be advantageous include conditions in which a normal or an activated immune response is disadvantageous to the mammal, e.g. allotransplantation of cells or tissues, to avoid rejection, or in fertility treatments in which inappropriate immune responses have been implicated in failure to conceive and miscarriage. The use of such cells before, during, or after transplantation avoids extensive chronic graft versus host disease which may occur in post-transplant patients. The cells may be converted immediately after harvest or stored (e.g., by freezing) prior to expansion or after expansion and prior to their therapeutic use. The therapies may be conducted in conjunction with known immunosuppressive therapies.

The methods of the present invention are particularly useful for humans, but may also be practiced on veterinary subjects. An "individual," "subject," "patient" or "host" referred to herein is a vertebrate, preferably a mammal. More preferably, such individual is a human and the culture-expanded cells are human, although animals, including animal models for human disease states, are also included in this invention and therapeutic treatments of such animals are contemplated herein. Such animal models can be used to test and adjust the compositions and methods of this invention, if desired. Certain models involve injecting in-bred animals with established cell populations. Also useful are chimeric animal models, described in U.S. Pat. Nos. 5,663,481, 5,602,305 and 5,476,993; EP application 379,554; and International Appl. WO 91/01760. Non-human mammals include, but are not limited to, veterinary or farm animals, sport animals, and pets. Accordingly, as opposed to animal models, such animals may be undergoing selected therapeutic treatments.

The present invention encompasses a method of reducing and/or eliminating an immune response in a subject with an inflammatory or autoimmune disease or disorder by administering to the subject an amount of Tr1 cells effective to reduce or inhibit an immune response in the subject. The Tr1 cells can be administered to the subject, before, during, or after onset of the disease or disorder. Non-limiting examples of inflammatory and autoimmune diseases and disorders treatable with the compositions and methods of the invention, include but are not limited to, allergy, asthma, inflammatory bowel disease, autoimmune entheropathy, Addision's disease, alopecia areata, ankylosing spondylitis, autoimmune hepatitis, autoimmune parotitis, Crohn's disease, diabetes mellitus, dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis.

The present invention encompasses a method of reducing and/or eliminating an immune response to a transplant in a recipient by administering to the recipient of the transplant an amount of Tr1 cells effective to reduce or inhibit host rejection of the transplant. The Tr1 cells can be administered to the transplant patient, before transplant, during transplant, or after the transplant has occurred. Without wishing to be bound to any particular theory, the Tr1 cells that are administered to the recipient of the transplant inhibit the activation and proliferation of the recipient's T cells, or induce tolerance. The transplant can include a donor tissue, organ or cell. An example of a transplant may include but is not limited to skin cells or tissue, hematopoietic cells, bone marrow, pancreatic islets, and solid organs such as heart, pancreas, kidney, lung and liver.

In one embodiment, the method of the invention is a method of inhibiting a T cell mediated immune response, by contacting at least one T cell with an effective amount of CD4+CD49+LAG-3+Tr1 cells. In one embodiment, the T cell mediated immune response inhibited by the methods of the invention is an effector T cell activity. In another embodiment, the T cell mediated immune response inhibited by the methods of the invention is cytotoxic T-lymphocyte (CTL) activity.

In another embodiment, the method of the invention is a method of inhibiting at least one alloreactive T cell, by contacting the at least one alloreactive T cell with an effective amount of CD4+CD49+LAG-3+Tr1 cells.

In one embodiment, the method of the invention is a method of generating an immunomodulatory effect in a subject having an alloreactive response, inflammatory response, or autoimmune response, the method comprising administering to said subject an effective amount of CD4+CD49+LAG-3+Tr1 cells.

In another embodiment, the method of the invention is a method of preventing an alloreactive response, inflammatory response, or autoimmune response in a subject, said method comprising administering to the subject, prior to onset of the alloreactive response, inflammatory response, or autoimmune response, an effective amount of CD4+CD49+LAG-3+Tr1 cells to prevent the response.

Based upon the disclosure provided herein, Tr1 cells can be obtained from any source, for example, from the tissue donor, the transplant recipient or an otherwise unrelated source (a different individual or species altogether). The Tr1 cells may be autologous with respect to the T cells (obtained from the same host) or allogeneic with respect to the T cells. In the case where the Tr1 cells are allogeneic, the Tr1 cells may be autologous with respect to the transplant to which the T cells are responding to, or the Tr1 cells may be obtained from a mammal that is allogeneic with respect to both the source of the T cells and the source of the transplant to which the T cells are responding to. In addition, the Tr1 cells may be xenogeneic to the T cells (obtained from an animal of a different species), for example mouse Tr1 cells may be used to suppress activation and proliferation of human T cells.

Another aspect of the present invention encompasses the route of administering Tr1 cells to the subject. Tr1 cells can be administered by a route that is suitable under the circumstances. Tr1 cells can be administered systemically, i.e., parenterally, by intravenous injection or can be targeted to a particular tissue or organ, such as bone marrow. Tr1 can be administered via a subcutaneous implantation of cells or by injection of the cells into connective tissue, for example, muscle.

Tr1s cells can be suspended in an appropriate diluent, at a concentration of about $5 \times 10^6$ cells/ml. Suitable excipients for injection solutions are those that are biologically and physiologically compatible with the Tr1s and with the recipient, such as buffered saline solution or other suitable excipients. The composition for administration can be formulated, produced and stored according to standard methods complying with proper sterility and stability.

The dosage of the Tr1 cells varies within wide limits and may be adjusted to the subject's requirements in each particular case. The number of cells used depends on the weight and condition of the recipient, the number and/or frequency of administrations, and other variables known to those of skill in the art.

In various embodiments, between about $10^5$ and about $10^{13}$ Tr1 cells per 100 kg body weight can be administered to the subject. In some embodiments, between about $1.5 \times 10^6$ and about $1.5 \times 10^{12}$ cells are administered per 100 kg body weight. In some embodiments, between about $1 \times 10^9$ and about $5 \times 10^{11}$ cells are administered per 100 kg body weight. In some embodiments, between about $4 \times 10^9$ and about $2 \times 10^{11}$ cells are administered per 100 kg body weight. In some embodiments, between about $5 \times 10^8$ cells and about $1 \times 10^{10}$ cells are administered per 100 kg body weight.

In another embodiment of the present invention, Tr1 cells are administered to the recipient prior to, contemporaneously with, or after a transplant to reduce and/or eliminate host rejection of the transplant. While not wishing to be bound to any particular theory, Tr1s can be used to condition a recipient's immune system to the transplant by administering Tr1s to the recipient, prior to, at the same time as, or following transplantation of the transplant, in an amount effective to reduce, inhibit or eliminate an immune response against the transplant by the recipient's T cells. The Tr1 cells affect the T cells of the recipient such that the T cell response is reduced, inhibited or eliminated when presented with the transplant. Thus, host rejection of the transplant may be avoided, or the severity thereof reduced, by administering Tr1 cells to the recipient, prior to, at the same time as, or following transplantation.

In another embodiment of the present invention, Tr1 cells are administered to the patient prior to, contemporaneously with, or after the onset of inflammatory or autoimmune diseases to prevent and/or re-establish tolerance. While not wishing to be bound to any particular theory, Tr1s can be used to condition a patient's immune system by administering Tr1s to the patient, prior to, at the same time as, or following disease onset, in an amount effective to prevent, reduce, inhibit or eliminate an immune response by the patient's T cells. The Tr1 cells affect the T cells of the patients such that the T cell response is prevented, reduced, inhibited or eliminated.

Further, the present invention comprises a method of treating a patient who is undergoing an adverse immune response to a transplant by administering Tr1 cells to the patient in an amount effective to reduce, inhibit or eliminate the immune response to the transplant, also known as host rejection of the transplant.

The present invention includes a method of using Tr1 cells as a therapy to inhibit graft versus host disease or graft rejection following transplantation. Accordingly, the present invention encompasses a method of contacting a donor transplant, for example a donor tissue, organ or cell, with Tr1 cells prior to, during, or after transplantation of the transplant into a recipient. The Tr1 cells serve to ameliorate, inhibit or reduce an adverse response by the donor transplant against the recipient.

As discussed elsewhere herein, Tr1 cells can be obtained from any source, for example, from the tissue donor, the transplant recipient or an otherwise unrelated source (a different individual or species altogether) for the use of eliminating or reducing an unwanted immune response by a transplant against a recipient of the transplant. Accordingly, Tr1 cells can be autologous, allogeneic or xenogeneic to the tissue donor, the transplant recipient or an otherwise unrelated source.

In an embodiment of the present invention, the transplant is exposed to Tr1 cells prior, at the same time, or after transplantation of the transplant into the recipient. In this situation, an immune response against the transplant caused by any alloreactive recipient cells would be suppressed by the Tr1 cells present in the transplant. The Tr1 cells are allogeneic to the recipient and may be derived from the donor or from a source other than the donor or recipient. In some cases, Tr1 cells autologous to the recipient may be used to suppress an immune response against the transplant. In another case, the Tr1 cells may be xenogeneic to the recipient, for example mouse or rat Tr1 cells can be used to suppress an immune response in a human. However, it is preferable to use human Tr1 cells in the present invention.

In another embodiment of the present invention, the donor transplant can be "preconditioned" or "pretreated" by contacting the transplant prior to transplantation into the recipient with Tr1 cells in order to reduce the immunogenicity of the transplant against the recipient, thereby reducing and/or preventing graft versus host disease or graft rejection. For example, the transplant can be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant is then further contacted with Tr1 cells in order to reduce, inhibit or eliminate the activity of the T cells that were activated by the treatment of the cells or tissue from the recipient. Following this treatment of the transplant with Tr1 cells, the Tr1 cells may be removed from the transplant prior to transplantation into the recipient. However, some Tr1 cells may adhere to the transplant, and therefore, may be introduced to the recipient with the transplant. In this situation, the Tr1 cells introduced into the recipient can suppress an immune response against the recipient caused by any cell associated with the transplant. Without wishing to be bound to any particular theory, the treatment of the transplant with Tr1 cells prior to transplantation of the transplant into the recipient serves to reduce, inhibit or eliminate the activity of the activated T cells, thereby preventing restimulation, or inducing hyporesponsiveness of the T cells to subsequent antigenic stimulation from a tissue and/or cells from the recipient. One skilled in the art would understand based upon the present disclosure, that preconditioning or pretreatment of the transplant prior to transplantation may reduce or eliminate the graft versus host response.

In the context of umbilical cord blood, bone marrow or peripheral blood stem cell (hematopoietic stem cell) transplantation, attack of the host by the graft can be reduced, inhibited or eliminated by preconditioning the donor marrow by using the pretreatment methods disclosed herein in order to reduce the immunogenicity of the graft against the recipient. As described elsewhere herein, a donor hematopoietic stem and progenitor cell source can be pretreated with Tr1 cells from any source, preferably with recipient Tr1 cells in vitro prior to the transplantation of the donor marrow into the recipient. In a preferred embodiment, the donor marrow is first exposed to recipient tissue or cells and then treated with Tr1 cells. Although not wishing to be bound to any particular theory, it is believed that the initial contact of the donor hematopoietic stein and progenitor cell source with recipient tissue or cells function to activate the T cells in the donor marrow. Treatment of the donor marrow with the Tr1 cells induces hyporesponsiveness or prevents restimulation of T cells to subsequent antigenic stimulation, thereby reducing, inhibiting or eliminating an adverse effect induced by the donor marrow on the recipient.

In an embodiment of the present invention, a transplant recipient suffering from graft versus host disease or graft rejection may be treated by administering Tr1 cells to the recipient to reduce, inhibit or eliminate the graft versus host disease wherein the Tr1 cells are administered in an amount effective to reduce or eliminate graft versus host disease.

In an embodiment of the invention, the recipient's Tr1 cells may be obtained from the recipient prior to the transplantation and may be stored and/or expanded in culture to provide a reserve of Tr1 cells in sufficient amounts for treating an ongoing graft versus host reaction. However, as discussed elsewhere herein, Tr1 cells can be obtained from any source, for example, from the tissue donor, the transplant recipient or an otherwise unrelated source (a different individual or species altogether).

The skilled artisan will understand that the compositions and methods described herein can be used in conjunction with current therapeutic approaches for treating the diseases and disorders described elsewhere herein. By way of non-limiting example, the Tr1 cells of the present invention can be used in conjunction with the use of immunosuppressive drug therapy. An advantage of using Tr1 cells in conjunction with immunosuppressive drugs is that by using the methods of the present invention to ameliorate the severity of the immune response in a subject, such as a transplant recipient, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

It is also contemplated that the Tr1 cells of the present invention may be administered into a recipient repeatedly or as a "one-time" therapy for the prevention or treatment of a disease or disorder, such as an autoimmune disease or disorder, an inflammatory disease or disorder, or a disease or disorder associated with transplant, such as host rejection of donor tissue or graft versus host disease. A one-time administration of Tr1 cells into the recipient of the transplant eliminates the need for chronic immunosuppressive drug therapy. However, if desired, multiple administrations of Tr1 cells may also be employed.

The invention described herein also encompasses a method of preventing or treating transplant rejection and/or graft versus host disease by administering Tr1 cells in a prophylactic or therapeutically effective amount for the prevention, treatment or amelioration of host rejection of the transplant and/or graft versus host disease. Based upon the present disclosure, a therapeutic effective amount of Tr1 cells is an amount that inhibits or decreases the number of activated T cells, when compared with the number of activated T cells in the absence of the administration of Tr1 cells. In the situation of host rejection of the transplant, an effective amount of Tr1 cells is an amount that inhibits or decreases the number of activated T cells in the recipient of the transplant when compared with the number of activated T cells in the recipient prior to administration of the Tr1 cells.

An effective amount of Tr1 cells can be determined by comparing the number of activated T cells in a subject with a disease or disorder prior to the administration of Tr1 cells thereto, with the number of activated T cells present in the subject following the administration of Tr1 cells thereto. A decrease, or the absence of an increase, in the number of activated T cells in the subject, or in the transplant itself, that is associated with the administration of Tr1 cells thereto, indicates that the number of Tr1 cells administered is a therapeutic effective amount of Tr1s.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Co-Expression of CD49b and LAG-3 Identifies Human and Murine Tr1 Cells

CD4$^+$ T regulatory type 1 (Tr1) cells are induced in the periphery and play a pivotal role in promoting and maintaining tolerance. The absence of surface markers that uniquely identify Tr1 cells has limited their study and their clinical application. The studies presented herein demonstrate that by gene expression profiling of human Tr1 cell clones, the surface markers CD49b and LAG-3, which are stably and selectively co-expressed on murine and human Tr1 cells, were identified. As described herein, the specificity of these markers is proven in two mouse models of inflammation and in peripheral blood of healthy volunteers. The co-expression of CD49b and LAG-3 enables the isolation of highly suppressive human Tr1 cells from in vitro anergized cultures and, enables tracking Tr1 cells in the peripheral blood of tolerant subjects. As well as being an important finding for the biology of Tr1 cells, the identification of these markers makes Tr1 cells an even more attractive tool for therapeutic interventions.

The materials and methods employed in these experiments are now described.

Mice

C57BL/6 mice (B6), C57BL/6, RAG1−/− mice, C57BL/6 CD45.1$^+$ and C57BL/6 IL-4$^{eGFP}$ (4get) mice were purchased from The Jackson Laboratories. Dominant Negative IL-10R mice (Pacciani et al., 2010, J Allergy Clin Immunol 125, 727-736), Foxp3 reporter mice (Wan and Flavell, 2005, Proc Natl Acad Sci USA 102, 5126-5131), IL-17A$^{eGFP}$ reporter mice (Esplugues et al., 2011, Nature 475, 514-518), IL-10$^{eGFP}$ reporter mice (Kamanaka et al., 2006, Immunity 25, 941-952) and IFN-γ$^{Katushka}$ reporter mice were crossed and generated. Age- and sex-matched littermates between 8 and 12 weeks of age were used.

Cell Isolation and Purification of Human Cells

Human peripheral blood from healthy donors (HDs) was obtained upon informed consent in accordance with local ethical committee approval (TIGET PERIBLOOD) and with the Helsinki Declaration. PBMC were isolated by centrifugation over Lymphoprep Ficoll gradients (Fresenius Kabi Norge A S, Halden, Norway). CD4$^+$ T lymphocytes were purified from PBMC by negative selection using the untouched CD4$^+$ T Cell Isolation Kit II (Miltenyi Biotech, Auburn, Calif.), according to manufacturer's instructions. Naïve CD4$^+$CD45RO$^-$ T lymphocytes were purified from CD4$^+$ T lymphocytes by CD45RO MicroBeads (Miltenyi Biotech). The proportion of CD4$^+$CD45RO$^-$ CD45RA$^+$ was consistently greater than 90%.

Isolation of Human T Cell Clones

T cell clones were obtained from CD4+ cells by limiting dilution at 0.3 cells/well in the presence of a feeder cell mixture and soluble anti-CD3 mAbs (1 µg/mL, OKT3, Jansen-Cilag, Raritan, N.J., USA), in X-vivo 15 medium (BioWhittaker, Verviers, Belgium) supplemented with 5% pooled human AB serum (BioWhittaker), 100 U/mL penicillin/streptomycin (BioWhittaker). At day 3, IL-2 (40 U/mL; Chiron, Italia, Milan, Italy) was added. T cell clones were re-stimulated every 14 days with feeder cell mixture and soluble anti-CD3 mAbs (1 µg/mL). Between stimulations with feeder cells, T cell clones were expanded with rhIL-2 (40 U/mL). Once the T cell clones had been established, rhIL-15 (5 ng/mL, R&D System, Minneapolis, Minn., USA) was added at every change of medium as a Tr1 cell growth factor (Serafini et al., 2009, Haematologica 94, 1415-1426; Bacchetta et al., 2002, Eur J Immunol 32, 2237-2245). The clones were classified based on the cytokine production profile (Romagnani, 1994, Annual review of immunology 12, 227-257). Tr1 cell clones were defined when the ratio between IL-10 and IL-4 was higher than 8, as previously described (Serafini et al., 2009, Haematologica 94, 1415-1426; Bacchetta et al., 2002, Eur J Immunol 32, 2237-2245). All T cell clones were tested in a suppression assay to assess their regulatory activity.

T Cell Line Differentiation

Human T Cells

Human Tr1 and $T_H0$ cell lines were differentiated using murine L cells transfected with hCD32, hCD80, and hCD58 and supplemented with anti-CD3 mAb (100 ng/ml; OKT3, Jansen-Cilag, Raritan, N.J., USA) (artificial APCs), as previously described (Levings et al., 2001, J Immunol 166, 5530-5539). Briefly, CD4+CD45RO− T cells were activated by previously plated irradiated (7000 rad) L cells in X-vivo 15 medium (BioWhittaker) supplemented with 5% pooled human AB serum (BioWhittaker), 100 U/mL penicillin/streptomycin (BioWhittaker). $T_H0$ cell lines were differentiated in the presence of rhIL-2 (100 U/ml; Chiron Italia) and rhIL-15 (1 ng/ml; R&D Systems, Minneapolis, Minn., USA), whereas Tr1 cells were polarized with rhIL-10 (100 U/ml; BD Pharmingen), and rhIFNα-2b (5 ng/ml; IntronA, Schering Plough Europe, Bruxelles, Belgium). After 7 days, T cells were re-stimulated under identical conditions for additional 7 days. At the end of the 14 days of culture, T cells were washed, counted, and analyzed for cytokine production. IL-10-producing T cells were purified by IL-10-secretion assay (Miltenyi Biotech), according to the manufacturer's instruction.

DC-10 was differentiated as previously described (Gregori et al., 2010, Blood 116, 935-944). Briefly, CD14+ monocytes were isolated as the adherent fraction of PBMC following incubation for 1 hour in RPMI 1640 (Biowhittaker) supplemented with 10% FCS (Biowhittaker), 100 U/ml penicillin/streptomycin (Bristol-Myers Squibb), and 50 µM 2 mercaptoethanol (BioRad) (DC medium) at 37° C. Following washing, adherent monocytes were cultured in 10 ng/ml rhIL-4 (R&D Systems) and 100 ng/ml rhGM-CSF (R&D Systems) in DC medium in the absence (mDC) or presence (DC-10) of 10 ng/ml of rhIL-10 (BD, Bioscience) for 7 days. After 5 days, mDC differentiated in the absence of rhiL-10 were stimulated with 1 µg/ml of LPS (Sigma Aldrich) for additional 2 days. To generate T(DC-10) cell lines, $10^5$ DC-10 were cultured with $10^6$ allogeneic CD4+ CD45RO− T cells in 1 ml of X-vivo 15 medium (Biowhittaker), supplemented with 5% pooled AB human serum (Biowhittaker), and 100 U/ml penicillin/streptomycin (Bristol-Myers Squibb). After 6 or 7 days, rhIL-2 (20 U/ml; Chiron Italia) was added, and the cells were expanded for additional 7-8 days. Fourteen days after culture the T cells were collected, washed, and functionally analyzed. As control, T cells differentiated with mDC were used. T cells stimulated with DC-10 are indicated as pTr1(DC-10), and T cells stimulated with mDC as T(mDC).

Murine T Cells

Murine naive CD4+ T cells (CD4+CD62L$^{hi}$CD25−) from C57BL/6 mice were activated with plate-bound anti-CD3 (2-5 µg/ml; 145-2C11) and anti-CD28 (1-2 µg/ml; PV-1) mAbs. $T_H0$ cells were differentiated in the presence of anti-IFN-γ (10 µg/ml) and anti-IL-4 (10 µg/ml) mAbs. Tr1 cells were differentiated in the presence of murine recombinant IL-27 (25 ng/ml) and TGF-β (2 ng/ml). $T_H2$ cells were differentiated in the presence of murine recombinant IL-4 (10 ng/ml) and anti-IFNγ (10 µg/ml). $T_H17$ cells were differentiated in the presence of murine recombinant TGF-β (0.5 ng/ml), IL-6 (10 ng/ml), IL-23 (20 ng/ml), anti-IFNγ (10 g/ml), and anti-IL-4 (10 µg/ml). $T_H1$ cells were differentiated in the presence of murine recombinant IL-12 (10 ng/ml), IL-2 (50 u/ml), and anti-IL-4 (10 µg/ml). Foxp3+ Tregs cells were differentiated in the presence of murine recombinant TGF-β (2 ng/ml), IL-2 (50 U/ml), anti-IFNγ (10 µg/ml) and anti-IL-4 (10 µg/ml). After four days of culture, T cells were harvested and analyzed.

RNA Isolation and DNA Microarray Experiments

RNA was isolated from Tr1 and $T_H0$ cell clones from two distinct HDs unstimulated (t0) or stimulated (6 and 16 hours) with immobilized anti-CD3 mAb (10 µg/mL; Jansen-Cilag) and soluble anti-CD28 mAb (1 µg/mL, BD Pharmingen) in complete medium at a concentration of $10^6$ T cells/ml. Total RNA was extracted with RNeasy Mini kit (Qiagen, Hilden, Germany) according to manufacturer's instructions. A total RNA (100 ng) was used for GeneChip analysis. Preparation of terminal-labelled cDNA, hybridization to the whole-transcript GeneChip® Human Gene 1.0 ST Array (Affymetrix, Santa Clara, Calif., USA) and scanning of the arrays was carried out according to manufacturer's protocols. Raw data was preprocessed with RMA algorithm. In order to detect differentially expressed genes, Welch t-test without p-value correction was performed. Genes were considered as differentially expressed if gene expression was more than 2 times different with p-value<0.05. All these steps were performed using R and Bioconductor.

Real-Time Quantitative PCR Analysis

Human Samples

Total RNA was extracted with RNeasy Mini kit (Qiagen, Hilden, Germany), and cDNA was synthesized with high-capacity cDNA Reverse Transcription kit (Applied Biosystems, Foster City, Calif.) according to manufacturer's instructions. Real time analysis was performed using ABI Prism 7500/SDS2.2.1 software. Levels of mRNA were quantified using Assay on Demand quantitative Reverse Transcription Polymerase Chain Reaction (RT-PCR) kits (Applied Biosystems) with TaqMan Universal PCR Master Mix (Applied Biosystems). Samples were run in duplicate or triplicate, and relative expression was determined by normalizing to hypoxanthine phosphoribosyltransferase 1 (HPRT) and/or β2-microglobulin (B2M) expression in each set of samples to calculate a fold-change in value and by comparing the relative amount to calibrator (expression level of a pool of CD4+ T cell lines from 4 distinct HDs). Analyses were performed with the qBase v1.3.5 software (Jan Hellemans & Jo Vandesompele).

Murine Samples

Total RNA was extracted from cells using Trizol® Reagent, followed by RNA clean up using the RNeasy Kit (Quiagen). The High capacity cDNA synthesis Kit (Applied Biosystems) was used for synthesis of cDNA. Real-time PCR analysis was performed using TaqMan® Fast Universal PCR Mater Mix and TaqMan® Gene Expression Assays (Applied Biosystems) on 7500 Fast Real-time PCR system machine (Applied Biosystems). Samples were run in duplicate or triplicate, and relative expression was determined by normalizing to hypoxanthine phosphoribosyltransferase 1 (hrpt) expression.

Cytokine Detection

Human Samples

Human T cells (0.2-0.4×10$^6$ cells/ml) were stimulated with immobilized anti-CD3 mAb (10 μg/mL; Jansen-Cilag) and soluble anti-CD28 mAb (1 μg/mL, BD Pharmingen) in complete medium. To measure IL-2, IL-4, IL-10, IFN-γ, and IL-17 production, culture supernatants were harvested after 24 (for IL-2 detection), or 72 hours (for other cytokines) of culture and levels of cytokines were determined by capture ELISA according to the manufacturer's instruction (BD Biosciences). The limits of detection were as follows: IFN-γ: 60 pg/ml; IL-10: 19 pg/ml; IL-4: 9 pg/ml; IL-17: 30 pg/ml.

Murine Samples

Murine T cells (0.3-0.5×10$^6$ cells/ml) were stimulated for 72 hours with immobilized anti-CD3 mAb (10 μg/mL; Jansen-Cilag) and soluble anti-CD28 mAb (10 μg/mL, BD Pharmingen) in complete medium. Cytokines were quantified by Cytometric Bead Array (BD Bioscience) according to the manufacturer's instructions.

Flow Cytometry Analysis

Human T Cells.

Human T cells were stained with anti-CD4 (BD Pharmingen), anti-CD49b (Biolegend, San Diego, Calif., USA), anti-LAG-3 (R&D System), anti-CD226 (Biolegend), anti-CD45RA, and anti-CD25 (BD Pharmingen) mAbs. The staining for CD49b and LAG-3 was performed at 37° C. for 15 minutes. Intracellular staining was used for the detection of FOXP3 (clone 259D, Biolegend), following the manufacturers' instructions. Samples were acquired using a BD FACS Canto flow cytometer (BD Biosciences), and data was analyzed with FCS express (De Novo Software). Quadrant markers were set accordingly to unstained controls.

Murine T Cells

Murine T cells were stained with anti-CD4, anti-TCRβ, anti-CD45.1, anti-CD45.2, anti-CD49b (clone HMa2), anti-LAG-3 (clone C9B7W), anti-CD226 mAbs all purchased from Biolegend. The staining for CD49b and LAG-3 was performed at 37° C. for 15 minutes and at room temperature for additional 15 minutes. For the purification of T cell populations according to the expression of CD49b and LAG-3, CD4+ T cells were first enriched by magnetic-activated cell sorting beads (MACS; Miltenyi Biotec) and then further purified with a FACSVantage (BD). Purity of sorted cells was higher than 95%.

Suppressive Functions

Human T Cells

To evaluate the suppressive activity of human T cells, CD4$^+$ T cells (responder cells) were stained with CFSE (Molecular Probes) and were activated with anti-CD3, anti-CD2, and anti-CD28-coated beads (Trl Inspector, Miltenyi Biotech, Bergisch Gladbach, Germany), at a ratio of three beads per cell. Suppressor cells were added at a ratio of 1:1. The percentage of divided responder T cells was calculated by gating on CD4$^+$ cells, as described elsewhere (Lyons and Parish, 1994, J Immunol Methods 171, 131-137).

Murine T Cells.

To determine the suppressive activity of murine T cells, CD45.1+CD4$^+$CD25$^-$ T cells (responder cells) were labeled with Cell Trace Violet Cell Proliferation Kit (1 μM; Invitrogen) and were cultured in a 96-well flat bottom plates (20-50×10$^3$ cells/well) with or without CD4$^+$CD49b$^+$LAG-3$^+$Foxp3$^{RFP-}$, CD4$^+$CD49b$^-$LAG-3$^+$Foxp3$^{RFP-}$, CD4$^+$CD49b$^+$LAG-3$^-$Foxp3$^{RFP-}$ and CD4$^+$CD49b$^-$LAG-3$^-$Foxp3$^{RFP-}$ T cells FACS-sorted from the different organs. The ratio between responder and suppressor was 1:1, 2:1, 4:1, 8:1. Irradiated APCs (splenocytes MACS depleted for CD4 and CD8 T cells) were used as feeder cells (4×10$^5$ cells/well). Cells were stimulated with 1 μg/ml of CD3 mAb (2C11). In some experiments suppression was performed in the presence of anti-IL10Rα (50 ug/ml; clone 1B1) mAb. After 72 hours, Cell Trace Violet dilution in CD45.1$^+$CD4$^+$ (responder cells) was analyzed by flow cytometry. The percentage of divided responder T cells was calculated as described (Lyons and Parish, 1994, J Immunol Methods 171, 131-137).

Endoscopic and Histopathology Procedure

Colonoscopy was performed in a blinded fashion for colitis scoring via the Coloview system (Karl Storz, Germany) (Huber et al., 2011, Immunity 34, 554-565; Becker et al., 2006, Nature 440, 303-307). In brief, colitis scoring was based on granularity of mucosal surface, stool consistence, vascular pattern, translucency of the colon, and fibrin visible (0-3 points for each). For the histology, colons were fixed in Bouin's fixative solution and embedded in paraffin.

Anti-CD3 and Intestinal Lymphocyte Isolation

Mice were injected with anti-CD3 (15 μg, 145-2C11) mAb, isotype antibody, or PBS i.p. two times every other day. After removal of the Peyer's Patches, intraepithelial lymphocytes (IEL) and lamina propria lymphocytes (LPL) were isolated via incubation with 5 mM EDTA at 37° C. for 30 min (for IEL), followed by further digestion with collagenase IV and DNase at 37° C. for 1 hour (for LPL). Cells were then further separated with a Percoll gradient. If not indicated differently, cells were isolated from the upper part of the small intestine (duodenum+jejunum) of anti-CD3-treated mice.

Parasite and Infection

Third-stage larvae (L3) of N. brasiliensis were recovered from cocultures of infected rats and washed extensively. Five hundred parasites were injected subcutaneously in 0.2 ml PBS at the base of the tail, as previously described (Fowell and Locksley, 1999, Bioessays 21, 510-518). Mice were sacrificed at designated times, and the presence of adult worms in the intestines was assessed by inverted microscopy. Whole lungs, spleens, mesenteric and mediastinal lymph nodes were excised, minced, and dispersed into single-cell suspensions. Lung suspensions were further purified by centrifugation over Ficoll (Brown et al., 1996, J Exp Med 184, 1295-1304).

Patients

Patients affected by β-thalassemia with age ranged from 2 to 17 years have been transplanted from HLA-identical sibling donors at the San Raffaele Scientific Institute since 2005 and at the Istituto Mediterraneo IME since 2004. Eleven patients who developed persistent mixed chimerism (PMC), in which patient and donor cells co-exist for longer than 2 years after transplantation, and seven patients who developed complete chimerism (CC) after allogeneic HSCT were analyzed. Informed consent was obtained from patients according to institutional guidelines and to the Helsinki Declaration.

Statistical Analysis

Average values are reported as Mean±SEM. Mann Whitney test and ANOVA test were used to determine the statistical significance of the data. Significance was defined as *P≤0.05, P≤0.005, *P≤0.0005, and ***P≤0.0001. Statistical calculations were performed with the Prism program 5.0 (GraphPad Software, Inc.). Accuracy of the percentages of CD49b$^+$LAG-3$^+$ T cells was quantified to discriminate tolerant versus non-tolerant subjects by Receiver Operating Characteristic (ROC) analysis by means of Area Under Curve (AUC) measurements. To establish the best screening power of the biomarkers, the "best" cut-off was investigated, which differentiates cases (tolerant subjects) from controls (HDs or non-tolerant subjects). Different cut-offs were chosen and the corresponding sensitivity (proportion of PMC subjects claimed to be tolerant) and specificity (proportion of HDs or CC subjects claimed to be controls) was computed. Empirical and smoothed ROC curve were thus plotted and compared to the "theoretical" situation with sensitivity and specificity equal to one. The "best" cut-off was chosen in order to maximize the "observed" specificity and sensitivity and such that percentage of positive cells separates the best cases from controls. Analyses were performed with R 2.15.2 statistical software (R-project.org/R).

The results of the experiments are now described.

Gene Expression Profile of Human Tr1 Cell Clones

Figure 1B:
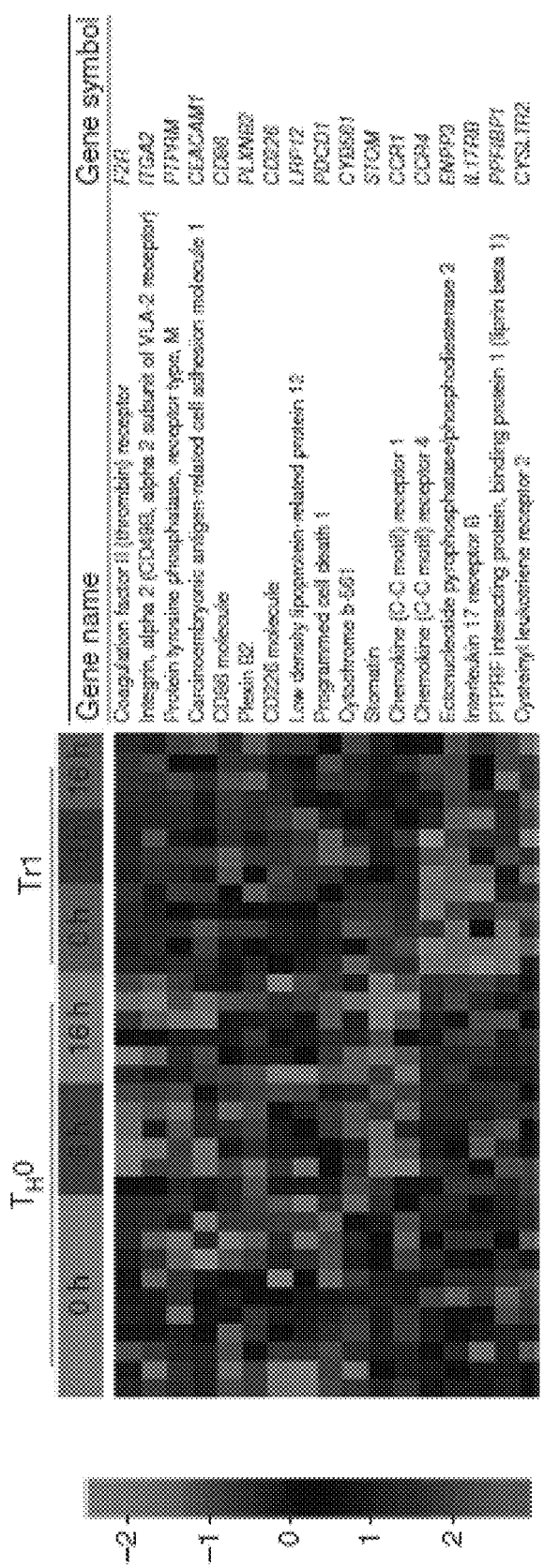
Figure 1C:
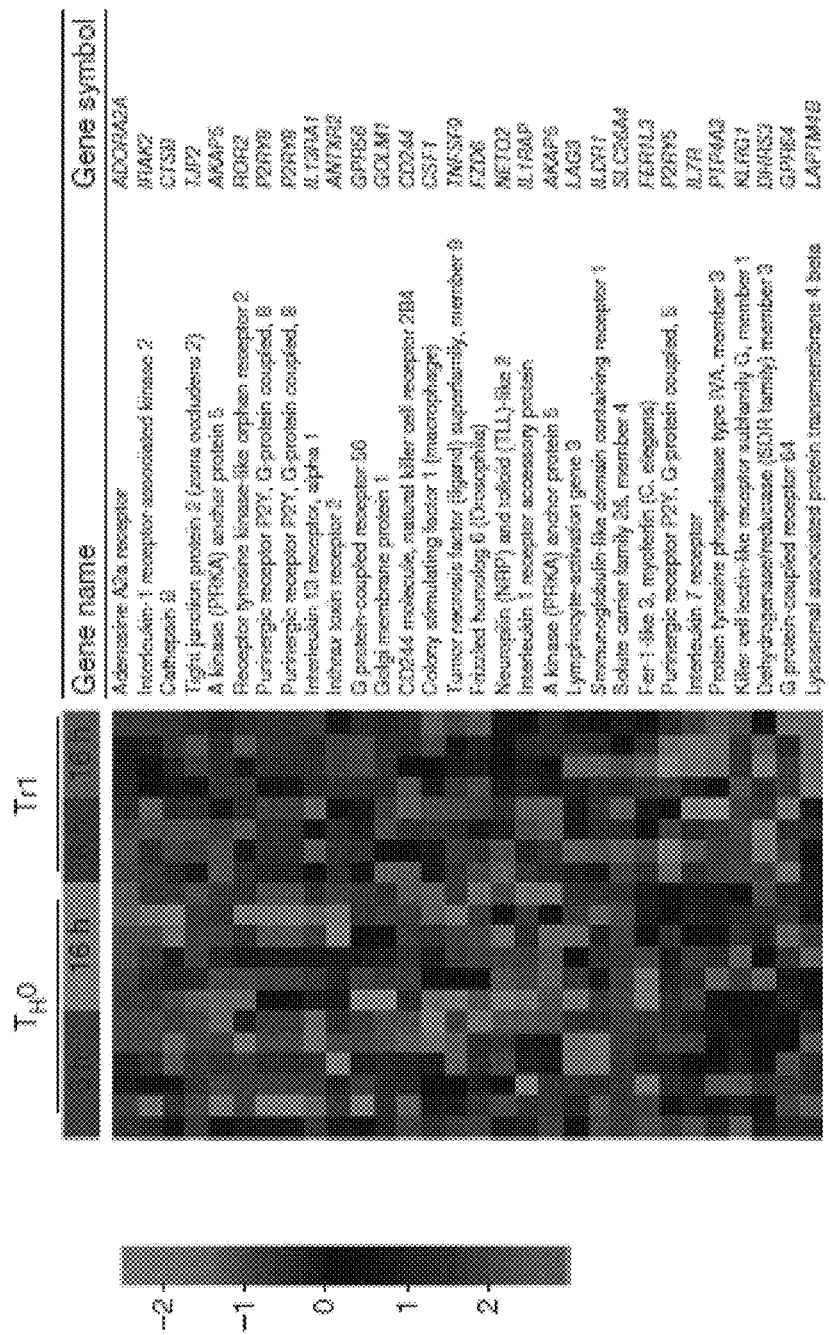
Figure 1D:
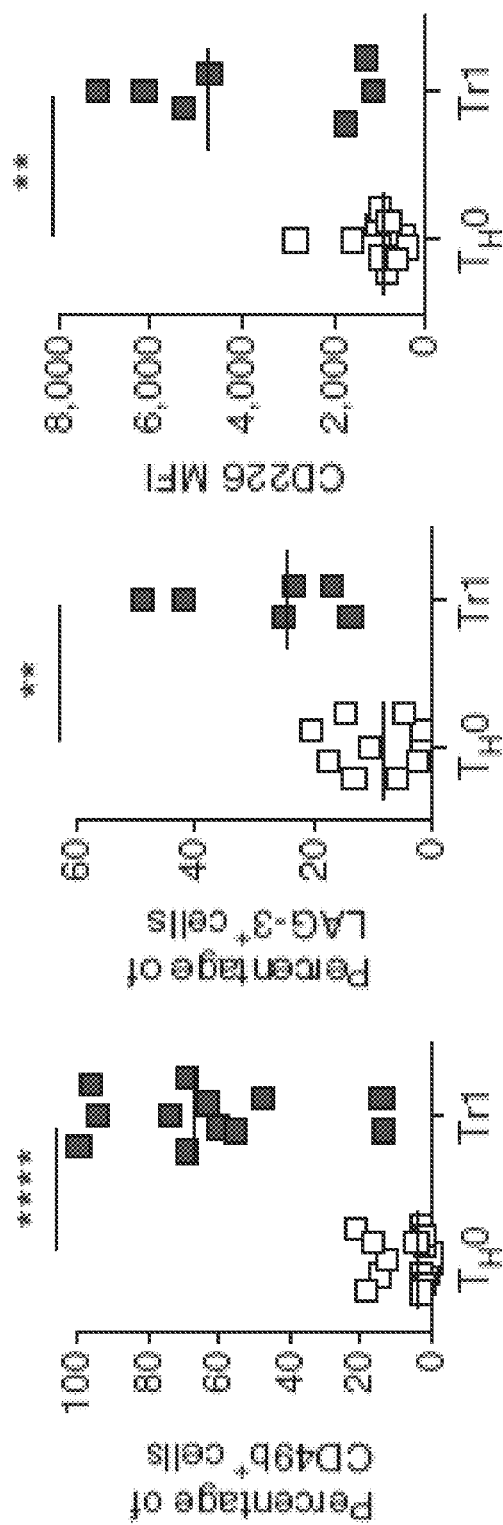
Figure 7A:
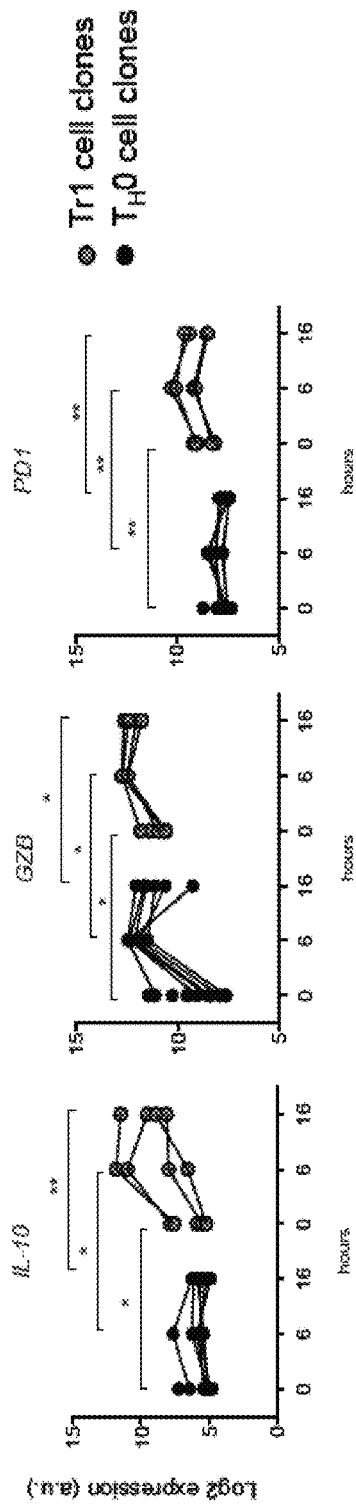
Figure 7B:
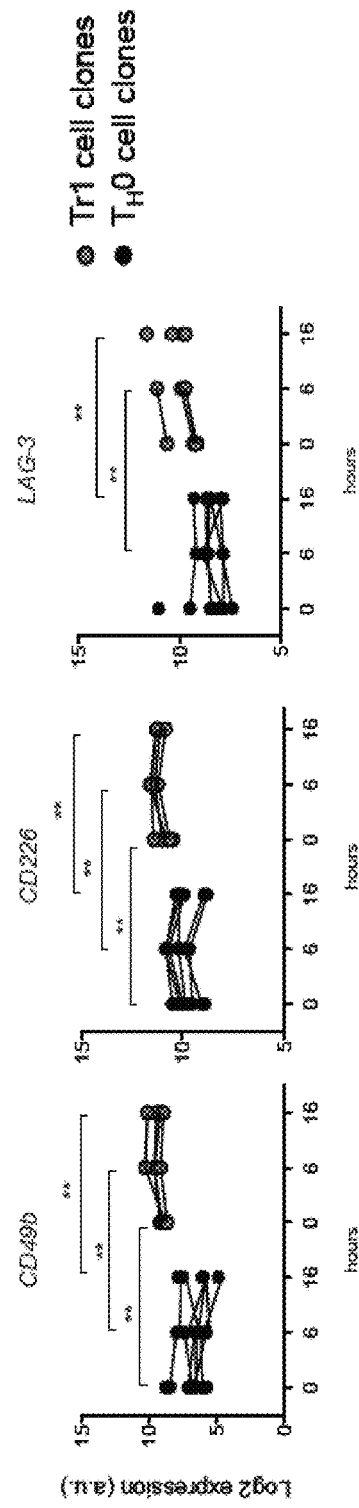

The transcriptome of human Tr1 cell clones were compared to that of $T_H0$ cell clones either unstimulated or stimulated for 6 and 16 h. The high expression of IL-10 (Groux et al., 1997, Nature 389, 737-742), GzB (Magnani et al., 2011 Eur J Immunol 41, 1652-1662; Serafini et al., 2009, Haematologica 94, 1415-1426; Grossman et al., 2004, Blood 104, 2840-2848) and PD-1 (Akdis et al., 2004, J Exp Med 199, 1567-1575) (FIG. 7A) known to be expressed in Tr1 cells, validated the microarray accuracy. The profiles of Tr1 and $T_H0$ cells were similar overall (FIG. 1A), but a small number of transcripts were uniquely expressed in Tr1 cell clones (FIG. 1A). Seventeen differentially expressed genes (DEGs) were identified in Tr1 as compared to $T_H0$ cell clones at all time points, and 28 DEGs upon activation (FIG. 1B, C). Among the 17 DEGs identified in both unstimulated and stimulated Tr1 cells ITGA2 (CD49b) and CD226 were selected according to the p-values and Log 2FC (FIG. 7B). As CD49b can be expressed also on effector $T_H$ cells (Charbonnier et al., 2006, J Immunol 177, 3806-3813; Boisvert et al., 2010, Eur J Immunol 40, 2710-2719), another marker was sought, which, in association with CD49b, could allow the isolation of Tr1 cells. LAG-3 (FIG. 7B), which has previously been shown to be associated with Tr1 functions (Workman and Vignali, 2005, J Immunol 174, 688-695) was selected, which was highly up-regulated in activated Tr1 cell clones. RT-PCR confirmed that CD49b, CD226, and LAG-3 were significantly higher in Tr1 than $T_H0$ cell clones (FIG. 7C), and in enriched IL-10-producing Tr1 cell lines isolated from in vitro Tr1-polarized cultures, as compared to $T_H0$ cell lines (FIG. 7D). FACS-analysis confirmed that Tr1 cell clones expressed significantly higher levels of CD49b and LAG-3 than $T_H0$ cell clones (FIG. 1D). All T cell clones expressed CD226, but Tr1 cell clones showed higher mean fluorescence intensity (MFI) than $T_H0$ cell clones (FIG. 1D). Overall, CD49b, CD226, and LAG-3 were identified as putative markers for human Tr1 cells.

Co-Expression of CD49b and LAG-3 Identifies Human Tr1 Cells

Figure 2A:
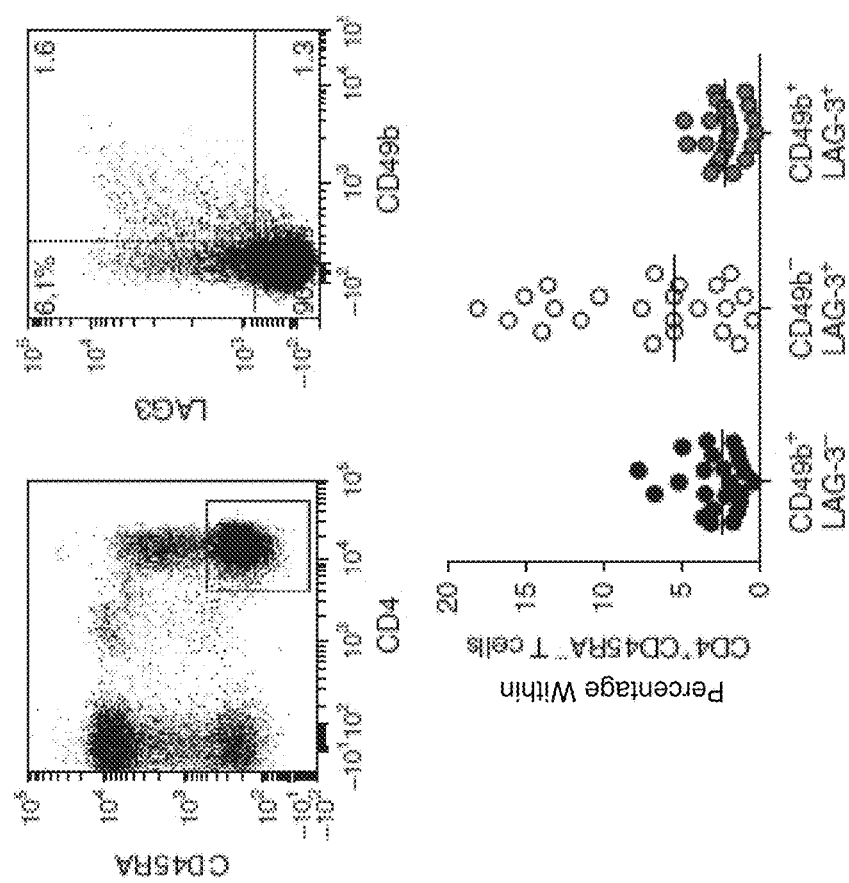
FIG. 2A through FIG. 2C, depicts the results of experiments demonstrating that the co-expression of CD49b and LAG-3 identifies human Tr1 cells in vivo in healthy donors.
Figure 8A:
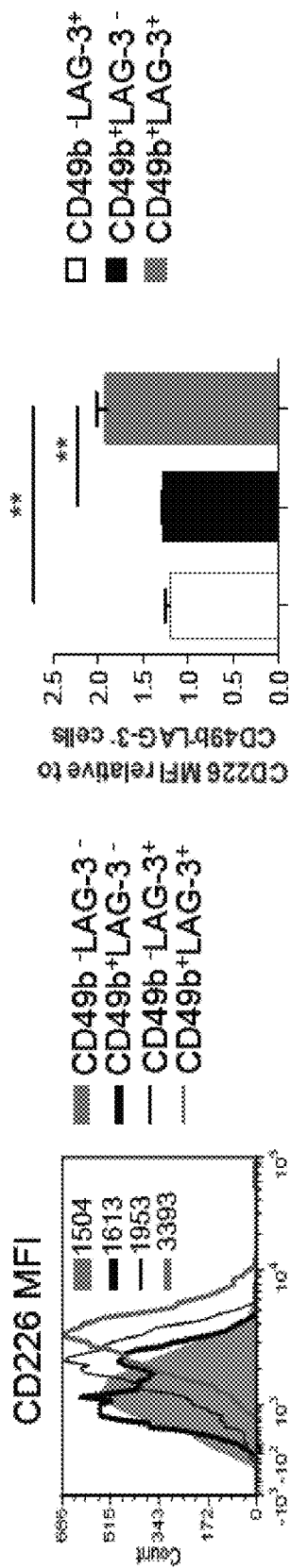
FIG. 8A through FIG. 8C, depicts the results of experiments demonstrating that CD49b$^+$LAG-3$^+$ T cells are CD25$^{low}$ and do not express FOXP3.
Figure 8B:
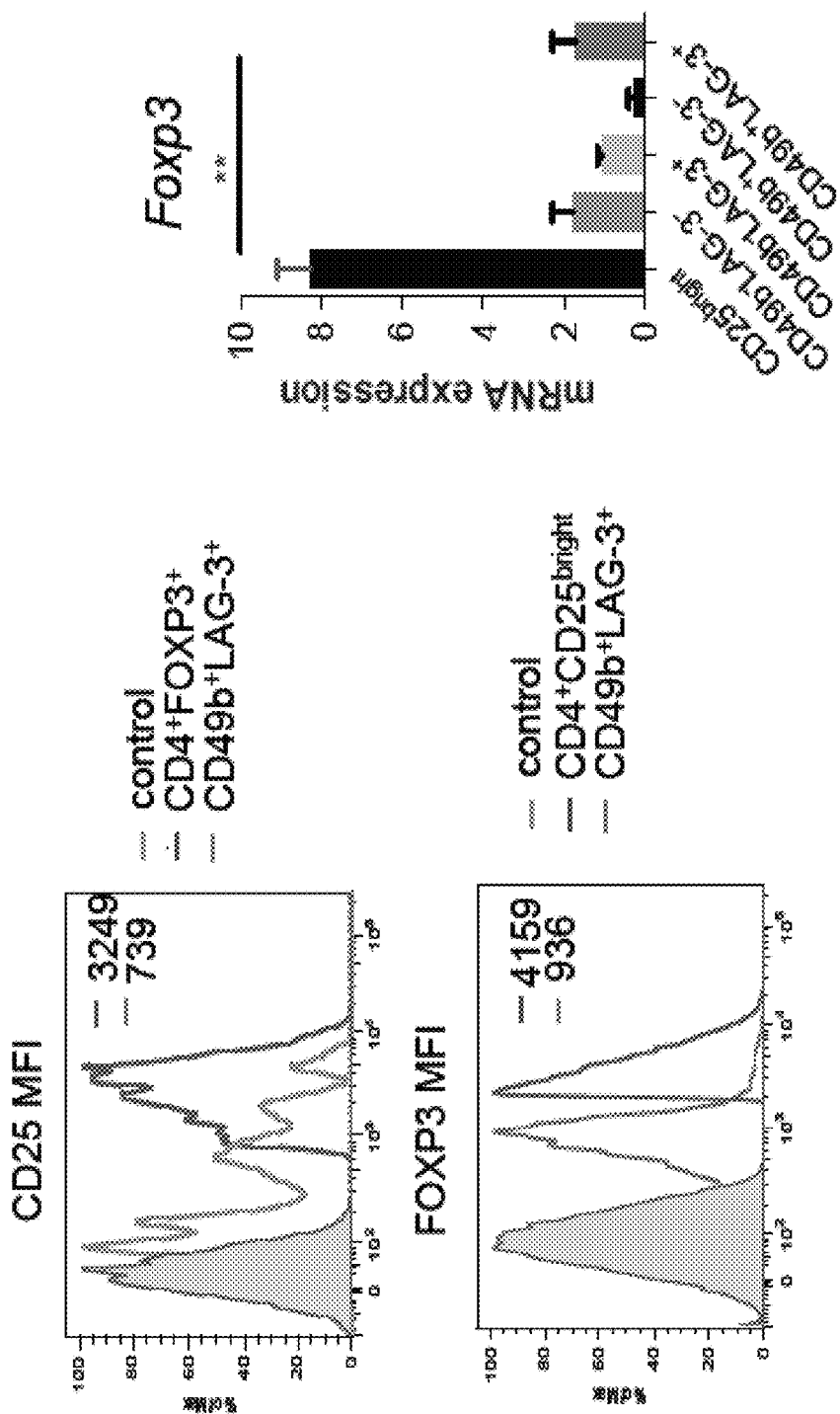

The presence of human CD4$^+$ T cells expressing CD49b, LAG-3 and CD226 was next investigated. A small population (2.14±0.25%) of memory CD45RA$^-$CD4$^+$ T cells co-expressing CD49b, LAG-3 (FIG. 2A), and CD226 (FIG. 8A) was observed in the peripheral blood of healthy donors (HDs). Of note, CD4$^+$CD49b$^+$LAG-3$^+$ T cells did not express CD25 at high levels and the expression of FOXP3 at mRNA and protein levels was significantly lower than in CD25$^{bright}$ T cells (FIG. 8B).

Figure 2B:
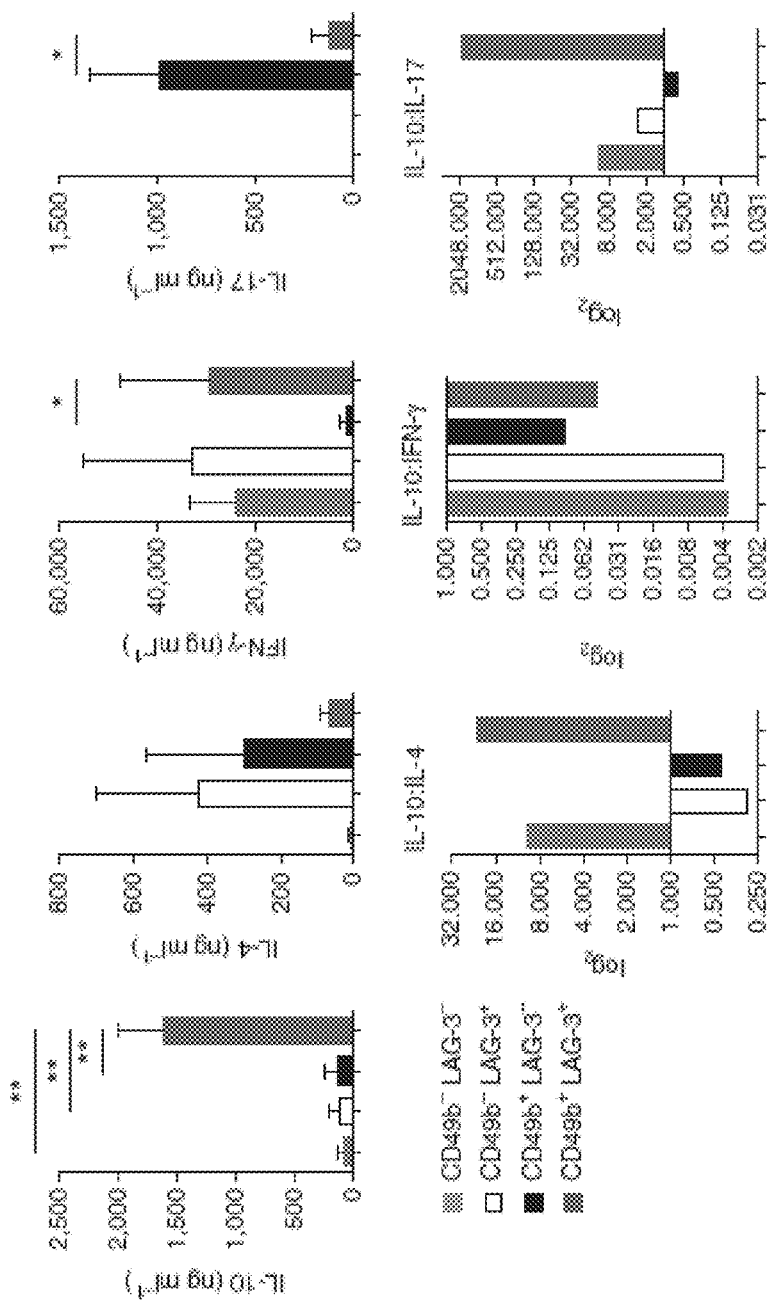
Figure 8C:
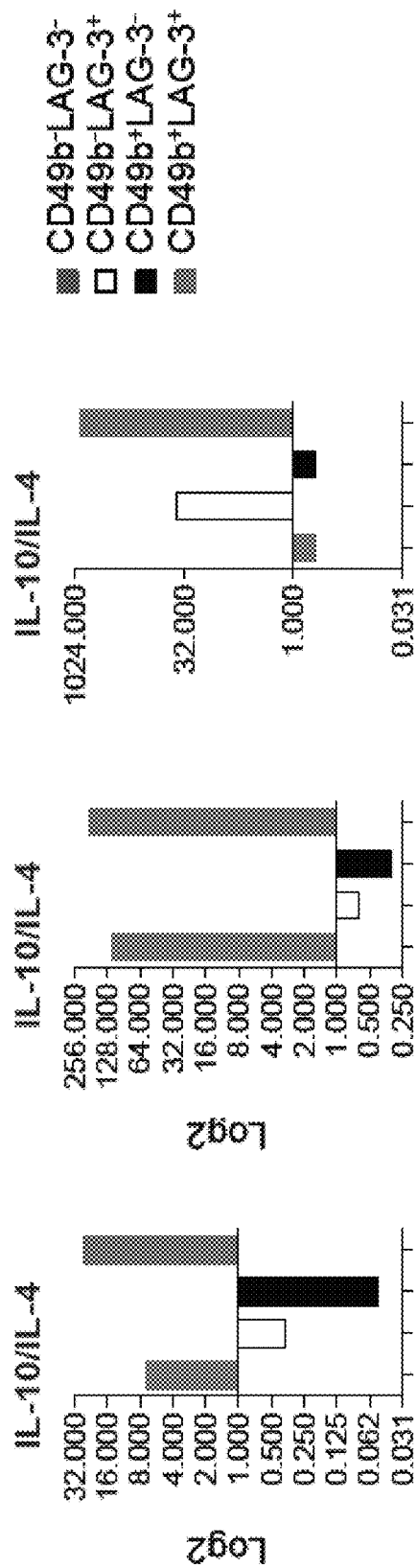

CD4$^+$CD49b$^+$LAG-3$^+$ T cells, FACS-sorted from peripheral blood of HDs, secreted significantly higher levels of IL-10 compared to CD4$^+$CD49b$^-$LAG-3$^+$, CD4$^+$CD49b$^+$LAG-3$^-$, and CD4$^+$CD49b$^-$LAG-3$^-$ T cells, as well as low amounts of IL-4 (FIG. 2B). CD4$^+$CD49b$^+$LAG-3$^+$ T cells displayed a high IL-10/IL-4 ratio, which is one of the key parameters to distinguish Tr1 from $T_H2$ cells (Groux et al., 1997, Nature 389, 737-742; Magnani et al., 2011 Eur J Immunol 41, 1652-1662; Serafini et al., 2009, Haematologica 94, 1415-1426; Passerini et al., 2011, Eur J Immunol 41, 1120-1131), (FIGS. 2B and 8C). Moreover, CD4$^+$CD49b$^+$LAG-3$^+$ T cells secreted IFN-γ, but not IL-17 (FIG. 2B).

Figure 2C:
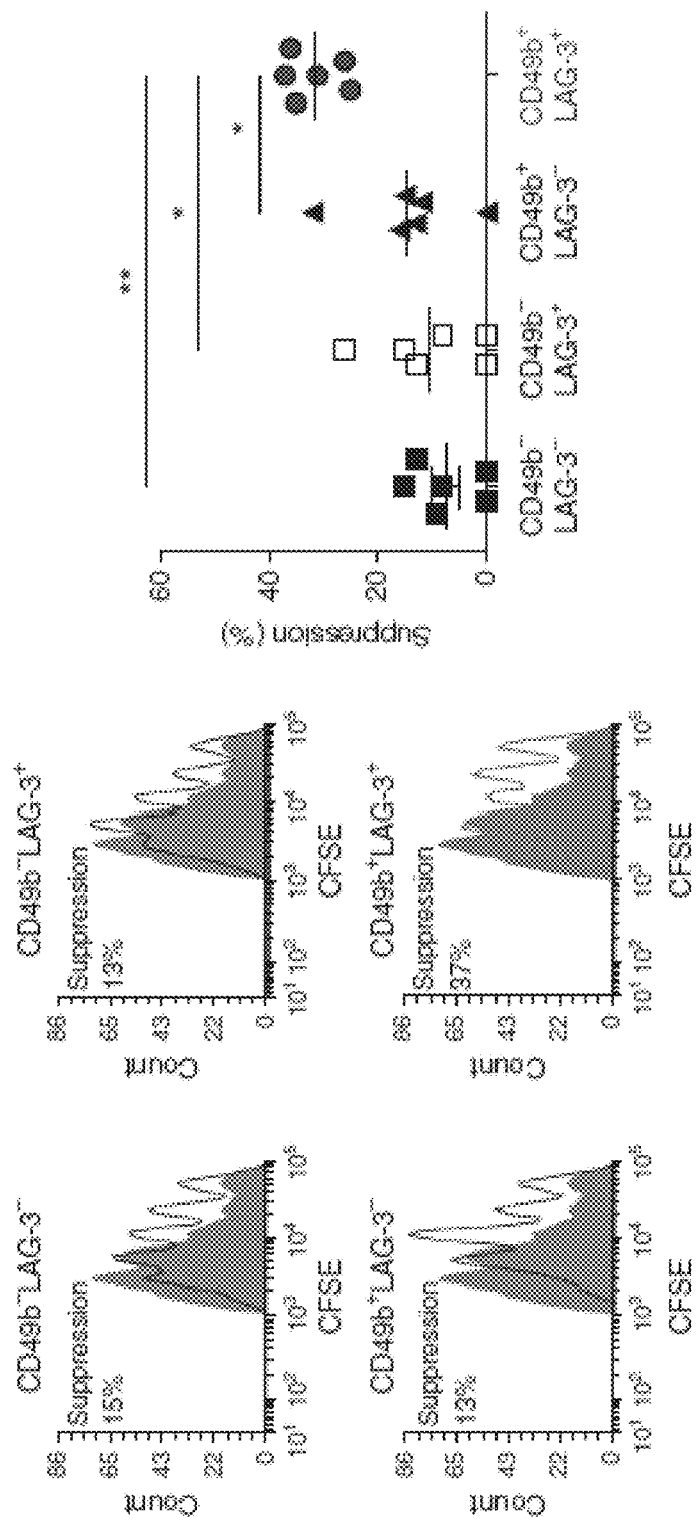

Importantly, CD4$^+$CD49b$^+$LAG-3$^+$ T cells suppressed the proliferation of CD4$^+$ T cells in vitro, which is a key feature of Tr1 cells, at significantly higher levels than the other subsets analysed (FIG. 2C).

As demonstrated herein, CD4$^+$CD49b$^+$LAG-3$^+$ T cells represent a subpopulation of CD4$^+$ memory T cells that secrete high amounts of IL-10, do not express high levels of FOXP3, and exert suppressive activity in vitro.

Co-Expression of CD49b and LAG-3 Identifies Murine Tr1 Cells

Figure 3A:
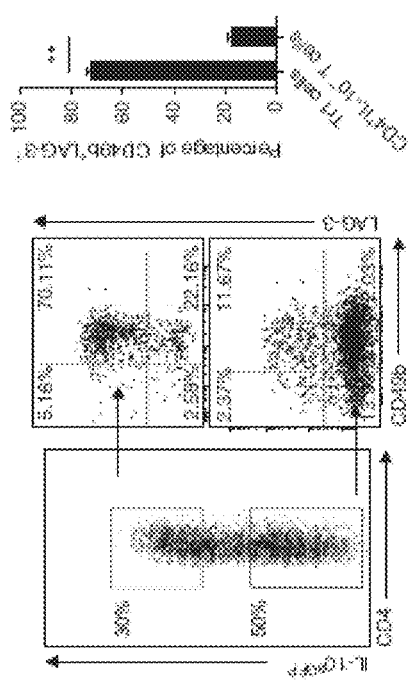
FIG. 3A through FIG. 3D, depicts the results of experiments demonstrating that co-expression of CD49b and LAG-3 identifies Tr1 cells in anti-CD3 treated mice. T cells were isolated from the small intestine of anti-CD3 treated mice.
Figure 3B:
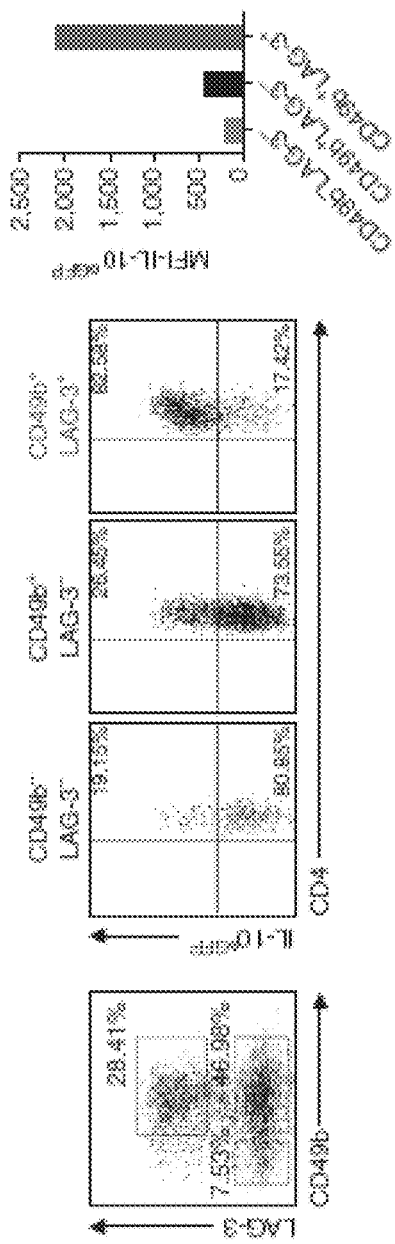
Figure 3C:
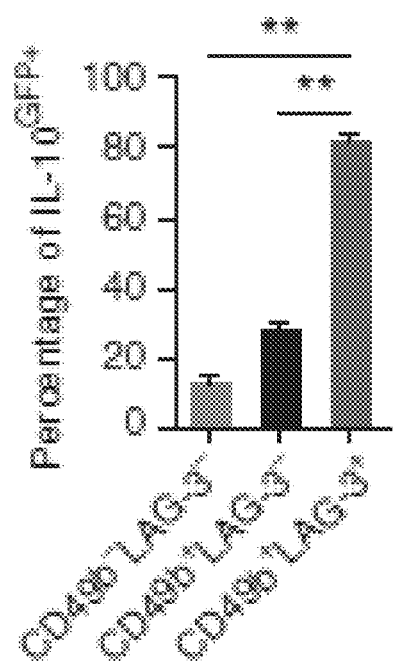
Figures 9A, 9B:
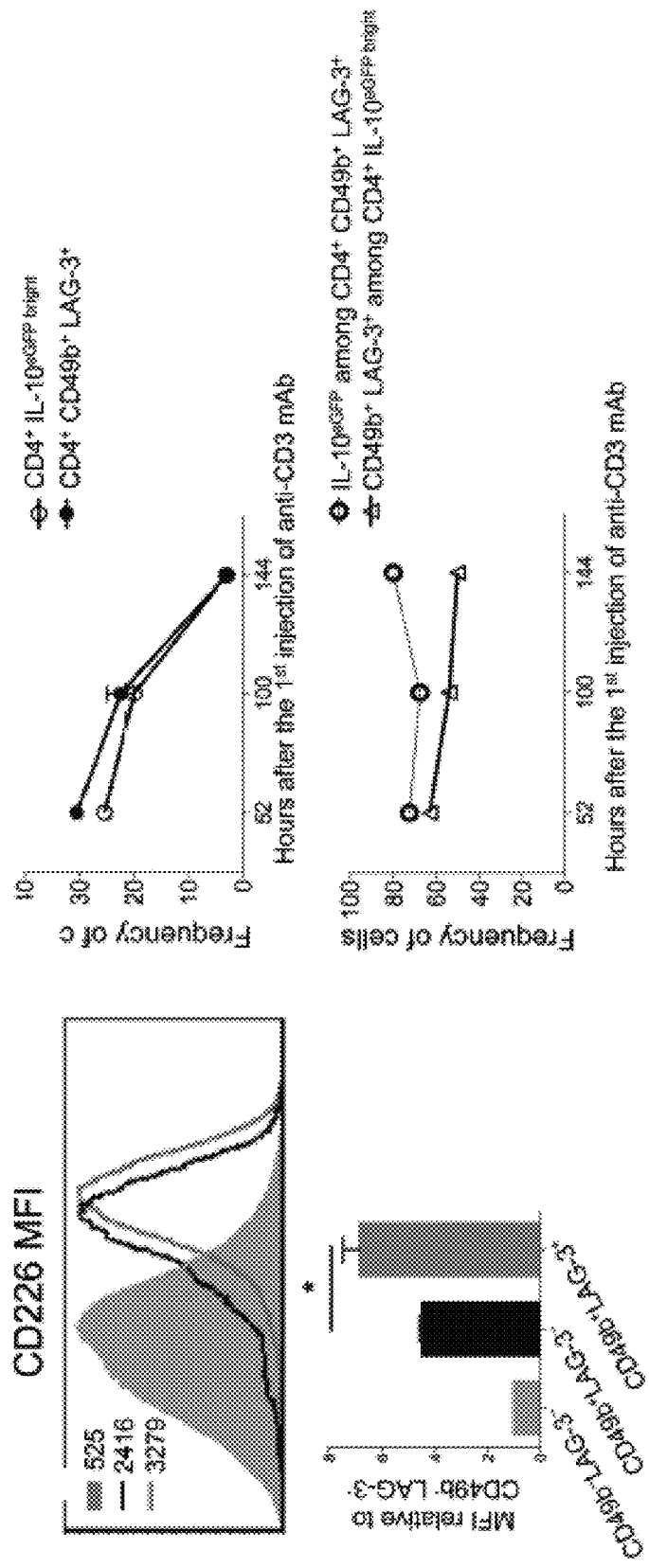
FIG. 9A through FIG. 9D, depicts the results of experiments demonstrating that co-expression of CD49b and LAG-3 identifies murine Tr1 cells in anti-CD3 treated mice.

It was recently shown that CD4$^+$Foxp3$^-$IL-10$^+$ T (Tr1) cells with strong regulatory functions accumulate in the small intestine of mice upon anti-CD3 mAb treatment (Huber et al., 2011, Immunity 34, 554-565). Here, it was tested whether these murine Tr1 cells (defined as CD4+TCRβ$^+$Foxp3$^{RFP-}$IL-10$^{eGFPbright}$) express CD49b and LAG-3. The large majority (70±5%) of CD4$^+$IL-10$^{eGFPbright}$ T cells co-expressed CD49b and LAG-3 (FIG. 3A), whereas less than 13±5% of CD4$^+$IL-10$^-$ T cells were CD49b$^+$LAG-3$^+$ (FIG. 3A). In line with this finding, CD4$^+$CD49b$^+$LAG-3$^+$ T cells isolated from the small intestine of anti-CD3 treated mice contained a very high frequency of IL-10$^{eGFP+}$ cells (FIGS. 3B and 3C), and expressed high MFI for IL-10$^{eGFP}$+ (FIG. 3B) and CD226 (FIG. 9A). These results indicate that IL-10-producing T cells and CD4$^+$CD49b$^+$LAG-3$^+$ T cells are largely superimposable. Accordingly, the frequencies of CD4$^+$TCRβ$^+$Foxp3$^{RFP-}$IL-10$^{eGFPbright}$ and CD4$^+$TCRβ$^+$CD49b$^+$LAG-3$^+$ T cells showed the same kinetics after anti-CD3 mAb treatment (FIG. 9B). Notably, the phenotype of Tr1 cells was stable, as CD49b and LAG-3 were permanently co-expressed by CD4+Foxp3-IL-10$^{eGFPbright}$ T cells (FIG. 9B).

Figure 3D:
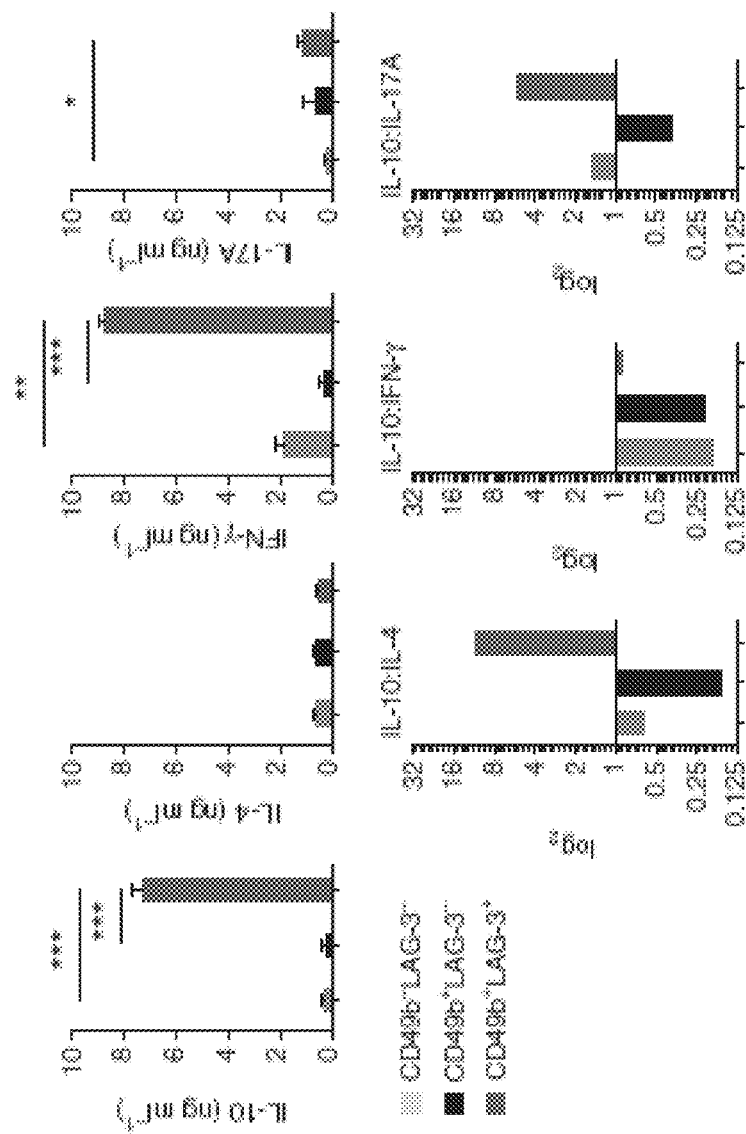
Figure 9C:
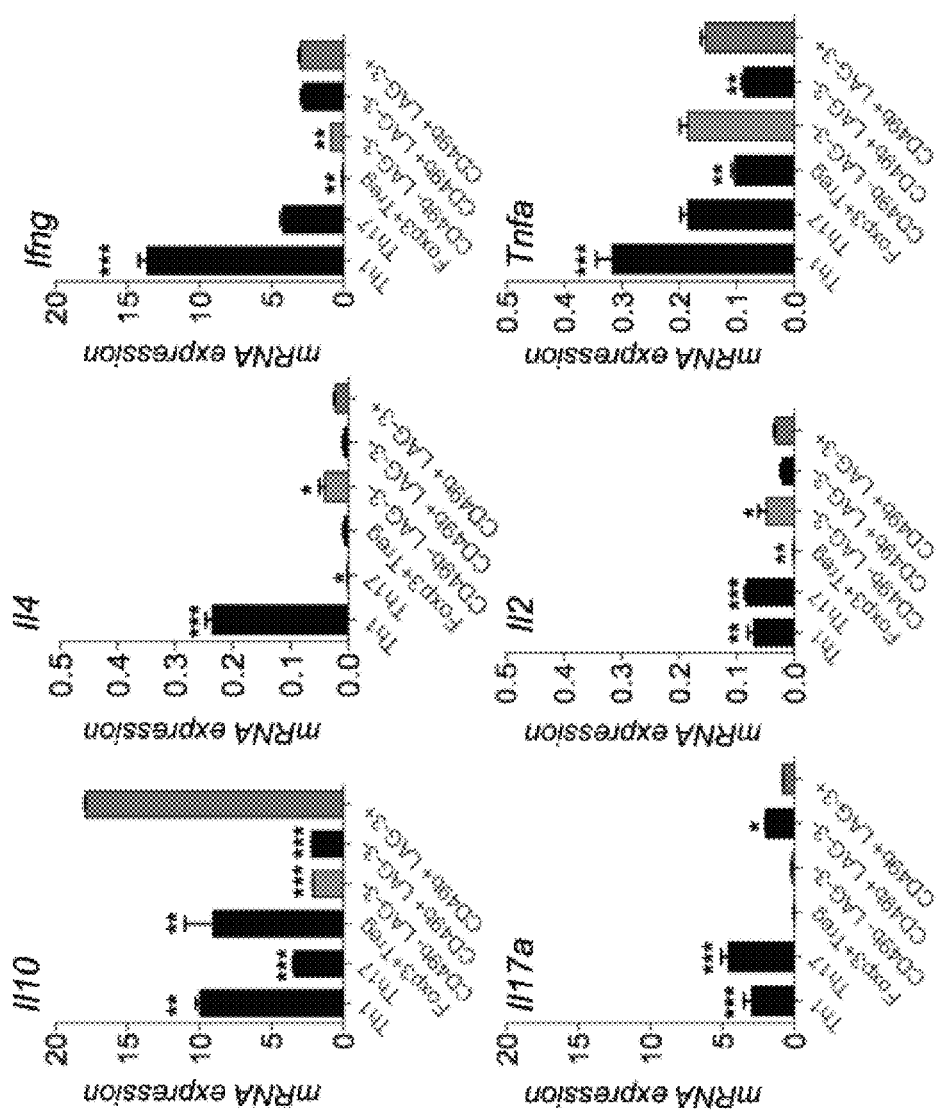
Figure 9D:
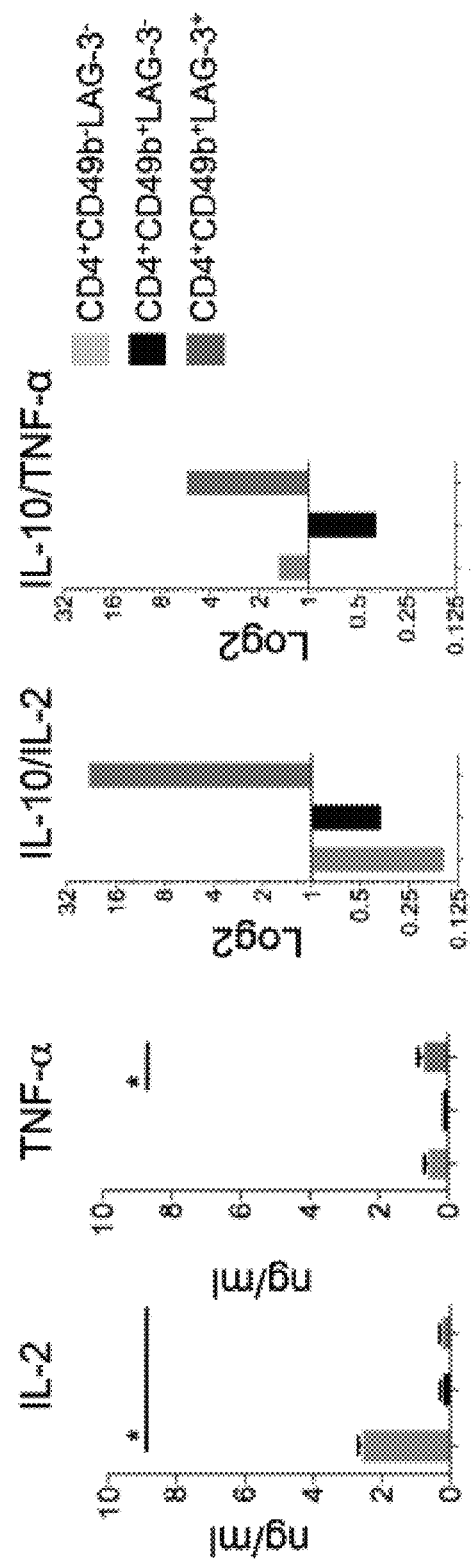

To determine whether CD49b and LAG-3 can be used to isolate murine Tr1 cells, CD4$^+$CD49b$^+$LAG-3$^+$ T cells were FACS-sorted and characterized. Without in vitro re-stimulation, CD4$^+$CD49b$^+$LAG-3$^+$ T cells expressed high levels of Il10 and very low levels of Il4; expression of Ifng, Il2, Tnfa, and Il17a was significantly lower than in $T_H1$ and $T_H17$ cells, respectively (FIG. 9C). Upon re-stimulation in vitro, CD4$^+$CD49b$^+$LAG-3$^+$ T cells secreted large amounts of IL-10, which were five to eight fold higher than IL-4, IL-17A, IL-2, and TNF-α (FIGS. 3D and 9D), and significant amounts of IFN-γ (FIG. 3D).

Figure 10:
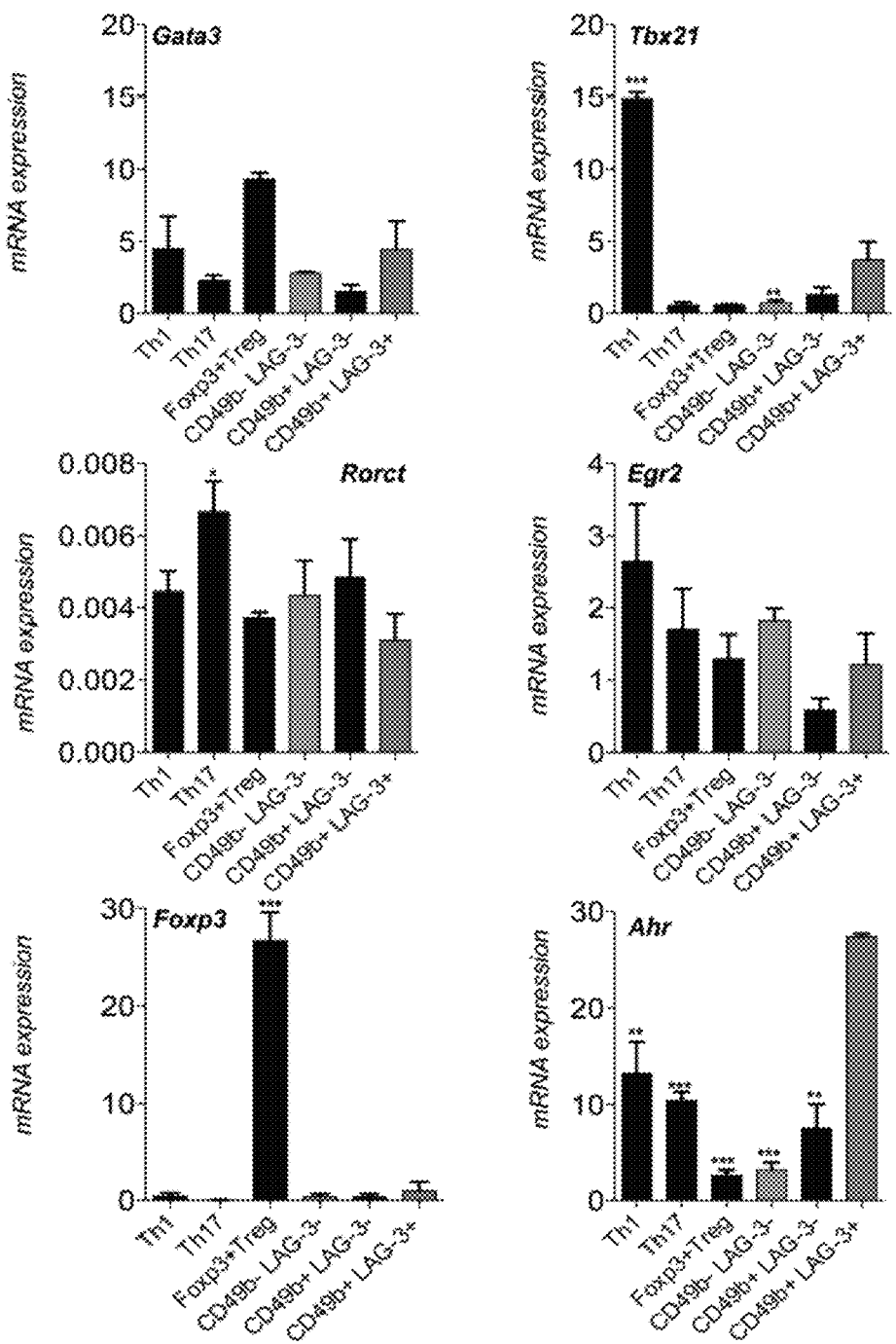
FIG. 10 depicts the results of experiments demonstrating that CD4$^+$CD49b$^+$LAG-3$^+$ T cells express AhR. Expression of the indicated transcription factors (normalized to Hprt) measured by RT-PCR in the indicated FACS-sorted T cell populations from the small intestine of anti-CD3 treated mice. As controls, T$_H$1 (CD4$^+$TCRβ$^+$IFN-γ$^{Katushka}$+), T$_H$17 (CD4$^+$TCRβ$^+$IL-17A$^{eGFP+}$) and Foxp3$^+$ Tregs (CD4$^+$TCRβ$^+$Foxp3$^{RFP+}$) isolated from the small intestine of Foxp3$^{RFP}$IFN-γ$^{Katushka}$ and Foxp3$^{RFP}$IL-17A$^{eGFP}$ reporter mice injected with anti-CD3 mAb were used. Mean±SEM of 3 independent experiments is shown. *P 0.05, P 0.005, and *P 0.0005 vs. CD4$^+$ CD49b$^+$LAG-3$^+$ T cells. When not indicated differences were not statistically different.

CD4$^+$CD49b$^+$LAG-3$^+$ T cells expressed Tbx21, Rorc, and Foxp3 at significantly lower levels than $T_H1$, $T_H17$, and Foxp3$^+$ Treg cells, respectively. Gata3 levels were similar to those of $T_H1$ and Foxp3$^+$ Treg cells (FIG. 10). Despite the expression of LAG-3, CD4$^+$CD49b$^+$LAG-3$^+$ T cells expressed low levels of Egr2, a transcription factor critically involved in the development of IL-10-producing LAG-3$^+$ Tr1 cells (Okamura et al., 2009, Proc Natl Acad Sci USA 106, 13974-13979). The expression of Ahr, a key transcription factor for IL-10 production by Tr1 cells (Apetoh et al., 2010, Nat Immunol 11, 854-861), was significantly higher in CD4$^+$CD49b$^+$LAG-3$^+$ T cells compared to the other cell subsets analyzed (FIG. 10).

Figure 4A:
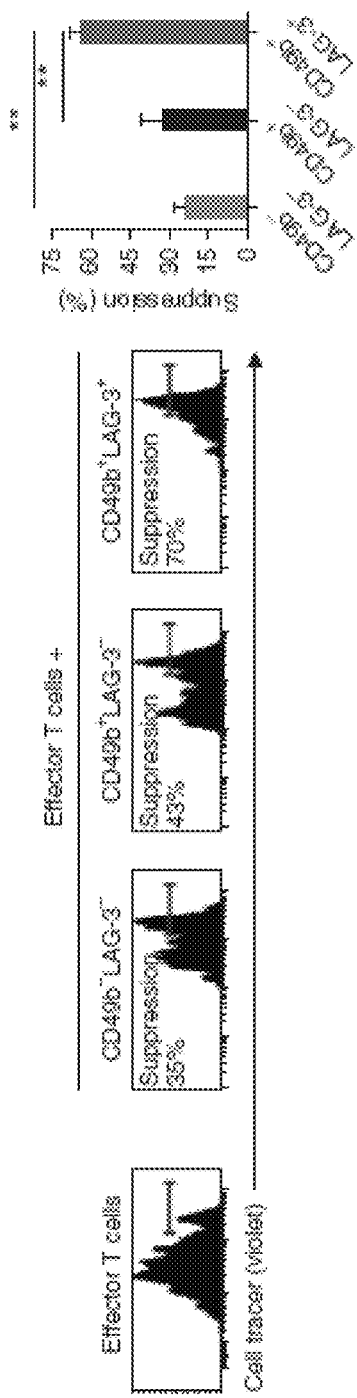
FIG. 4A through FIG. 4E, depicts the results f experiments demonstrating the in vitro and in vivo regulatory activity of murine CD4$^+$CD49b$^+$LAG-3$^+$ T cells.
Figure 4B:
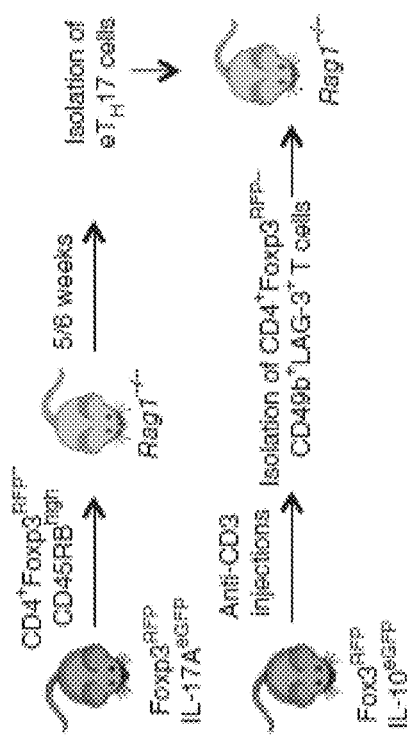
Figure 4C:
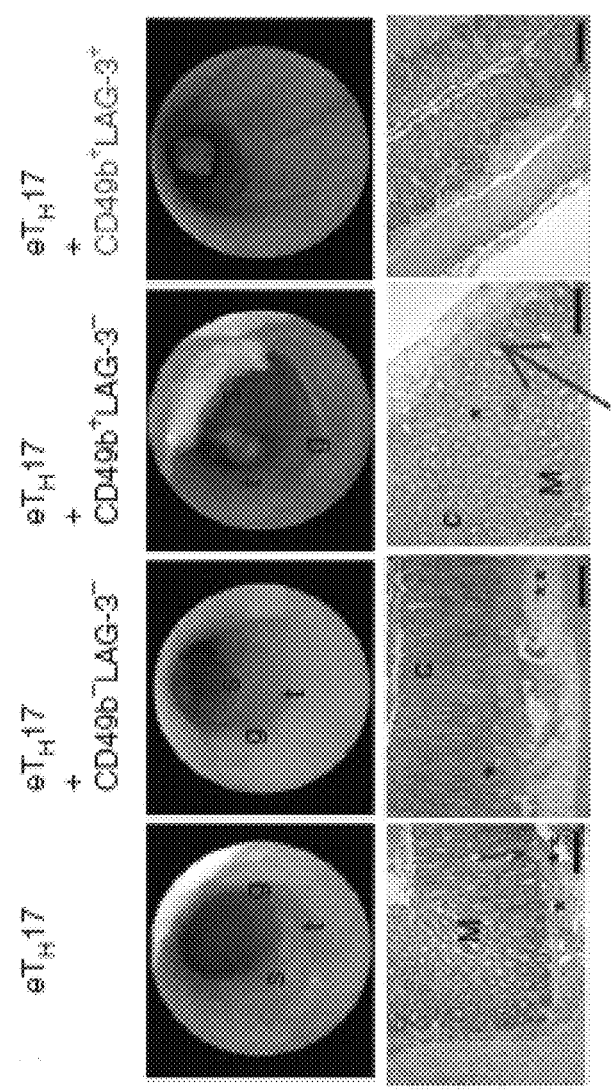
Figure 4D:
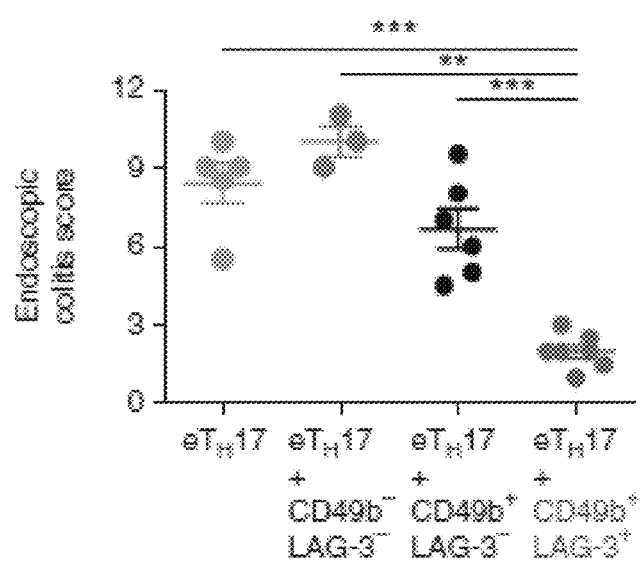
Figure 4E:
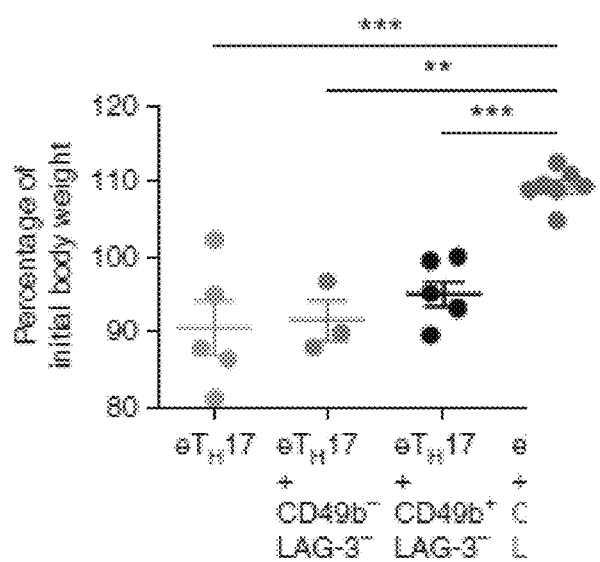
Figure 11:
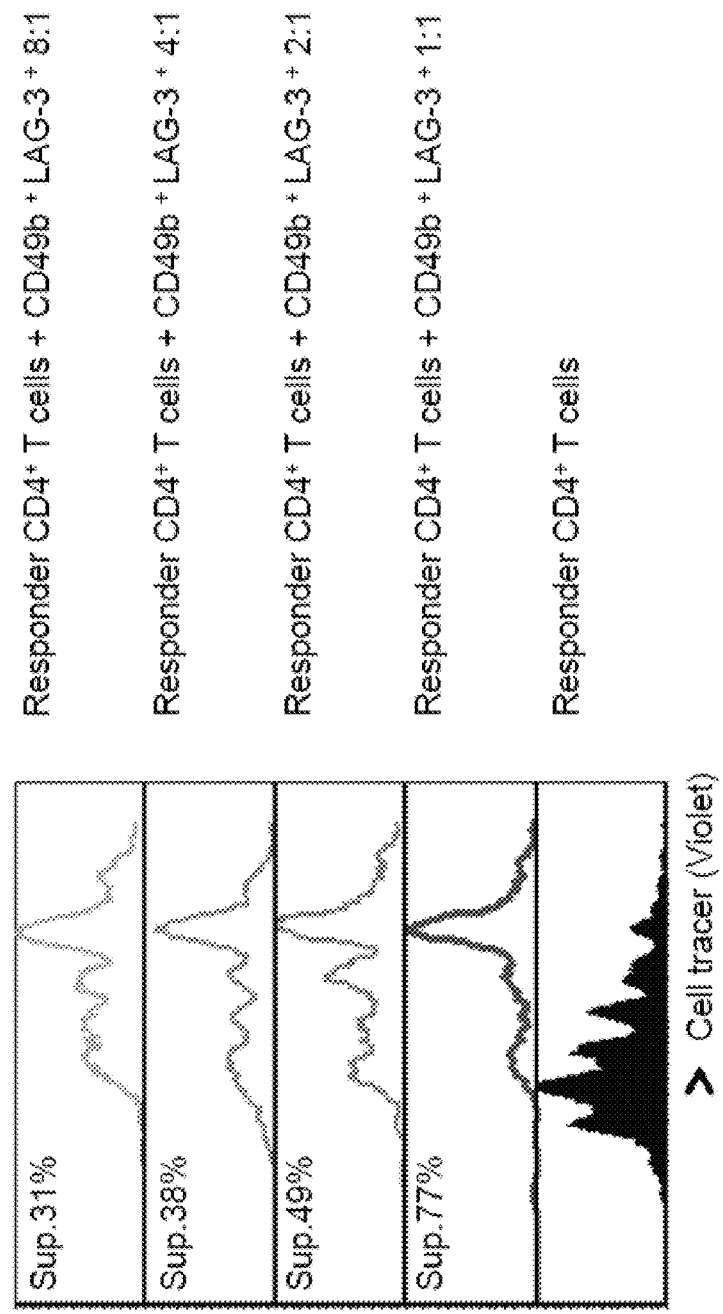
FIG. 11 depicts the results of experiments demonstrating that CD4$^+$CD49b$^+$LAG-3$^+$ T cells suppress T cell responses in vitro in a dose-dependent manner. Foxp3$^{RFP}$IL-10$^{eGFP}$ double reporter mice were injected i.p. with anti-CD3 mAb at 0 and 48 h. CD4$^+$TCRβ$^+$Foxp3$^{RFP}$-CD49b$^+$LAG-3$^+$ T cells were FACS-sorted from the small intestine of anti-CD3 treated mice 4 h after the second injection and tested for their ability to suppress the proliferation of responder CD4$^+$ T cells in vitro at the indicated cells ratios. Percentages of suppression are indicated. One representative experiment out of 2 is shown.
Figure 12:
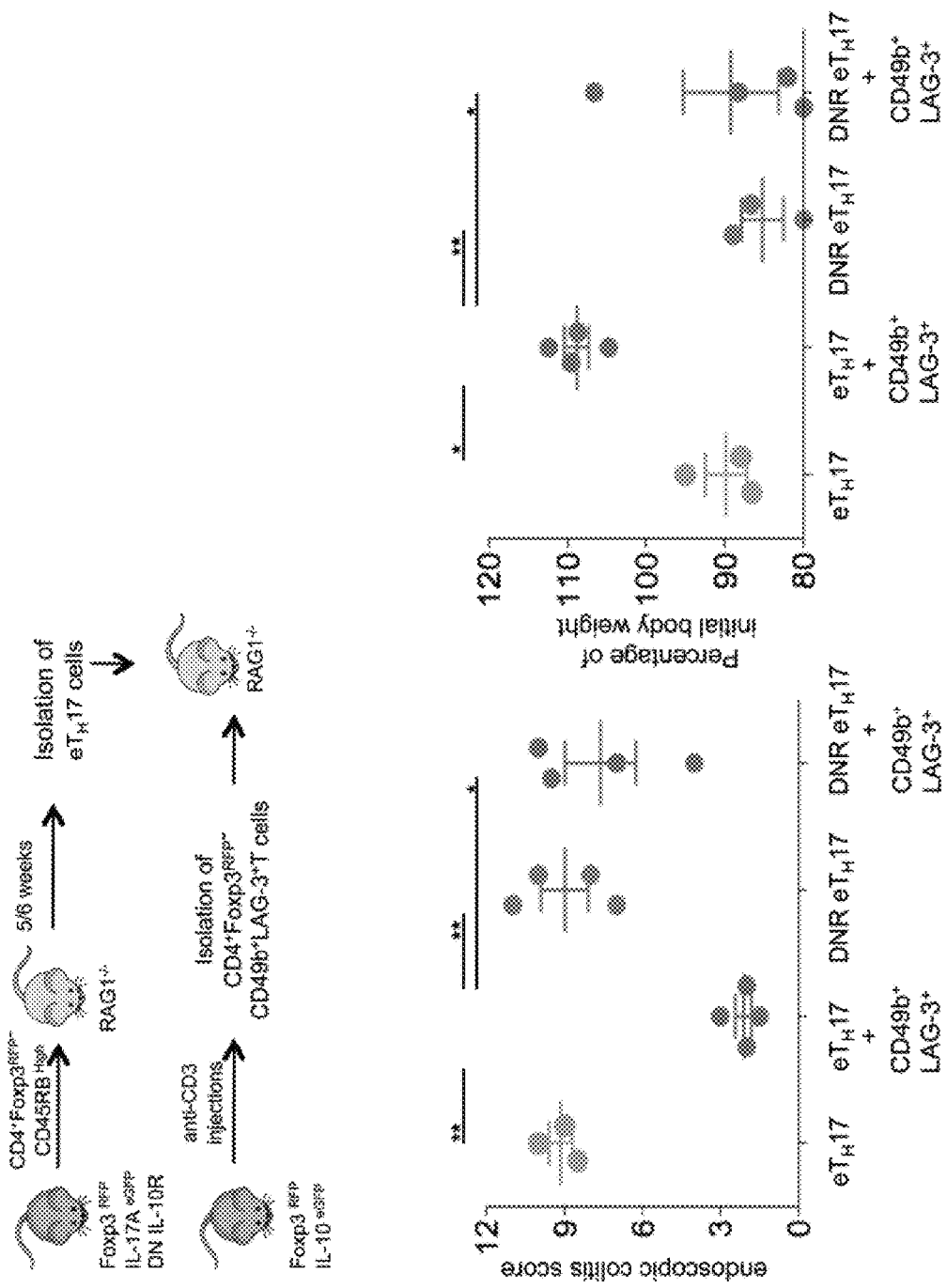
FIG. 12, comprising

CD4+Foxp3$^{RFP-}$CD49b$^+$LAG-3$^+$ T cells from the small intestine of anti-CD3 treated mice suppressed effector T cells in a dose-dependent manner in vitro (FIGS. 4A and 11). Furthermore, using a T cell transfer IBD model (Huber et al., 2011, Immunity 34, 554-565) (FIG. 4B), it was demonstrated that CD4$^+$Foxp3$^{RFP-}$ CD49b$^+$LAG-3$^+$ T cells suppressed the colitogenic eT$_H$17 cells in vivo (FIGS. 4C, 4D, and 4E), in an IL-10 dependent manner (FIG. 12).

Figures 13A, 13B:
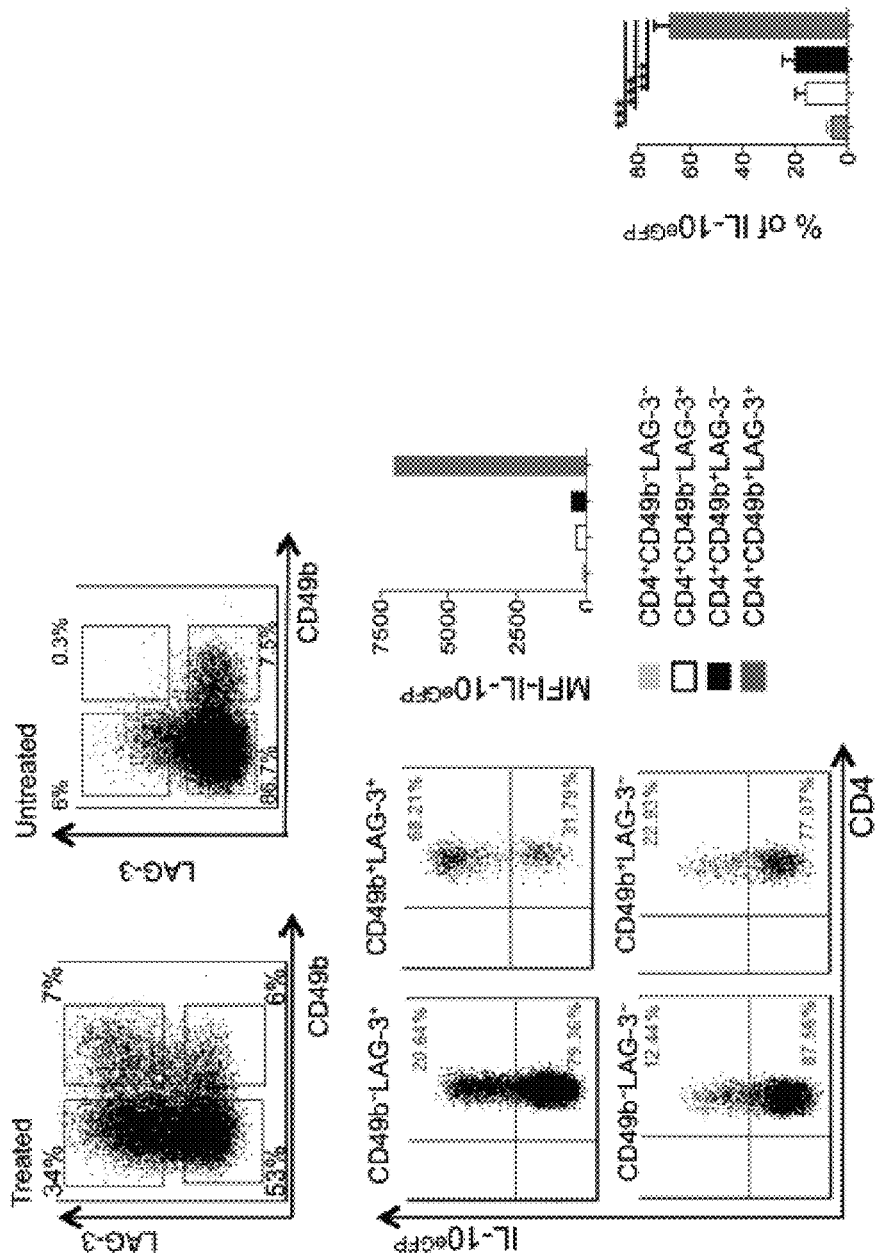
FIG. 13A through FIG. 13D, depicts the results of experiments demonstrating the in vitro regulatory activity of murine CD4$^+$CD49b$^+$LAG-3$^+$ T cells isolated from the spleen of anti-CD3 treated mice.
Figure 13C:
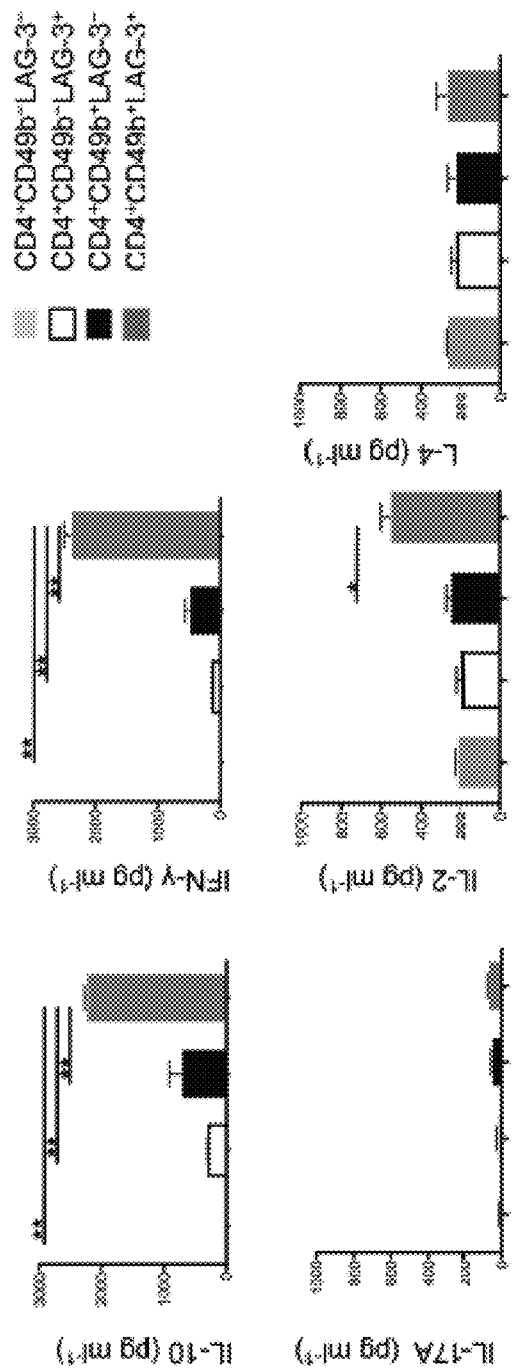
Figure 13D:
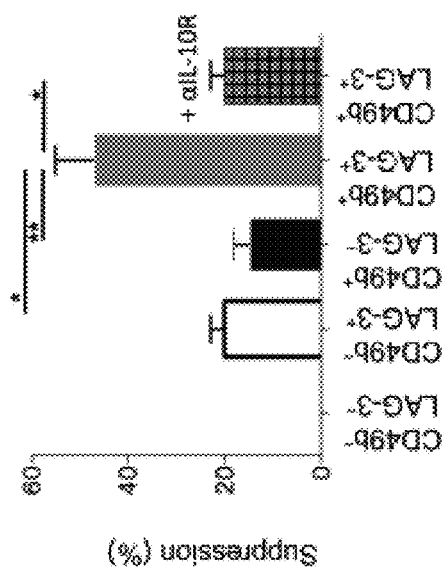

It was previously shown that Tr1 cells accumulated in the spleen of tolerant pancreatic islet transplanted mice (Battaglia et al., 2006, Diabetes 55, 40-49; Gagliani et al., 2011, PLoS One 6, e28434). In the spleen of anti-CD3 treated mice a population of CD4$^+$CD49b$^+$LAG-3$^+$ T cells was found that contained a high frequency of IL-10$^{eGFP+}$ cells (FIGS. 13A and 13B), displayed a Tr1-cytokine profile (FIG. 13C), and suppressed T-cell responses in vitro in a partially IL-10-dependent manner (FIG. 13D).

As demonstrated herein, CD4$^+$CD49b$^+$LAG-3$^+$ T cells, which accumulate in the intestine and spleen of anti-CD3 treated mice, produce large amounts of IL-10 and have strong suppressive activity in vitro and in vivo. The co-expression of CD49b and LAG-3 on CD4$^+$ T cells, therefore identifies Tr1 cells not only in humans but also in mice.

Co-Expression of CD49b and LAG-3 Distinguishes Tr1 from Other T$_H$ Cells.

To test the specificity of CD49b and LAG-3 as markers for Tr1 cells, the expression of these markers was analysed on other T$_H$ cells.

Figure 5A:
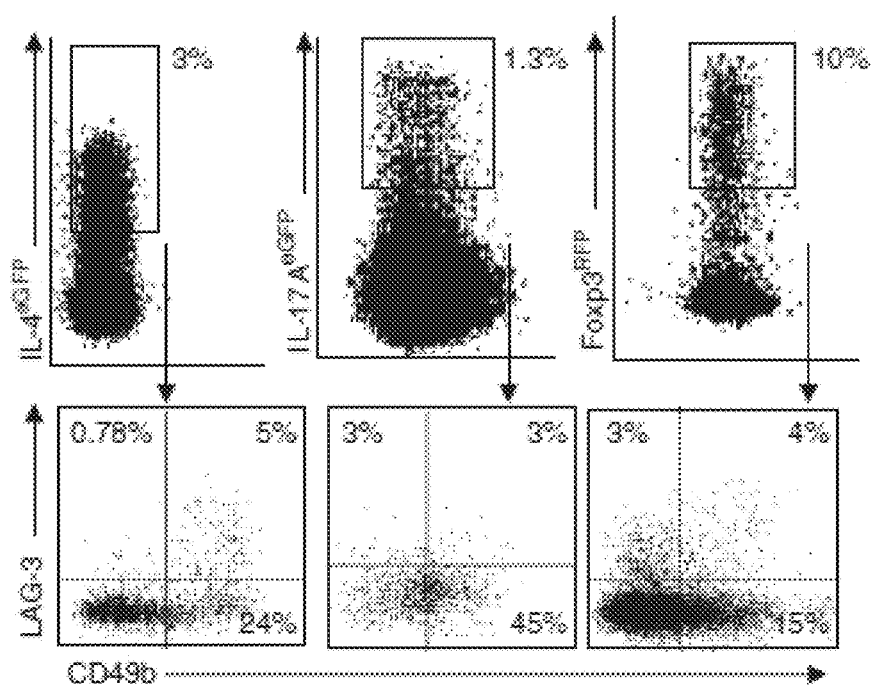
FIG. 5A through FIG. 5F, depicts the results of experiments demonstrating that co-expression of CD49b and LAG-3 is specific for murine Tr1 cells.
Figure 5C:
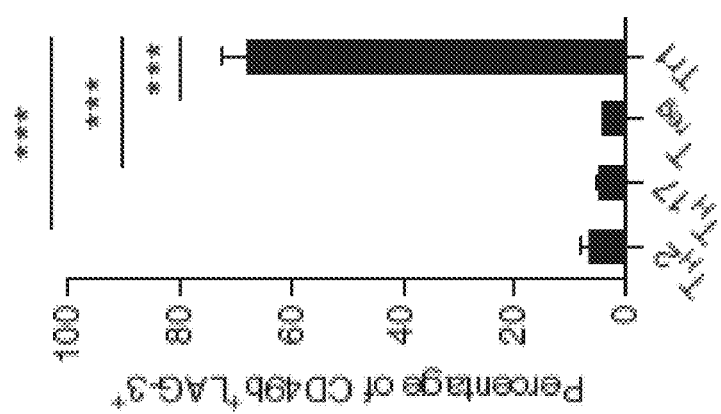
Figure 14E:
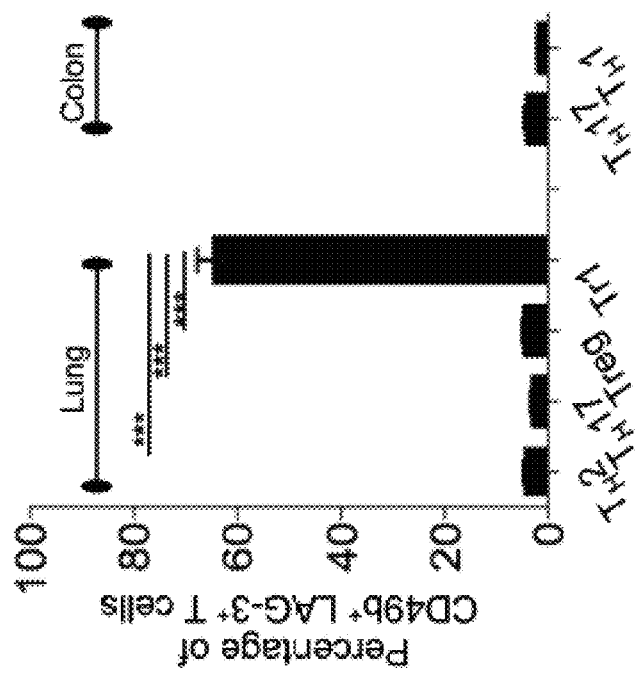

IL-4$^{eGFP}$ reporter mice were infected with *N. brasiliensis* to examine T$_H$2 cells. In this model the larvae enter the lung 2-3 days after subcutaneous injection causing haemorrhage and massive inflammation (Chen et al., 2012, Nat Med 18, 260-266) (FIGS. 14A and 14B). Within 9-10 days the adult worms are expelled due to the development of T$_H$2-type responses Wills-Karp et al., 2012, J Exp Med 209, 607-622; Mohrs et al., 2001, Immunity 15, 303-311). In the present study, it is shown that the majority of T$_H$2 (CD4$^+$IL-4$^{eGFP+}$) cells present in draining lymph nodes (LNs) (FIGS. 5A, and 5D) and in the lungs (FIGS. 14C and 14E) did not co-express CD49b and LAG-3.

*N. brasiliensis* infection also induces a strong IL-17 response in the lungs, which contributes to inflammation and tissue damage (Chen et al., 2012, Nat Med 18, 260-266). It was observed that both T$_H$17 (CD4$^+$Foxp3$^{RFP-}$IL-17A$^{GFP+}$) and Foxp3$^+$ Tregs (CD4$^+$Foxp3$^{RFP+}$IL-17A$^{GFP-}$) cells were induced by *N. brasiliensis*. These cells accumulated in the draining LNs and in the lungs and did not co-express CD49b and LAG-3 (FIGS. 5A, 5C, 14C, and 14E).

Figure 14D:
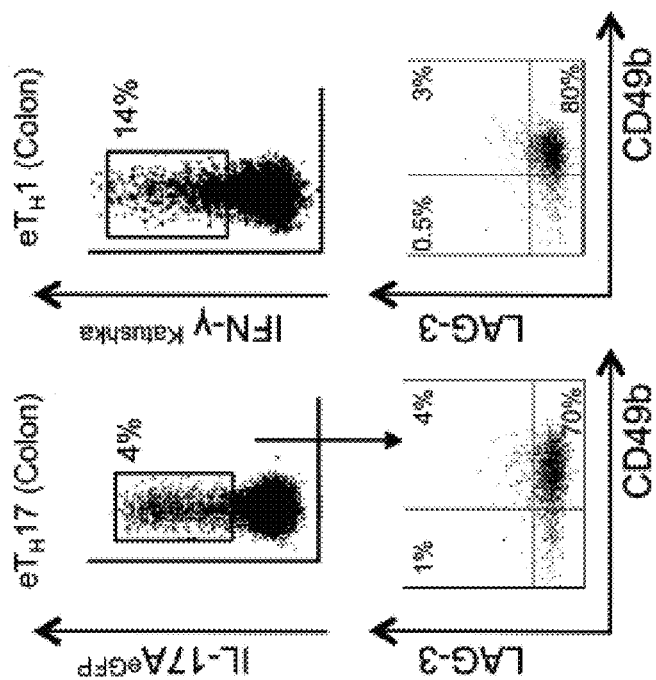

To further prove that T$_H$17 cells do not co-express CD49b and LAG-3, these cells were isolated from the colon of the previously described IBD model (Huber et al., 2011, Immunity 34, 554-565). Colitogenic Foxp3$^{RFP-}$IL-17A$^{eGFP+}$ cells, which include T$_H$17 and a significant proportion of 'T$_H$1+T$_H$17' cells (Huber et al., 2011, Immunity 34, 554-565), and CD4$^+$Foxp3$^{RFP-}$IL-17A$^{eGFP-}$ T cells, which contained almost 30-40% of IFN-γ-producing T$_H$1 cells, expressed CD49b, but not LAG-3 (FIGS. 14D and 14E). Furthermore, colitogenic T$_H$1 (Foxp3$^{RFP-}$IFN-γ$^{Katushka+}$) cells did not co-express CD49b and LAG-3 (FIGS. 14D and 14E).

Thus, as demonstrated herein, unlike Tr1 cells, T$_H$1, T$_H$2, T$_H$17, and Foxp3$^+$ Treg cells do not co-express CD49b and LAG-3 in vivo.

Figure 5B:
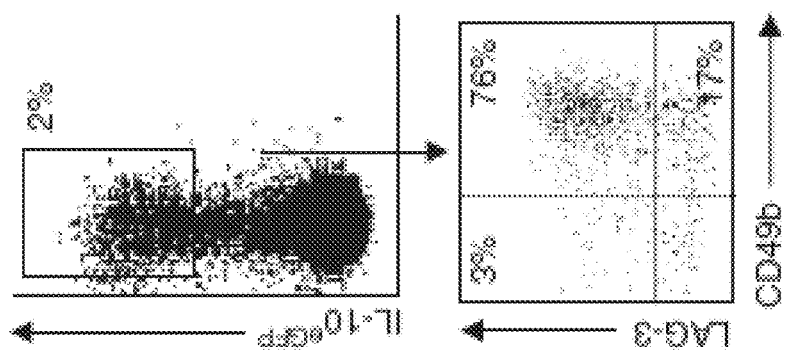
Figure 5D:
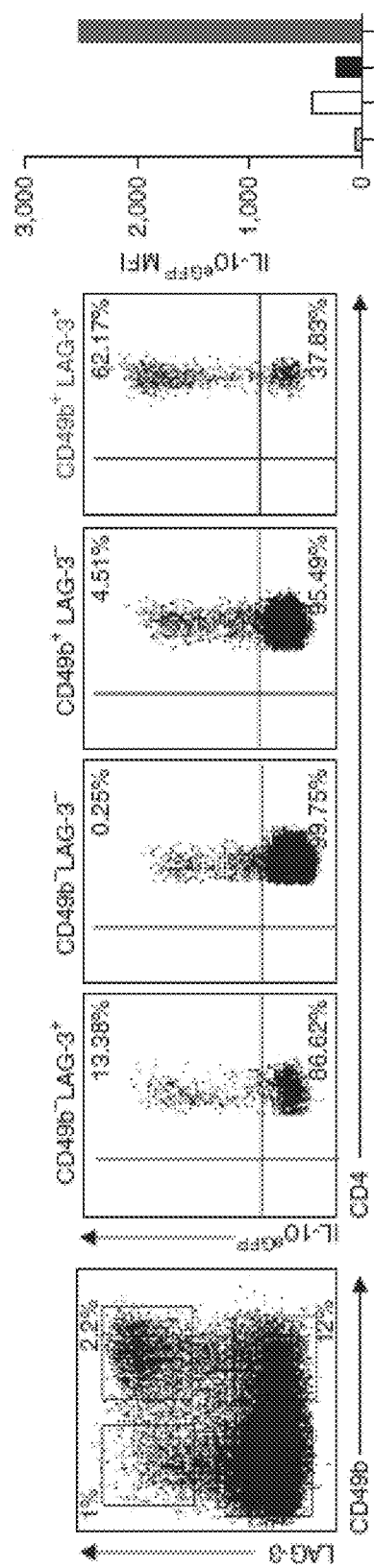
Figure 5E:
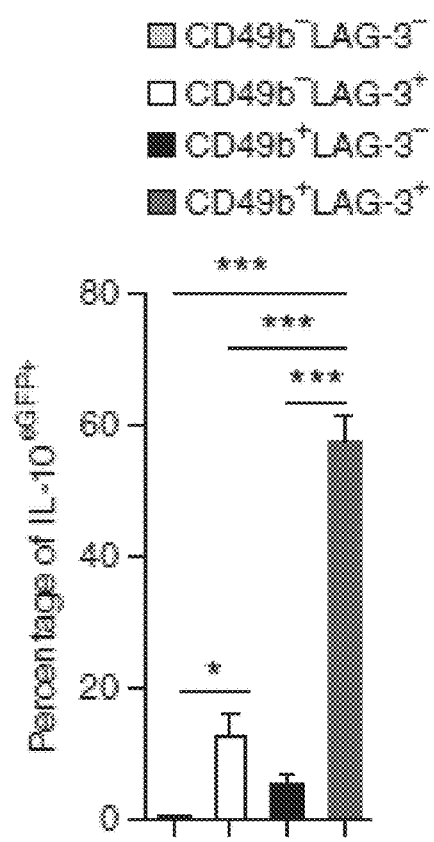
Figure 5F:
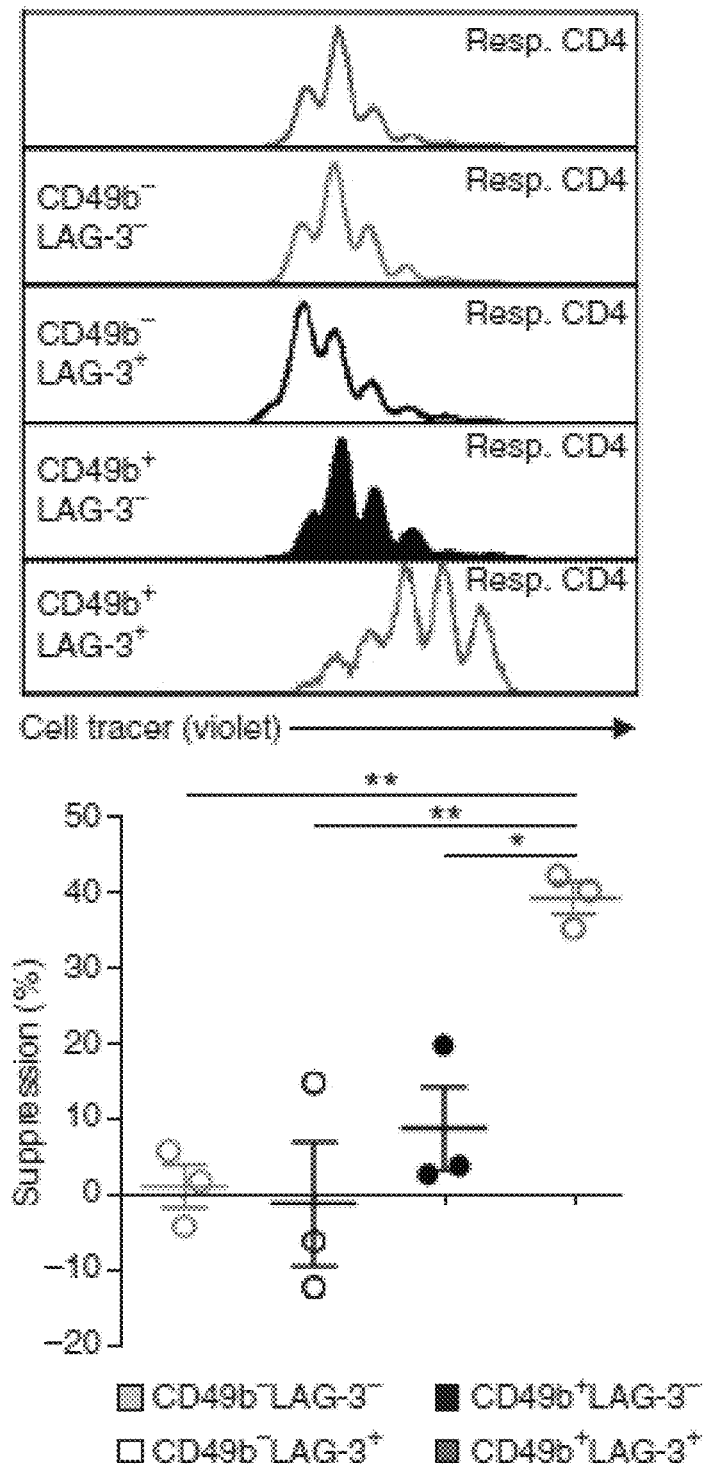
Figure 15A:
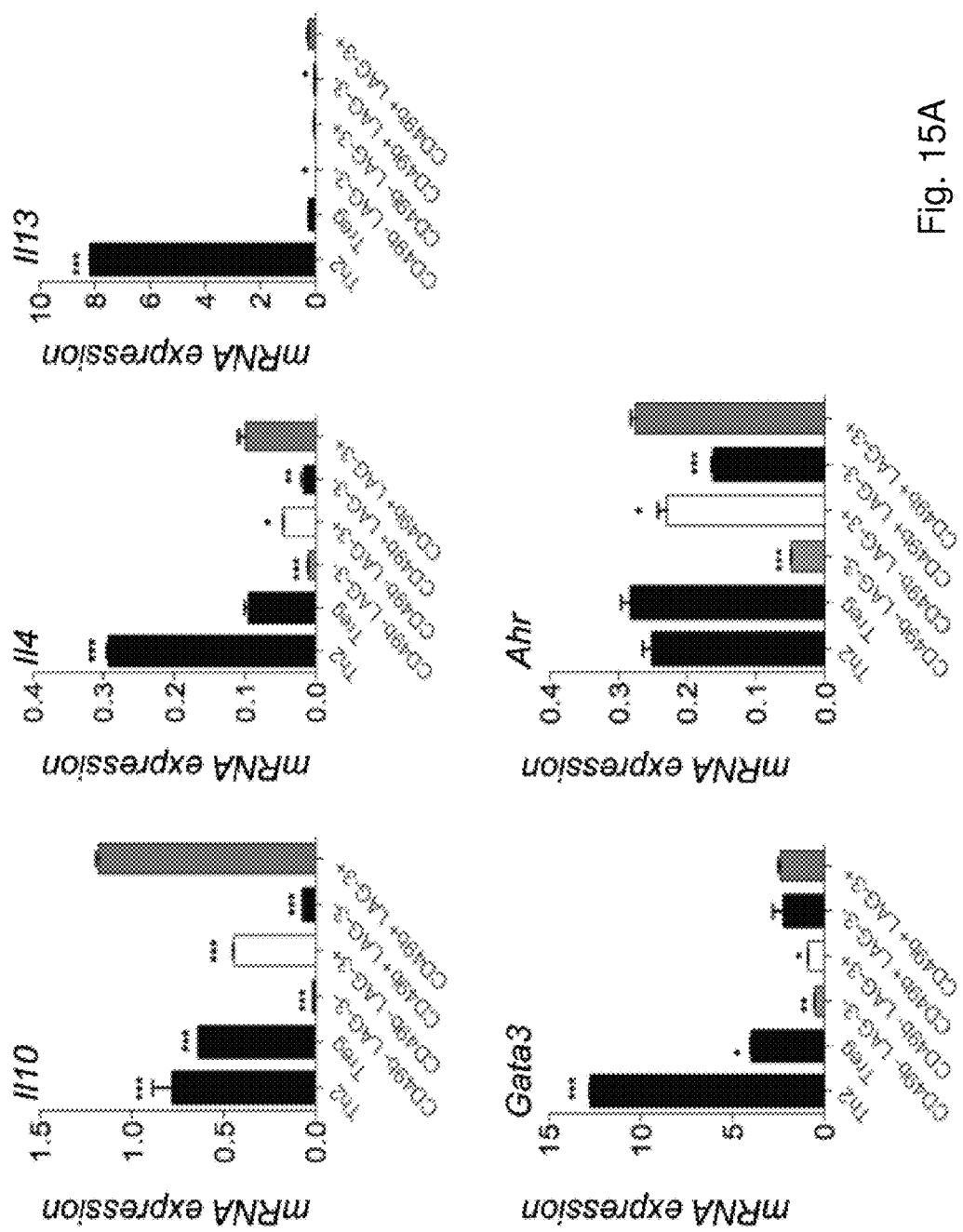

During the late phase of *N. brasiliensis* infection (day 10 post-infection) IL-10 production increases and contributes to the resolution of inflammation and consequently tissue damage (Chen et al., 2012, Nat Med 18, 260-266), suggesting the induction of Tr1 cells. CD4$^+$Foxp3$^-$IL-10$^+$ T cells were found in the draining LNs and lung of *N. brasiliensis* infected mice (FIGS. 5B, 5C, 14C and 14E). The large majority of CD4$^+$Foxp3$^{RFP-}$IL-10$^{GFPbright}$ T cells were CD49b$^+$LAG-3$^+$ (FIG. 5B and FIG. 14C). Moreover, CD4$^+$ T cells co-expressing CD49b and LAG-3 contained the highest frequency of IL-10$^{eGFP+}$ cells with the highest MFI (FIGS. 5D, and 5E). CD4$^+$CD49b$^+$LAG-3$^+$ T cells FACS-sorted from draining LNs of infected mice expressed high levels of Il10 mRNA (FIG. 15S) and suppressed the proliferation of effector CD4$^+$ T cells in vitro (FIG. 5F). Notably, during helminth infection in which the concentration of T$_H$2-type cytokines is particularly enhanced in innate and adaptive cells, CD4$^+$CD49b$^+$LAG-3$^+$ T cells expressed Il4, Il13, and Gata3 mRNA at levels comparable to those expressed by Foxp3$^+$ Treg cells, but significantly lower than those in T$_H$2 cells (FIG. 15A). Expression of Ahr in CD4$^+$ CD49b$^+$LAG-3$^+$ T cells was high but not selective.

Seven days after *N. brasiliensis* infection Tr1 cells accumulated both in the lungs and draining LNs (FIGS. 15B and 15C), which is in line with the described role of IL-10 during resolution of infection (Chen et al., 2012, Nat Med 18, 260-266). The frequency of Tr1 cells (FIGS. 15B and 15C) decreased in infected mice over time, but CD49b and LAG-3 were stably co-expressed by CD4+Foxp3$^{RFP-}$IL-10$^{GFPbright}$ cells (FIGS. 15B and 15C).

Figure 16A:
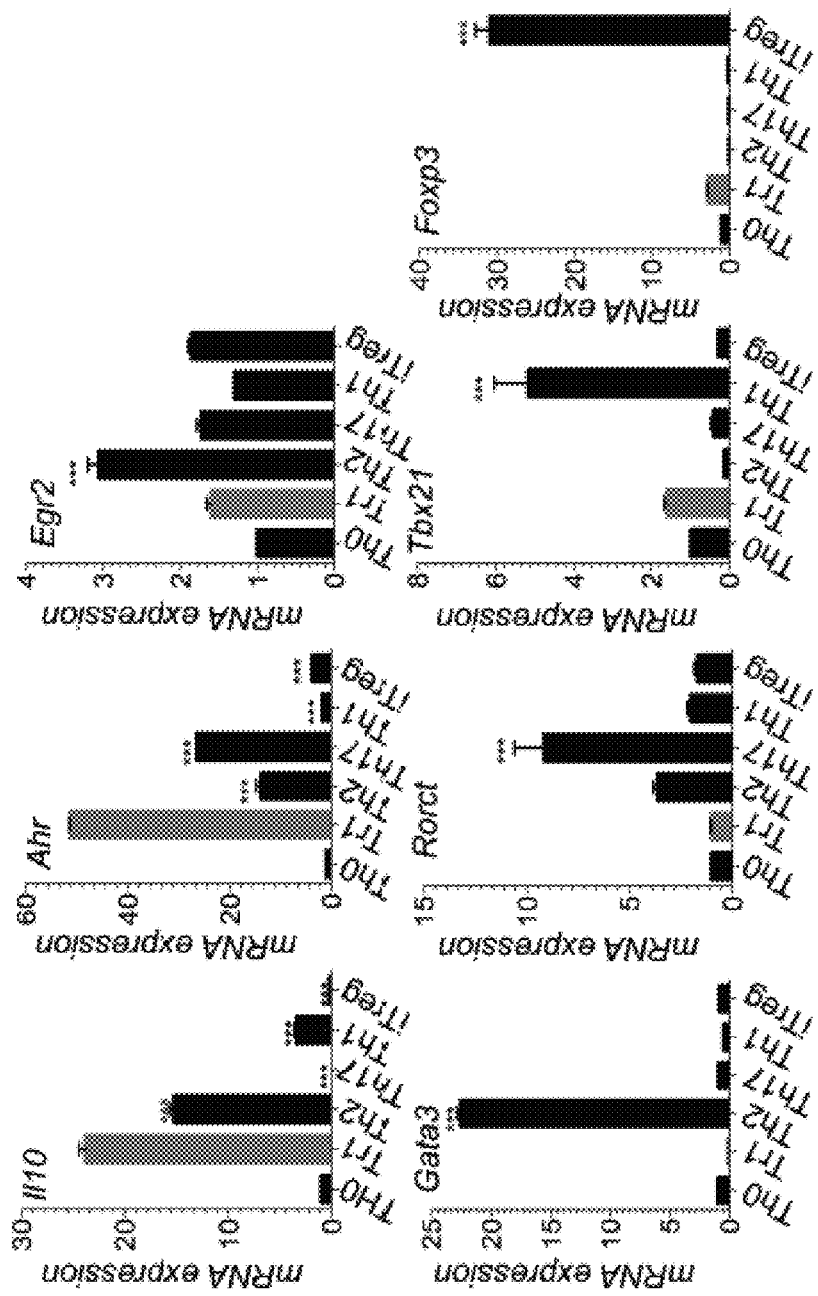
FIG. 16A through FIG. 16C, depicts the results of experiments demonstrating that in vitro differentiated Tr1 cells co-express CD49b and LAG-3.
Figure 16B:
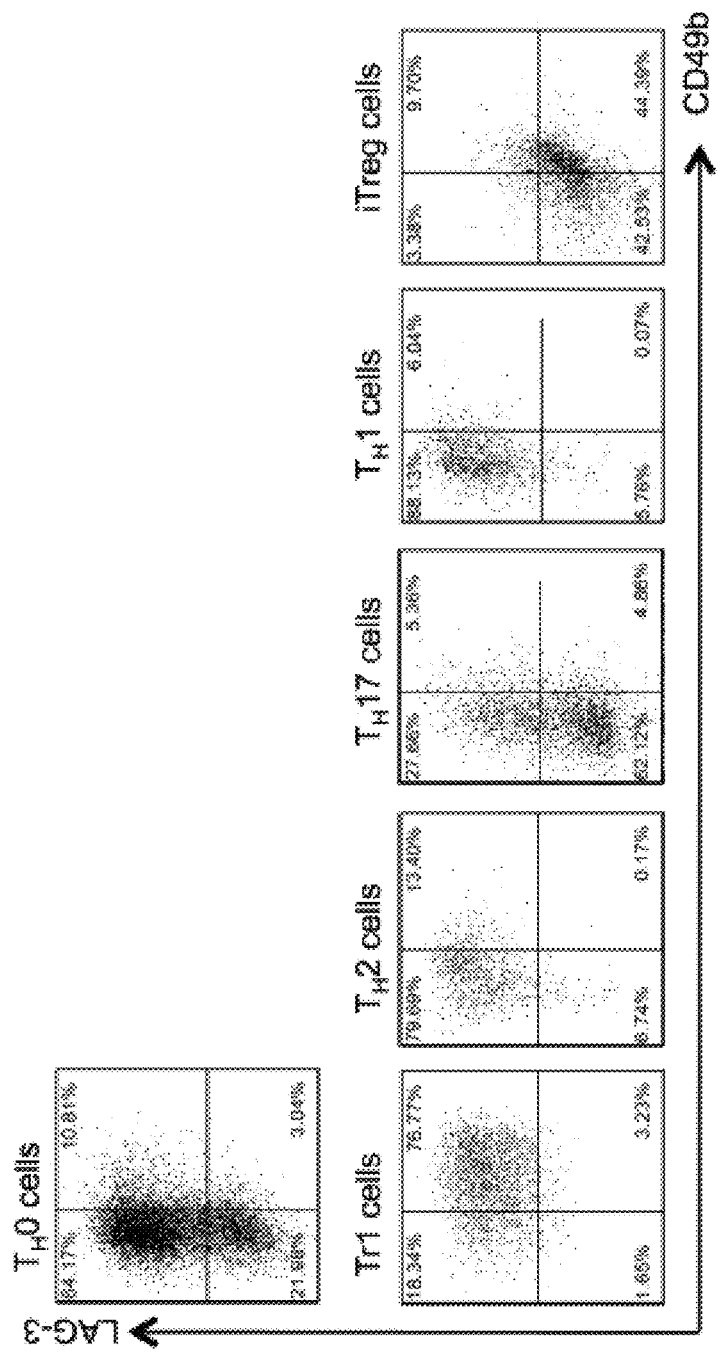
Figure 16C:
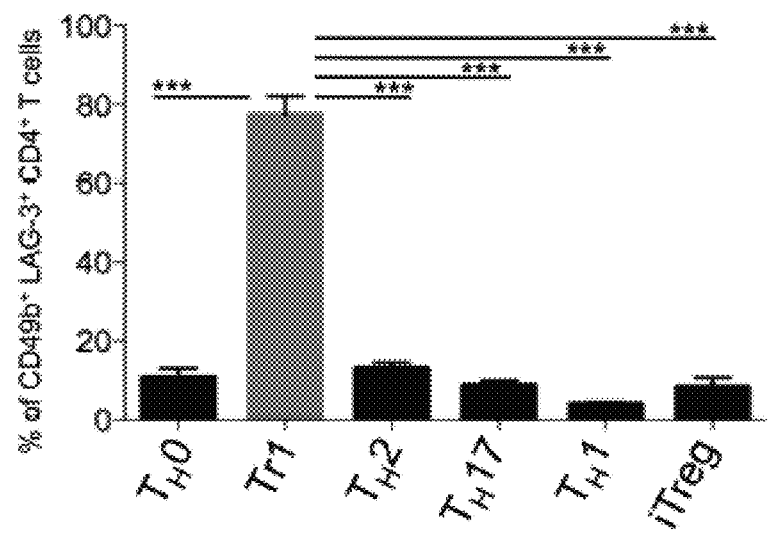
Figure 17A:
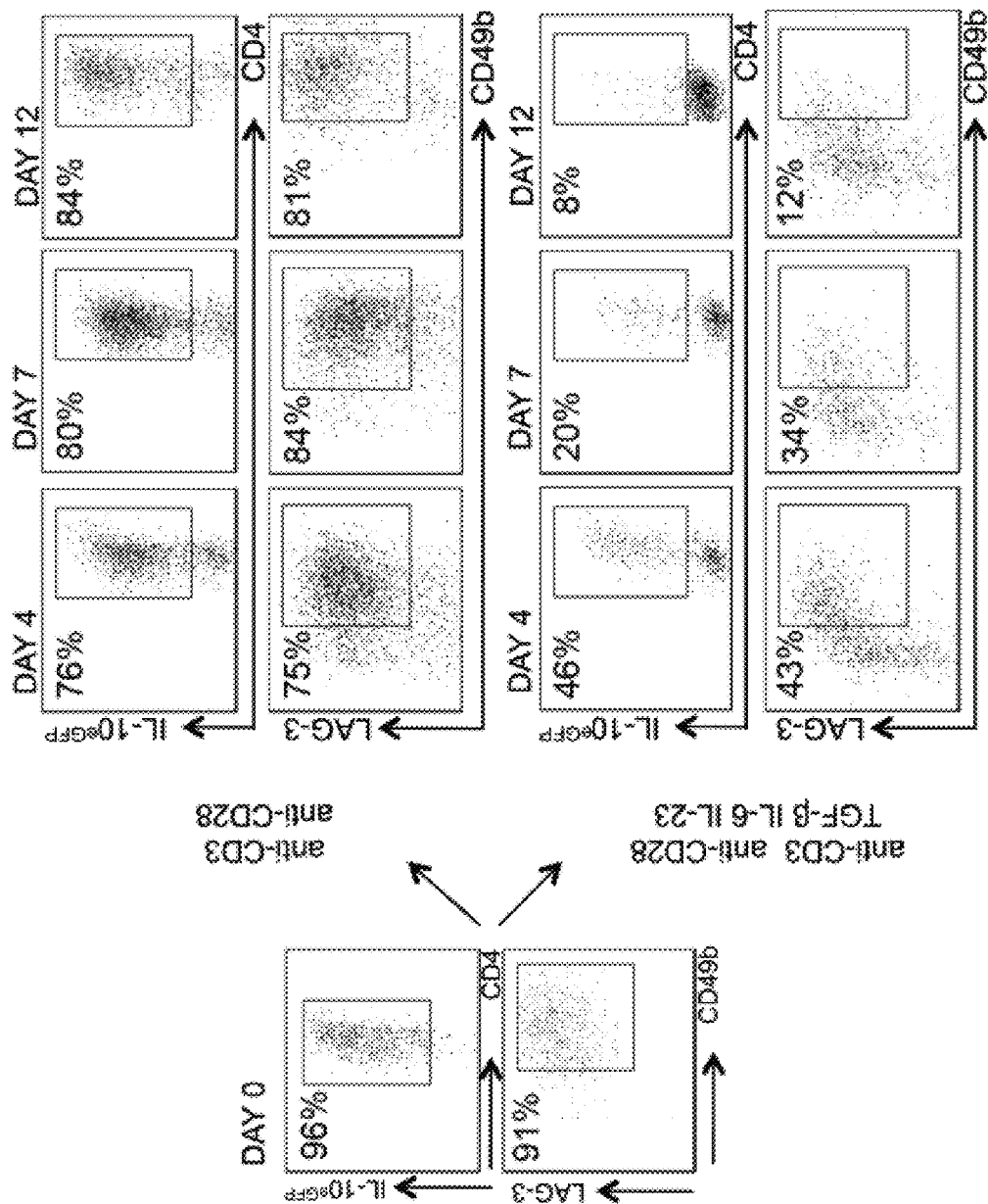
FIG. 17A and FIG. 17B, depicts the results of experiments demonstrating that CD49b and LAG-3 are expressed over time on in vitro generated Tr1 cells. CD4$^+$ T cells were isolated from the spleen of wild type mice and in vitro differentiated in Tr1 cells with IL-27 and TGF-β.
Figure 17B:
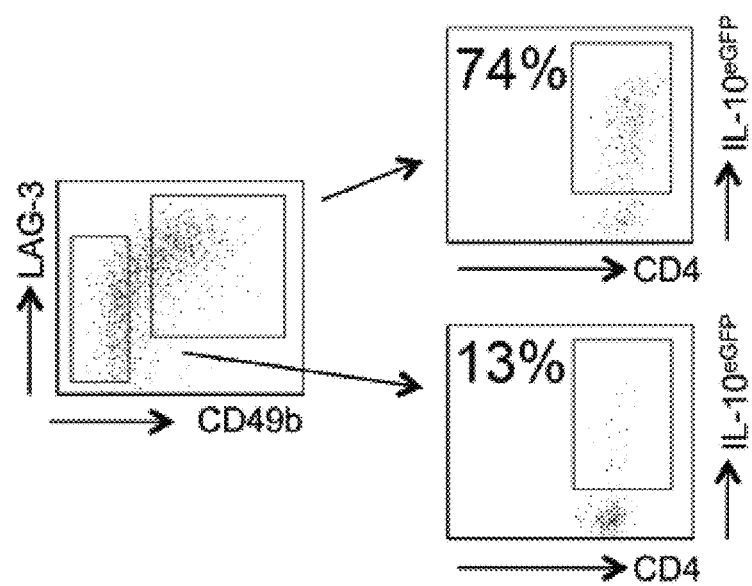
Figure 18C:
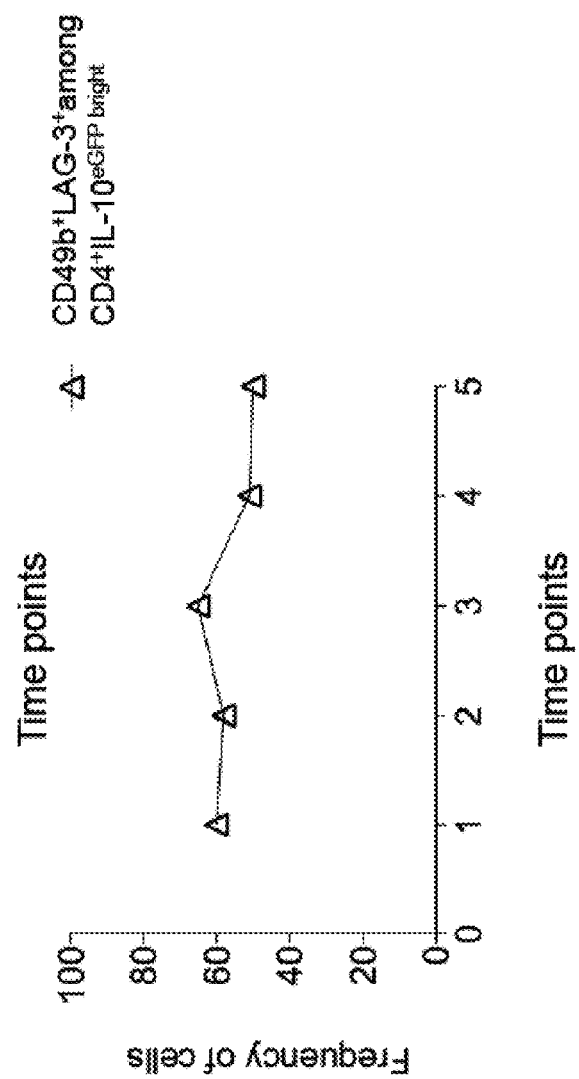

The expression and stability of CD49b and LAG-3 on Tr1 cells was also confirmed in Tr1 cells differentiated in vitro with IL-27 and TGF-β. Tr1 cells expressed Il10 and AhR at significantly higher levels than in vitro differentiated T$_H$1, T$_H$2, T$_H$17 and iTreg cells (FIG. 16A). Similar to CD4$^+$ CD49b$^+$LAG-3$^+$ T cells from the small intestine of anti-CD3 treated mice, expression of Erg2, Gata3, Rorct, Tbx21, and Foxp3 was low or undetectable in in vitro-induced Tr1 cells (FIG. 16A). Interestingly, the majority of IL-27-induced Tr1 cells were CD49b$^+$LAG-3$^+$ (FIGS. 16B and 16C) and the expression of CD49b/LAG-3 remained stable in vitro on IL-10-producing Tr1 cells (FIGS. 17A and 17B). Notably, after in vivo transfer, Tr1 cells that maintained IL-10 expression stably remained CD49b$^+$LAG-3$^+$ cells (FIGS. 18A and 18B).

Thus, the studies presented herein demonstrate that CD49b and LAG-3 are selectively and stably co-expressed by IL-10-producing Tr1 cells, but not by T$_H$1, T$_H$2, T$_H$17, and Foxp3$^+$ Treg cells.

Clinical Application of Tr1 Cell Specific Surface Markers

Figure 6A:
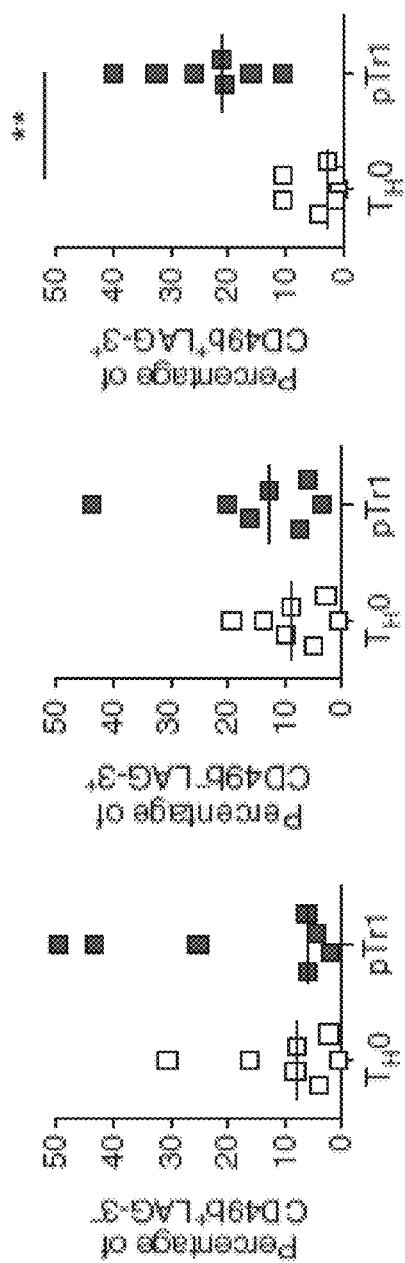
FIG. 6A through FIG. 6F, depicts the results of experiments demonstrating that co-expression of CD49b and LAG-3 allows the selection of human Tr1 cells in vitro and the enumeration of Tr1 cells in vivo in tolerant subjects.
Figure 6B:
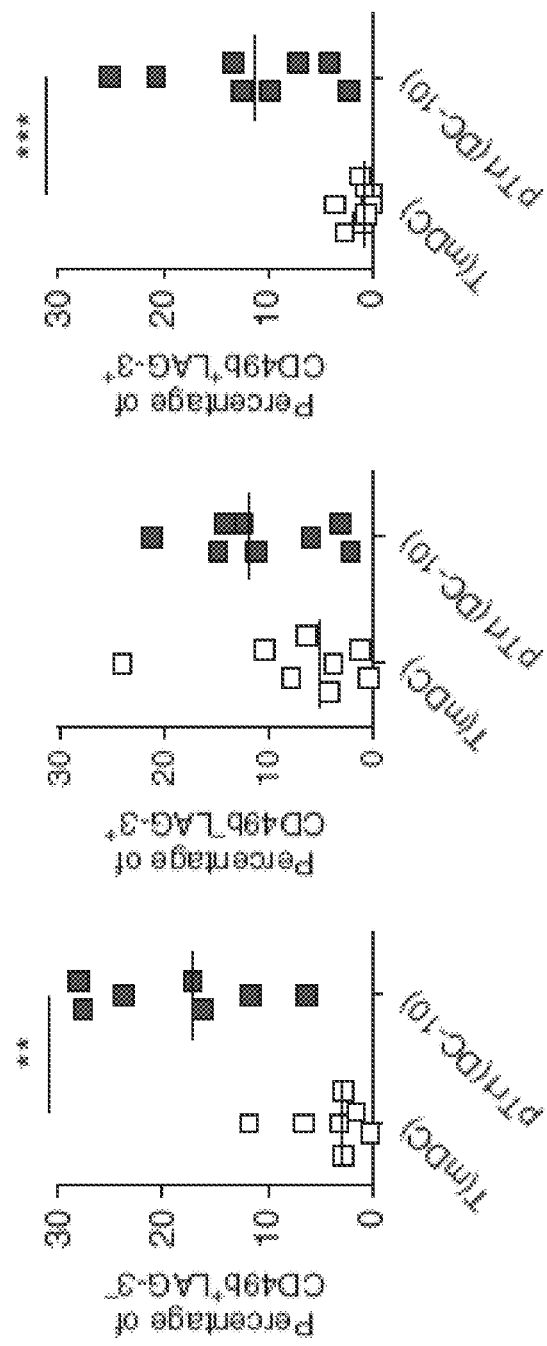
Figure 6C:
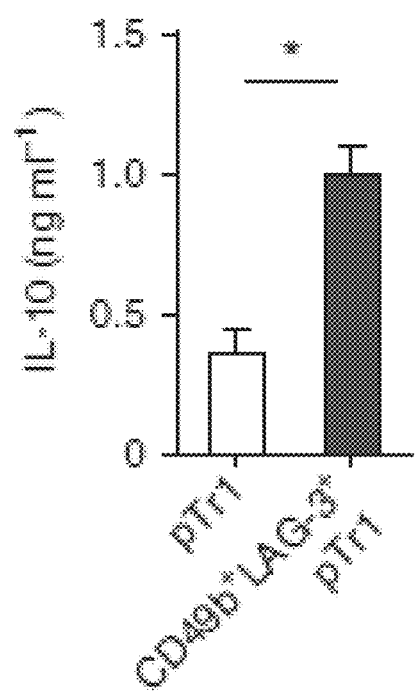
Figure 6D:
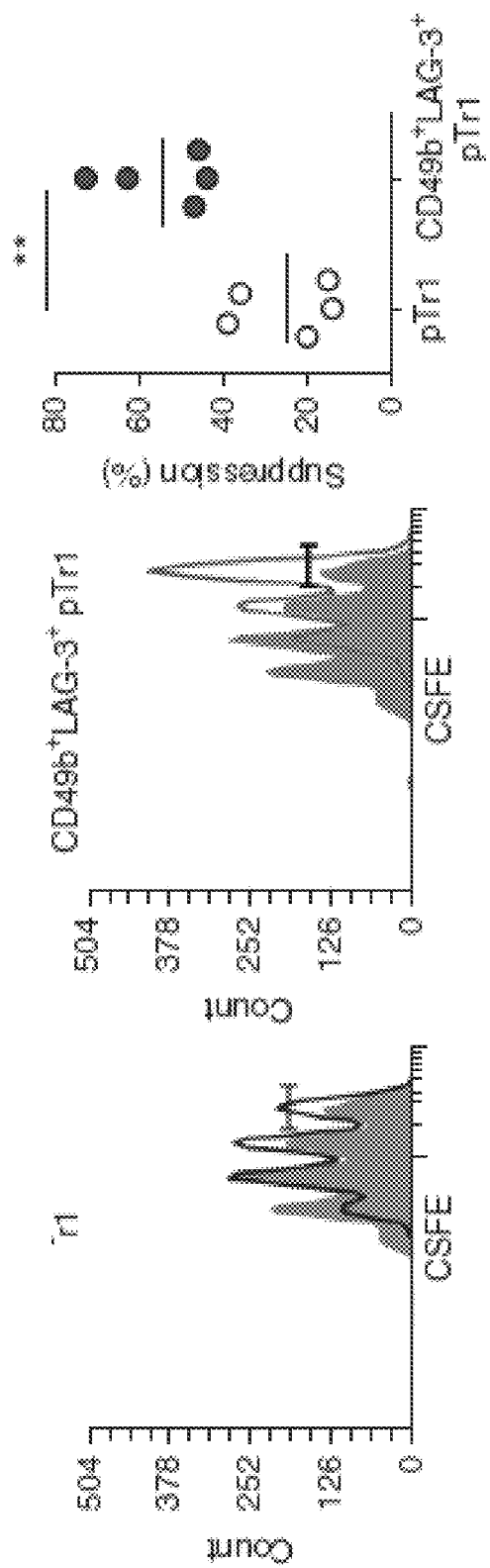
Figure 19A:
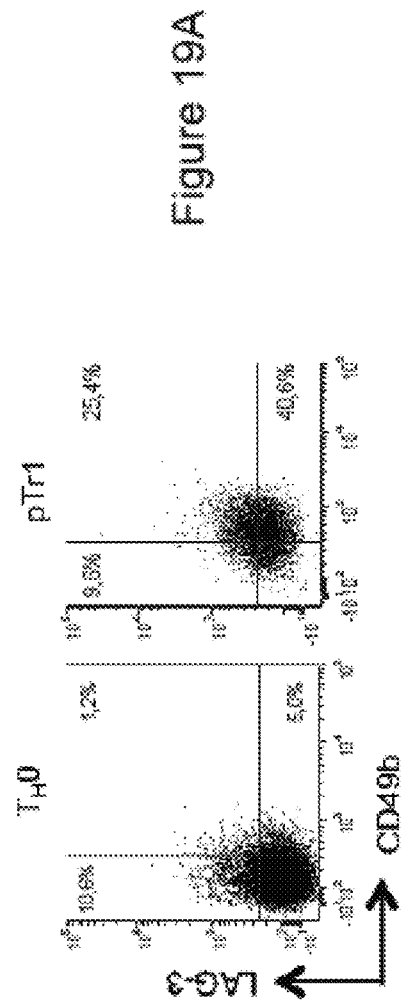
FIG. 19A and FIG. 19B, depicts the results of experiments demonstrating that co-expression of CD49b and LAG-3 allows the selection of human Tr1 cells in vitro.
Figure 19B:
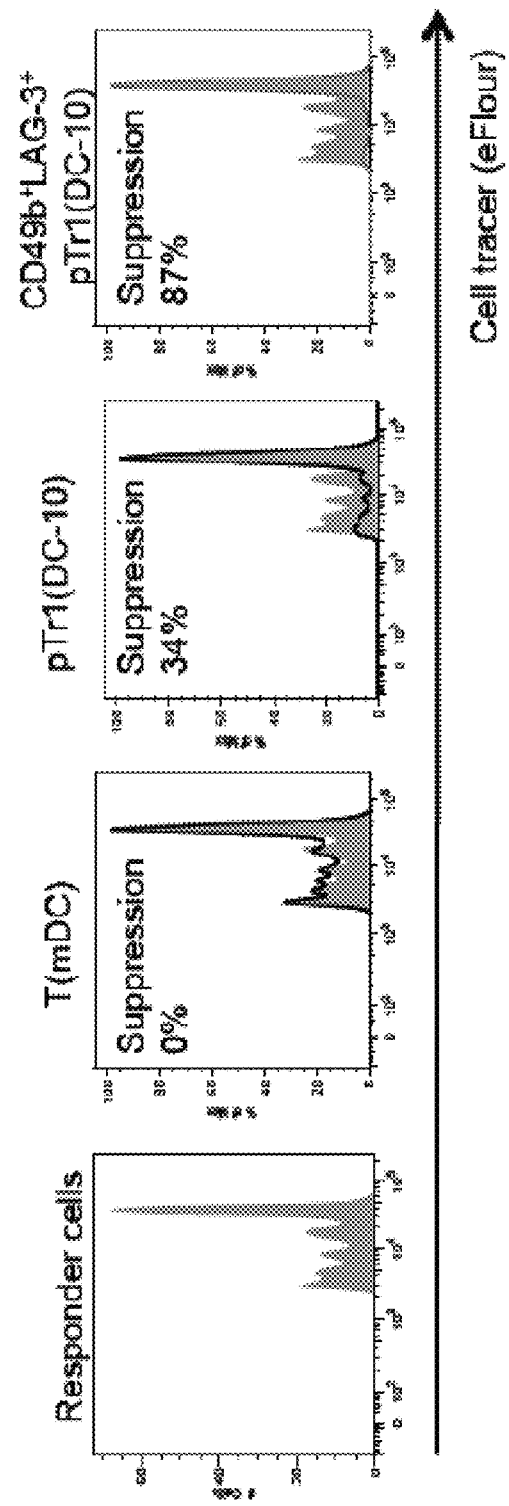

To generate Tr1 cells in vitro for therapeutic use, human T cells were polarized in the presence of IL-10. The resulting cell population contains only a small proportion of Tr1 cells and is contaminated by a large fraction of non-IL-10-producing T cells (Bacchetta et al., 2010, Haematologica 95, 2134-2143). Using previously described protocols to differentiate human Tr1 cells in vitro (Magnani et al., 2011 Eur J Immunol 41, 1652-1662; Levings et al., 2001, J Immunol 166, 5530-5539; Gregori et al., 2010, Blood 116, 935-944; Gregori et al., 2011, Methods in molecular biology 677, 31-46), it was shown that the frequency of T cells co-expressing CD49b and LAG-3 was significantly higher in Tr1-polarized cells (FIG. 6A and FIGS. 6B and 19A), compared to T$_H$0 cells. FACS-sorted CD49b$^+$LAG-3$^+$ T cells from Tr1-polarized cells secreted significantly higher levels of IL-10 (FIG. 6C) and displayed higher suppressive capacity relative to the original bulk population (FIGS. 6D and 19B), indicating that CD49b and LAG-3 can be used to purify Tr1 cells from in vitro polarized cells.

Figure 6E:
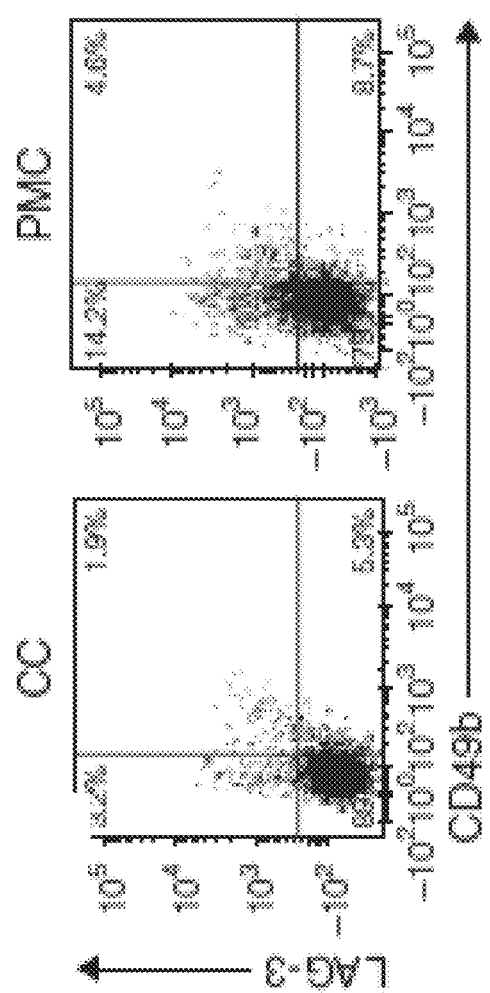
Figure 6F:
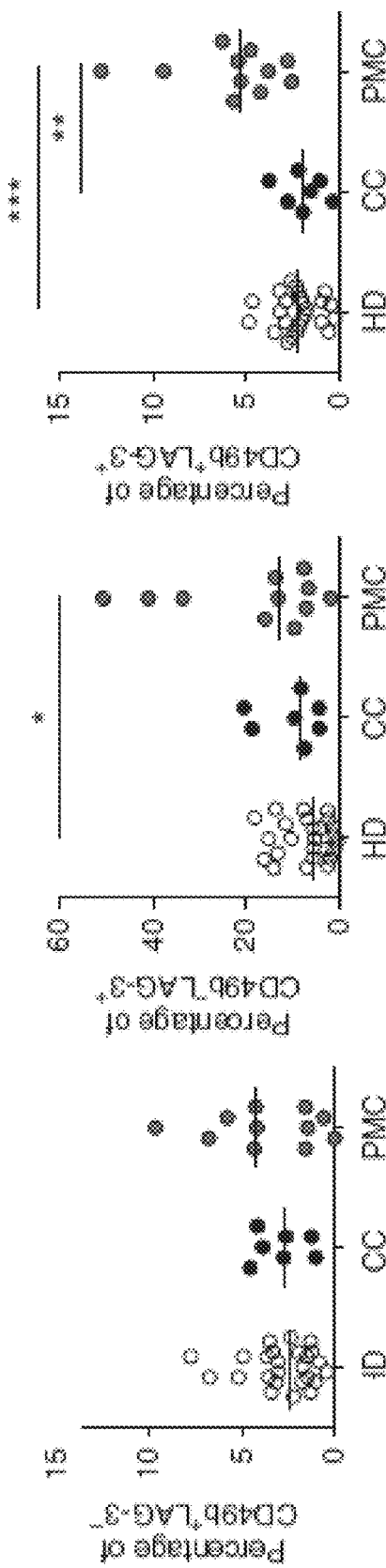
Figure 20A:
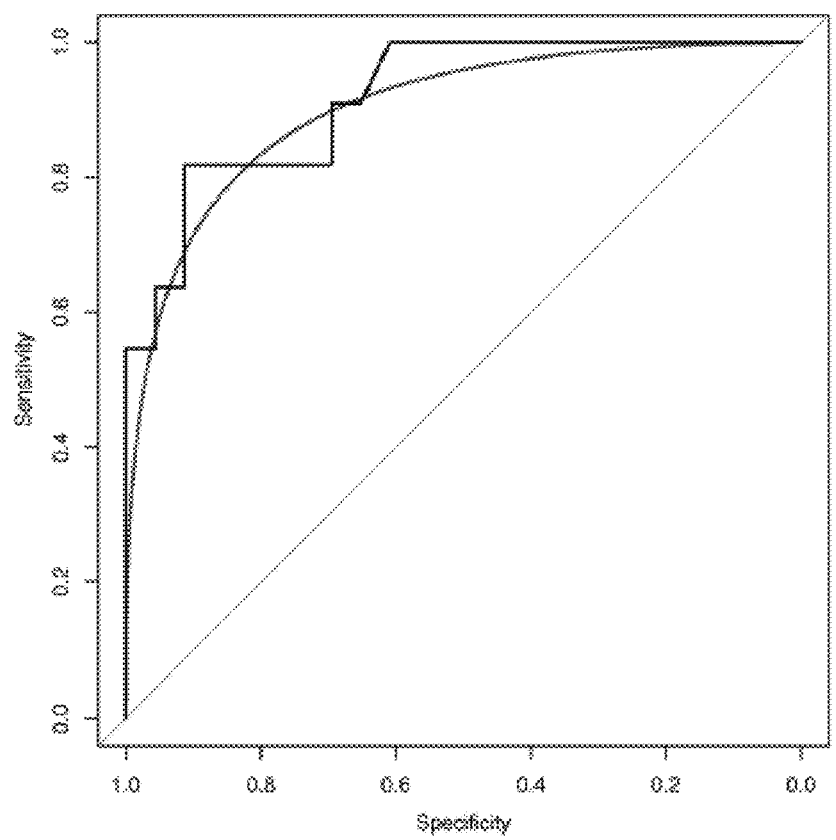
FIG. 20A and FIG. 20B, depicts the results of experiments demonstrating the sensitivity and specificity of the co-expression of CD49b and LAG-3 on human CD4$^+$CD45RA$^-$ T cells. Empirical Receiver Operating Characteristic (ROC) curves generated by comparing subjects with persistent mixed chimerism after allogeneic HSCT (PMC, n=1) with healthy donors (HDs, n=23) (FIG. 20A), or with subjects with complete chimerism (CC, n=7) (FIG. 20B). Area under the curve (AUC) were 0.900 and 0.916, respectively. A threshold of 3.64% for CD49b$^+$LAG-3$^+$ T cells gave 81.8% sensitivity and 91.3% specificity when PMC were compared to HDs. A threshold of 2.765% for CD49b$^+$LAG-3$^+$ T cells gave 91% sensitivity and 87.5% specificity when PMC were compared to CC.
Figure 20B:
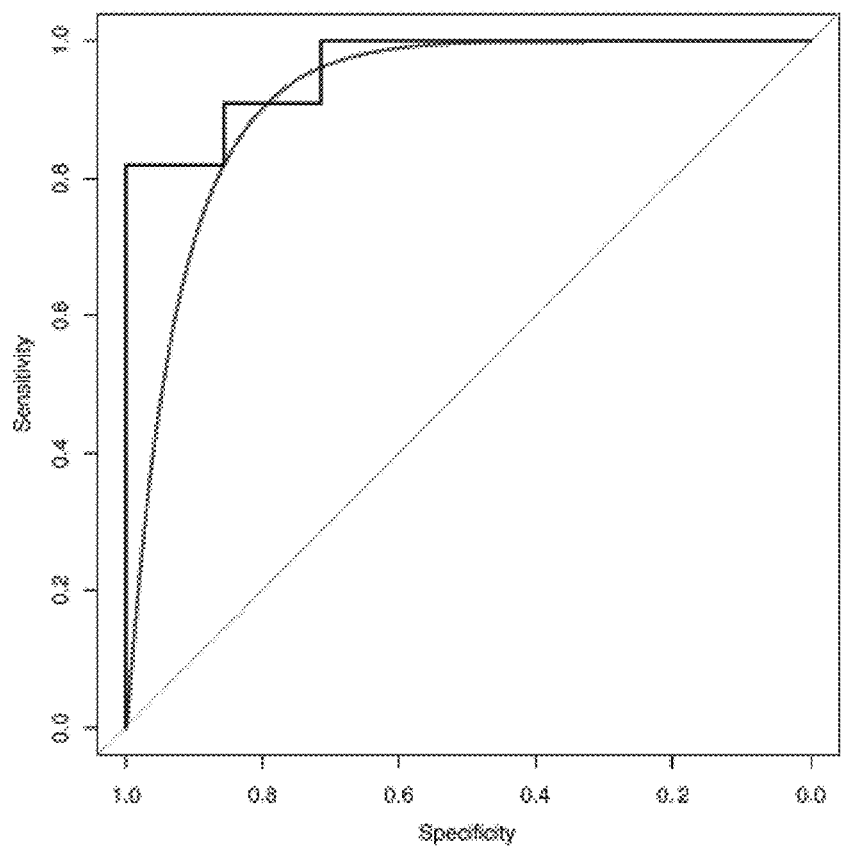

The frequency of CD49b$^+$LAG-3$^+$ T cells was assessed in a unique cohort of β-thalassemic subjects in which persistent mixed chimerism (PMC) of donor and host cells after allogeneic HSCT correlates with tolerance and the presence of circulating CD4$^+$IL-10$^+$ cells (Serafini et al., 2009, Haematologica 94, 1415-1426). Circulating CD49b$^+$LAG-3$^+$ T cells were significantly higher in peripheral blood of subjects with PMC (Andreani et al., 2011, Chimerism 2, 21-22; Andreani et al., 2011, Haematologica 96, 128-133) compared to both HDs or subject with complete chimerism (CC) (FIGS. 6E and 6F). The statistical analysis confirmed that the percentage of CD49b$^+$LAG-3$^+$ T cells can be used to discriminate tolerant subjects from controls (HDs or CC) (FIGS. 20A and 20B). These findings demonstrate that the concomitant expression of CD49b and LAG-3 allows the isolation of Tr1 cells from in vitro Tr1-polarized populations and to trace Tr1 cells in vivo in tolerant subjects.

Co-Expression of CD49b and LAG-3b

The studies presented herein demonstrate that co-expression of CD49b and LAG-3 identifies human and murine Tr1 cells. CD4$^+$CD49b$^+$LAG-3$^+$ T cells secrete large amounts of IL-10, display a high IL-10/IL-4 and IL-10/IL-17 ratio, express high levels of CD226, do not express high Foxp3 and possess strong IL-10-dependent regulatory activity. Concomitant expression of CD49b and LAG-3 is specific for Tr1 cells, since $T_H1$, $T_H2$, $T_H17$ and Foxp3$^+$ Treg cells do not co-express these markers. Co-expression of CD49b and LAG-3 can be used to purify human Tr1 cells from in vitro Tr1-polarized cell cultures, and enables tracing of Tr1 cells in tolerant subjects.

Expression of CD49b has been previously described on effector memory CD4$^+$ T cells (Kassiotis et al., 2006, J Immunol 177, 968-975), $T_H17$ cells (Boisvert et al., 2010, Eur J Immunol 40, 2710-2719) and IL-10-producing T cells (Charbonnier et al., 2006, J Immunol 177, 3806-3813; Rahmoun et al., 2006, Int Arch Allergy Immunol 140, 139-149). The present data shows that CD49b is expressed on Tr1 cells, but also on $T_H1$, $T_H2$, $T_H17$ cells and Foxp3$^+$ Treg cells. LAG-3 is expressed on splenic T cells isolated from naïve mice with regulatory function and correlates with IL-10 production (Okamura et al., 2009, Proc Natl Acad Sci USA 106, 13974-13979; Huang et al., 2004, Immunity 21, 503-513). However, activated T cells also express LAG-3 (Workman and Vignali, 2005, J Immunol 174, 688-695; Bettini et al., 2011, J Immunol 187, 3493-3498; Bruniquel et al., 1998, Immunogenetics 48, 116-124; Lee et al., 2012, Nat Immunol 13, 991-999; Huard et al., 1997, Proc Natl Acad Sci USA 94, 5744-5749). It is shown that murine and human T cells expressing LAG-3 but not CD49b produce IL-4, low amounts of IL-10, are highly proliferative, and do not display significant suppressive activity in vitro.

Thus, the use of either CD49b alone or LAG-3 alone, is not sufficient to select a highly enriched population of functional Tr1 cells, or to distinguish these cells from other $T_H$ or Treg cell subsets. It is demonstrated herein that the combination of CD49b and LAG-3 is required to identify and select murine and human Tr1 cells, which secrete high levels of IL-10 and have regulatory activity in vitro and in vivo. Both CD49b and LAG-3 are stably expressed on functional Tr1 cells. CD49b is expressed by Tr1 cells irrespectively of their activation, whereas LAG-3 is expressed on Tr1 cells when they produce IL-10 and display suppressor activity. Co-expression of CD49b and LAG-3 distinguishes Tr1 cells from $T_H1$, $T_H2$, $T_H17$ cells during helminth infection and IBD.

The identification of Tr1 cells in patients has been limited by their ability to produce IL-10 only upon in vitro re-stimulation (Bacchetta et al., 1994, J Exp Med 179, 493-502; Meiler et al., 2008, J Exp Med 205, 2887-2898; Petrich de Marquesini et al., 2010, Diabetologia 53, 1451-1460; Sanda et al., 2008, Clin Immunol 127, 138-143). Moreover, intracellular flow cytometric analysis of IL-10 expression is insensitive and is highly variable according to the type of stimuli. Alternatively, T-cell cloning of circulating CD4$^+$ T cells allows the enumeration of IL-10-producing Tr1 cells in tolerant subjects (Bacchetta et al., 1994, J Exp Med 179, 493-502; Gregori et al., 2011, Methods in molecular biology 677, 31-46). Using these techniques, it was previously demonstrated that high frequencies of IL-10-producing T cells and of Tr1 cell clones in peripheral blood of allogeneic HSCT transplanted subjects correlated with persistent mixed chimerism and tolerance (Bacchetta et al., 1994, J Exp Med 179, 493-502; Serafini et al., 2009, Haematologica 94, 1415-1426). It is shown herein that in these tolerant subjects the frequency of CD4$^+$CD49b$^+$LAG-3$^+$ T cells is significantly increased. Statistical analysis shows significant differences in the percentages of CD49b$^+$LAG-3$^+$ T cells in tolerant subjects versus control groups. Since CD49b$^+$LAG-3$^+$ T cells are IL-10-producing suppressor T cells, these data indicate that the frequency of Tr1 cells can be monitored in vivo using these markers.

Regulatory T cell-based therapies have become an attractive therapeutic option for inducing/restoring tolerance. Several protocols to generate and expand Tr1 cells in vitro have been developed (Bacchetta et al., 2010, Haematologica 95, 2134-2143; Brun et al., 2009, Int Immunopharmacol 9, 609-613), and proof-of-principle clinical trials demonstrating safety and feasibility of Tr1 cell-infusion have been recently completed (Bacchetta et al., 2009, Blood, 45 (ASH Annual Meeting Abstract; Desreumaux et al., 2012, Gastroenterology 143, 1207-1217 e1201-1202). However, the cell preparation consisting of antigen-specific IL-10-anergized T cells generated with recombinant IL-10 or DC-10 (Gregori et al., 2010, Blood 116, 935-944; Bacchetta and Gregori, 2010, Hematologica 95, 2134-2143) still contains a subset of contaminating non-Tr1 cells, which could potentially exacerbate the pathogenic clinical condition of patients. The data presented herein show that CD49b and LAG-3 co-expression allows the isolation of Tr1 cells from in vitro Tr1-polarized populations and from antigen-specific IL-10-anergized T cells, thereby rendering their clinical use safer and broadening their clinical application.

In summary, two selective markers for Tr1 cells that are conserved in mice and humans have been discovered. These markers make it possible to study the in vivo localization of Tr1 cells in physiological conditions, as well as the role of Tr1 cells in subjects with immune-mediated diseases in which a defect in Tr1 cells has been proposed.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of isolating an enriched population of human Tr1 cells from a biological sample of a subject by flow cytometry, comprising the steps of:
   a. obtaining a T cell-containing biological sample of a subject,
   b. gating on CD4+CD45RA- cells and,
   c. isolating CD49b+ and LAG-3+ cells among the gated CD4+ and CD45RA- cells.

2. The method of claim 1, comprising the additional step of isolating cells from the biological sample of the subject that express the cell surface marker CD226.

3. The method of claim 2, wherein the cells express the cell surface marker CD226 at a level greater than the level of CD226 expressed by a comparator cell population.

4. The method of claim 3, wherein the comparator cell population is at least one selected from the group consisting of CD49b⁻LAG-3⁻T cells and $T_H0$ cells.

5. The method of claim 1, wherein greater than 90% of the cells in the enriched population of Tr1 cells express the cell surface markers CD4, and CD49b, and LAG-3.

6. The method of claim 1, wherein greater than 95% of the cells in the enriched population of Tr1 cells express the cell surface markers CD4, and CD49b, and LAG-3.

7. The method of claim 1, wherein greater than 98% of the cells in the enriched population of Tr1 cells express the cell surface markers CD4, and CD49b, and LAG-3.

8. The method of claim 1, wherein greater than 99% of the cells in the enriched population of Tr1 cells express the cell surface markers CD4, and CD49b, and LAG-3.

9. The method of claim 1, wherein isolating cells from the biological sample of the subject employs the use of an antibody that specifically binds to a cell surface marker.

10. The method of claim 9, wherein the cell surface marker is at least one selected from the group consisting of CD4, CD49b, and LAG-3.

11. The method of claim 1, wherein isolating cells from the biological sample of the subject employs the use of fluorescence-activated cell sorting (FACS).

12. The method of claim 1, wherein the biological sample is at least one selected from the group consisting of blood, bone marrow, cord blood, lymph nodes, thymus, and spleen.

13. The method of claim 1, wherein the T cell-containing biological sample is a cell preparation consisting of antigen-specific IL-10-anergized T cells generated with recombinant IL-10-treated dendritic cells (said cell preparation is also named DC-10).

* * * * *